United States Patent
Huffman et al.

(10) Patent No.: US 12,037,623 B2
(45) Date of Patent: Jul. 16, 2024

(54) ENZYMATIC SYNTHESIS OF 4'-ETHYNYL NUCLEOSIDE ANALOGS

(71) Applicant: Merck Sharp & Dohme Corp., Rahway, NJ (US)

(72) Inventors: Mark A. Huffman, Warren, NJ (US); Anna Fryszkowska, New York, NY (US); Joshua N. Kolev, Califon, NJ (US); Paul N. Devine, Tinton Falls, NJ (US); Kevin R. Campos, Berkeley Heights, NJ (US); Matthew Truppo, Princeton, NJ (US); Christopher C. Nawrat, Garwood, NJ (US)

(73) Assignee: Merck, Sharp & Dohme LLC, Rahway, NJ (US)

( * ) Notice: Subject to any disclaimer, the term of this patent is extended or adjusted under 35 U.S.C. 154(b) by 579 days.

(21) Appl. No.: 17/257,792

(22) PCT Filed: Jul. 2, 2019

(86) PCT No.: PCT/US2019/040316
§ 371 (c)(1),
(2) Date: Jan. 4, 2021

(87) PCT Pub. No.: WO2020/014041
PCT Pub. Date: Jan. 16, 2020

(65) Prior Publication Data
US 2022/0228184 A1    Jul. 21, 2022

Related U.S. Application Data

(60) Provisional application No. 62/695,508, filed on Jul. 9, 2018, provisional application No. 62/822,320, filed on Mar. 22, 2019.

(51) Int. Cl.
| | | |
|---|---|---|
| C12P 19/40 | (2006.01) | |
| C07C 33/042 | (2006.01) | |
| C07F 9/113 | (2006.01) | |
| C07H 13/00 | (2006.01) | |
| C12P 7/18 | (2006.01) | |
| C12P 9/00 | (2006.01) | |
| C12P 17/04 | (2006.01) | |

(52) U.S. Cl.
CPC ............ *C12P 19/40* (2013.01); *C07C 33/042* (2013.01); *C07F 9/113* (2013.01); *C07H 13/00* (2013.01); *C12P 7/18* (2013.01); *C12P 9/00* (2013.01); *C12P 17/04* (2013.01)

(58) Field of Classification Search
None
See application file for complete search history.

(56) References Cited

U.S. PATENT DOCUMENTS

| | | |
|---|---|---|
| 7,229,797 B1 | 6/2007 | Tischer et al. |
| 7,339,053 B2 | 3/2008 | Kohgo et al. |
| 2002/0022722 A1 | 2/2002 | Ohrui et al. |
| 2018/0002365 A1 | 1/2018 | Avila et al. |
| 2018/0002366 A1 | 1/2018 | Girijavallabhan et al. |
| 2020/0010815 A1 | 1/2020 | Borra-Garske et al. |
| 2020/0010823 A1 | 1/2020 | Novick et al. |
| 2020/0010834 A1 | 1/2020 | Novick et al. |
| 2020/0010868 A1 | 1/2020 | Duan et al. |
| 2020/0010869 A1 | 1/2020 | Micklitsch et al. |

FOREIGN PATENT DOCUMENTS

| | | |
|---|---|---|
| EP | 1178051 A2 | 2/2002 |
| JP | 2002095494 A | 4/2002 |
| JP | 2003070494 A | 3/2003 |
| JP | 2003250570 A | 9/2003 |
| JP | 2010031037 A | 2/2010 |
| RU | 2628298 C2 | 8/2017 |
| WO | 2014155291 A1 | 10/2014 |
| WO | 2020014046 A1 | 1/2020 |
| WO | 2020014047 A1 | 1/2020 |
| WO | 2020014048 A1 | 1/2020 |
| WO | 2020014050 A1 | 1/2020 |

OTHER PUBLICATIONS

Belikov, V.G., Pharmaceutical Chemistry, Moscow MEDpress-inform, 2007, 27-29, 4th Edition.
Dean, Stephen M. et al., Recent Advances in Aldolase-Catalyzed Asymmetric Synthesis, Adv. Synth. Catal., 2007, 1308-1320, 349.
Fukuyama, K., et al, "Synthesis Of EFdA Via A Diastereoselective Aldol Reaction Of A Protected 3-Keto Furanose", Organic Letters, 2015, pp. 828-831, vol. 17, No. 4.
Hattori, S., et al, "Potent Activity Of A Nucleoside Reverse Transcriptase Inhibitor", Antimicrobial Agents and Chemotherapy, 2009, pp. 3887-3893, vol. 53.
Huffman, Mark A. et al., Design of an in vitro biocatalytic cascade for the manufacture of islatravir, Science, 2019, 1255-1259, 366.
Kageyama, M., et al, "Concise Synthesis Of The Anti-HIV Nucleoside EFdA", Biosci. Biotechnol. Biochem., 2012, pp. 1219-1225, vol. 76 No. 6.
Kageyama, M., et al, "Enantioselective Total Synthesis Of The Potent Anti-HIV Nucleoside EFdA", Organic Letters, 2011, pp. 5264-5266, vol. 13, No. 19.
Kawamoto, A., et al, "2'-Deoxy-4'-C-Ethynyl-2-Halo-Adenosines Active Against Drug-Resistant Human Immunodeficiency Virus 1 Variants", Interational Journal of Biochemistry Cell Biology, 2008, pp. 2410-2420, vol. 40, No. 11.

(Continued)

*Primary Examiner* — Robert J Yamasaki
*Assistant Examiner* — Charles Zoltan Constantine
(74) *Attorney, Agent, or Firm* — Eric Greenwald; John C. Todaro

(57) ABSTRACT

The present invention relates to an enzymatic synthesis of 4'-ethynyl-2'-deoxy nucleosides and analogs thereof, for example EFdA, that eliminates the use of protecting groups on the intermediates, improves the stereoselectivity of glycosylation and reduces the number of process steps needed to make said compounds. It also relates to the novel intermediates employed in the process.

27 Claims, No Drawings

Specification includes a Sequence Listing.

(56) References Cited

OTHER PUBLICATIONS

Kohgo, S., et al.,, "Design, Efficient Synthesis, and Anti-HIV Activity of 4'-C-Cyano- and 4'-C-Ethynyl-2'-Deoxy Purine Nucleosides", Nucleosides, Nucleotides & Nucleic Acids, 2004, pp. 671-690, vol. 23, No. 4.

McLaughlin, Mark, Enantioselective Synthesis of 4'-Ethynyl-2-fluoro-2'-deoxyadenosine (EFdA) via Enzymatic Desymmetrization, Organic Letters, 2017, 926-929, 19.

Michailidis, E., et al, "4'-Ethynyl-2-Fluoro-2'-Deoxyadenosine (EFdA) Inhibits HIV-1 Reverse Transcriptase With Multiple Mechanisms", Journal of Biological Chemistry, 2014, pp. 24533-24548, vol. 289, No. 35.

Michailidis, E., et al, "Mechanism Of Inhibition Of HIV-1 Transcriptase By 4'-Ethynyl-2-Fluoro-2'-Deoxyadenosine Triphosphate, A Translocation-Defective reverse Transcriptase Ihibitor", Journal of Biological Chemistry, 2009, pp. 35681-35691, vol. 284, No. 51.

Mikhailopulo, I.A. et al., New Trends in Nucleoside Biotechnology, Acta Naturae, 2010, 36-58, 2.

Ohrui, H., et al, 2'-Deoxy-4'-C-Ethynyl-2-Fluoroadenosine: A Nucleoside, Nucleosides, Nucleotides & Nucleic Acids, 2007, pp. 1543-1546, vol. 26.

Ouwerkerk, N. et al., One-Pot Two-Step Enzymatic Coupling of Pyrimidine Bases to 2-Deoxy-D-ribose-5-phosphate. A New Strategy in the Synthesis of Stable Isotope Labeled Deoxynucleosides, J. Org. Chem., 2002, 1480-1489, 67.

Patel, Niki R. et al., Synthesis of Islatravir Enabled by a Catalytic, Enantioselective Alkynylation of a Ketone, Organic Letters, 2020, 4659-4664, 22.

Pubchem CID 87452564 Create Date: Feb. 12, 2015, Date Accessed: Sep. 12, 2019; p. 1-6.

Stoddart, C.A., et al, "Oral Administration Of The Nucleoside EFdA (4'-Ethynyl-2-Fluoro-2'-Deoxyadenosine) Provides Rapid Suppression Of HIV Viremia In Humanized Mice And Favorable Pharmacokinetic Properties In Mice And The Rhesus Macaque", Antimicrobial Agents and Chemotherapy, 2015, pp. 4190-4198, vol. 59, No. 7.

SEQUENCE LISTING

<160> NUMBER OF SEQ ID NOS: 21

<210> SEQ ID NO 1
<211> LENGTH: 657
<212> TYPE: PRT
<213> ORGANISM: Fusarium graminearum

<400> SEQUENCE: 1

```
Met Ala Ser Ala Pro Ile Gly Ser Ala Ile Pro Arg Asn Asn Trp Ala
1               5                   10                  15

Val Thr Cys Asp Ser Ala Gln Ser Gly Asn Glu Cys Asn Lys Ala Ile
                20                  25                  30

Asp Gly Asn Lys Asp Thr Phe Trp His Thr Phe Tyr Gly Ala Asn Gly
            35                  40                  45

Asp Pro Lys Pro Pro His Thr Tyr Thr Ile Asp Met Lys Thr Thr Gln
        50                  55                  60

Asn Val Asn Gly Leu Ser Val Leu Pro Arg Gln Asp Gly Asn Gln Asn
65                  70                  75                  80

Gly Trp Ile Gly Arg His Glu Val Tyr Leu Ser Ser Asp Gly Thr Asn
                85                  90                  95

Trp Gly Ser Pro Val Ala Ser Gly Ser Trp Phe Ala Asp Ser Thr Thr
            100                 105                 110

Lys Tyr Ser Asn Phe Glu Thr Arg Pro Ala Arg Tyr Val Arg Leu Val
        115                 120                 125

Ala Ile Thr Glu Ala Asn Gly Gln Pro Trp Thr Ser Ile Ala Glu Ile
    130                 135                 140

Asn Val Phe Gln Ala Ser Ser Tyr Thr Ala Pro Gln Pro Gly Leu Gly
145                 150                 155                 160

Arg Trp Gly Pro Thr Ile Asp Leu Pro Ile Val Pro Ala Ala Ala Ala
                165                 170                 175

Ile Glu Pro Thr Ser Gly Arg Val Leu Met Trp Ser Ser Tyr Arg Asn
            180                 185                 190

Asp Ala Phe Glu Gly Ser Pro Gly Gly Ile Thr Leu Thr Ser Ser Trp
        195                 200                 205

Asp Pro Ser Thr Gly Ile Val Ser Asp Arg Thr Ser Thr Val Thr Lys
    210                 215                 220

His Asp Met Phe Cys Pro Gly Ile Ser Met Asp Gly Asn Gly Gln Ile
225                 230                 235                 240

Val Val Asp Glu Thr Ala Thr Gly Gly Asn Asp Ala Lys Lys Thr Ser
                245                 250                 255

Leu Tyr Asp Ser Ser Ser Asp Ser Trp Ile Pro Gly Pro Asp Met Gln
            260                 265                 270

Val Ala Arg Gly Tyr Gln Ser Ser Ala Thr Met Ser Asp Gly Arg Val
        275                 280                 285
```

Phe Thr Ile Gly Gly Ser Phe Ser Gly Gly Arg Val Glu Lys Asn Gly
            290                 295                 300

Glu Val Tyr Ser Pro Ser Ser Lys Thr Trp Thr Ser Leu Pro Asn Ala
305                 310                 315                 320

Lys Val Asn Pro Met Leu Thr Ala Asp Lys Gln Gly Leu Tyr Arg Ser
                325                 330                 335

Asp Asn His Ala Trp Leu Phe Gly Trp Lys Lys Gly Ser Val Phe Gln
            340                 345                 350

Ala Gly Pro Ser Thr Ala Met Asn Trp Tyr Tyr Thr Ser Gly Ser Gly
        355                 360                 365

Asp Val Lys Ser Ala Gly Lys Arg Gln Ser Asn Arg Gly Val Ala Pro
370                 375                 380

Asp Ala Met Cys Gly Asn Ala Val Met Tyr Asp Ala Val Lys Gly Lys
385                 390                 395                 400

Ile Leu Thr Phe Gly Gly Ser Pro Asp Tyr Glu Asp Ser Asp Ala Thr
                405                 410                 415

Thr Asn Ala His Ile Ile Thr Leu Gly Glu Pro Gly Thr Ser Pro Asn
            420                 425                 430

Thr Val Phe Ala Ser Asn Gly Leu Tyr Phe Ala Arg Thr Phe His Thr
        435                 440                 445

Ser Val Val Leu Pro Asp Gly Ser Thr Phe Ile Thr Gly Gly Gln Arg
450                 455                 460

Arg Gly Ile Pro Thr Glu Asp Ser Thr Pro Val Phe Thr Pro Glu Ile
465                 470                 475                 480

Tyr Val Pro Glu Gln Asp Thr Phe Tyr Lys Gln Asn Pro Asn Ser Ile
                485                 490                 495

Val Arg Ala Tyr His Ser Ile Ser Leu Leu Leu Pro Asp Gly Arg Val
            500                 505                 510

Phe Asn Gly Gly Gly Gly Leu Cys Gly Asp Cys Thr Thr Asn His Phe
        515                 520                 525

Asp Ala Gln Ile Phe Thr Pro Asn Tyr Leu Tyr Asp Ser Asn Gly Asn
530                 535                 540

Leu Ala Thr Arg Pro Lys Ile Thr Arg Thr Ser Thr Gln Ser Val Lys
545                 550                 555                 560

Val Gly Gly Arg Ile Thr Ile Ser Thr Asp Ser Ser Ile Ser Lys Ala
                565                 570                 575

Ser Leu Ile Arg Tyr Gly Thr Ala Thr His Thr Val Asn Thr Asp Gln
            580                 585                 590

Arg Arg Ile Pro Leu Thr Leu Thr Asn Asn Gly Gly Asn Ser Tyr Ser
        595                 600                 605

Phe Gln Val Pro Ser Asp Ser Gly Val Ala Leu Pro Gly Tyr Trp Met
610                 615                 620

Leu Phe Val Met Asn Ser Ala Gly Val Pro Ser Val Ala Ser Thr Ile
625                 630                 635                 640

Arg Val Thr Gln Gly Gly Gly Ser Trp Ser His Pro Gln Phe Glu
                645                 650                 655

Lys

<210> SEQ ID NO 2
<211> LENGTH: 316
<212> TYPE: PRT
<213> ORGANISM: Escherichia coli

<400> SEQUENCE: 2

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
50                  55                  60

Tyr Ile Ser Ser Asn Leu Arg Arg Gln Ala Val Leu Glu Gln Phe Leu
65              70                  75                  80

Gly Thr Asn Gly Gln Arg Ile Pro Tyr Ile Ser Ile Ala Gly Ser
                85                  90                  95

Val Ala Val Gly Lys Ser Thr Thr Ala Arg Val Leu Gln Ala Leu Leu
                100                 105                 110

Ser Arg Trp Pro Glu His Arg Arg Val Glu Leu Ile Thr Thr Asp Gly
            115                 120                 125

Phe Leu His Pro Asn Gln Val Leu Lys Glu Arg Gly Leu Met Lys Lys
        130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
290                 295                 300

Ala Asn His Ala Val Glu Val Arg Leu Arg Lys
305                 310                 315

<210> SEQ ID NO 3
<211> LENGTH: 413
<212> TYPE: PRT
<213> ORGANISM: Thermotoga maritima

<400> SEQUENCE: 3

Met Gly Ser His His His His His His Gly Ser Arg Val Leu Val Ile
1               5                   10                  15

Asn Ser Gly Ser Ser Ile Lys Tyr Gln Leu Ile Glu Met Glu Gly
            20                  25                  30

Glu Lys Val Leu Cys Lys Gly Ile Ala Glu Arg Ile Gly Ile Glu Gly
        35                  40                  45

Ser Arg Leu Val His Arg Val Gly Asp Glu Lys His Val Ile Glu Arg
```

```
            50                  55                  60
Glu Leu Pro Asp His Glu Ala Leu Lys Leu Ile Leu Asn Thr Leu
 65                  70                  75                  80

Val Asp Glu Lys Leu Gly Val Ile Lys Asp Leu Lys Glu Ile Asp Ala
                 85                  90                  95

Val Gly His Arg Val Val His Gly Gly Glu Arg Phe Lys Glu Ser Val
                100                 105                 110

Leu Val Asp Glu Glu Val Leu Lys Ala Ile Glu Glu Val Ser Pro Leu
            115                 120                 125

Ala Pro Leu His Asn Pro Ala Asn Leu Met Gly Ile Lys Ala Ala Met
130                 135                 140

Lys Leu Leu Pro Gly Val Pro Asn Val Ala Val Phe Asp Thr Ala Phe
145                 150                 155                 160

His Gln Thr Ile Pro Gln Lys Ala Tyr Leu Tyr Ala Ile Pro Tyr Glu
                165                 170                 175

Tyr Tyr Glu Lys Tyr Lys Ile Arg Arg Tyr Gly Phe His Gly Thr Ser
                180                 185                 190

His Arg Tyr Val Ser Lys Arg Ala Ala Glu Ile Leu Gly Lys Lys Leu
            195                 200                 205

Glu Glu Leu Lys Ile Ile Thr Cys His Ile Gly Asn Gly Ala Ser Val
210                 215                 220

Ala Ala Val Lys Tyr Gly Lys Cys Val Asp Thr Ser Met Gly Phe Thr
225                 230                 235                 240

Pro Leu Glu Gly Leu Val Met Gly Thr Arg Ser Gly Asp Leu Asp Pro
                245                 250                 255

Ala Ile Pro Phe Phe Ile Met Glu Lys Glu Gly Ile Ser Pro Gln Glu
                260                 265                 270

Met Tyr Asp Ile Leu Asn Lys Lys Ser Gly Val Tyr Gly Leu Ser Lys
            275                 280                 285

Gly Phe Ser Ser Asp Met Arg Asp Ile Glu Glu Ala Ala Leu Lys Gly
290                 295                 300

Asp Glu Trp Cys Lys Leu Val Leu Glu Ile Tyr Asp Tyr Arg Ile Ala
305                 310                 315                 320

Lys Tyr Ile Gly Ala Tyr Ala Ala Met Asn Gly Val Asp Ala Ile
                325                 330                 335

Val Phe Thr Ala Gly Val Gly Glu Asn Ser Pro Ile Thr Arg Glu Asp
            340                 345                 350

Val Cys Ser Tyr Leu Glu Phe Leu Gly Val Lys Leu Asp Lys Gln Lys
            355                 360                 365

Asn Glu Glu Thr Ile Arg Gly Lys Gly Ile Ile Ser Thr Pro Asp
370                 375                 380

Ser Arg Val Lys Val Leu Val Val Pro Thr Asn Glu Glu Leu Met Ile
385                 390                 395                 400

Ala Arg Asp Thr Lys Glu Ile Val Glu Lys Ile Gly Arg
                405                 410

<210> SEQ ID NO 4
<211> LENGTH: 613
<212> TYPE: PRT
<213> ORGANISM: Streptococcus thermophilus

<400> SEQUENCE: 4

Met Gly Ser Ser His His His His His His Ser Ser Gly Leu Val Pro
 1               5                   10                  15
```

```
Arg Gly Ser His Met Thr Val Gly Lys Thr Lys Val Ser Thr Ala Ser
            20                  25                  30

Leu Lys Val Leu Ala Gly Trp Gly Ile Asp Thr Ile Tyr Gly Ile Pro
        35                  40                  45

Ser Gly Thr Leu Ala Pro Leu Met Glu Ala Leu Gly Glu Gln Glu Glu
    50                  55                  60

Thr Asp Ile Lys Phe Leu Gln Val Lys His Glu Glu Val Gly Ala Met
65                  70                  75                  80

Ala Ala Val Met Gln Trp Lys Phe Gly Gly Lys Leu Gly Val Cys Val
                85                  90                  95

Gly Ser Gly Gly Pro Gly Ala Ser His Leu Ile Asn Gly Leu Tyr Asp
            100                 105                 110

Ala Ala Met Asp Asn Thr Pro Val Leu Ala Ile Leu Gly Ser Pro Pro
        115                 120                 125

Gln Arg Glu Leu Asn Met Asp Ala Phe Gln Glu Leu Asn Gln Asn Pro
    130                 135                 140

Met Tyr Asp His Ile Ala Val Tyr Asn Arg Arg Val Ala Tyr Ala Glu
145                 150                 155                 160

Gln Leu Pro Lys Leu Ile Asp Asp Ala Ile Arg Thr Ala Ile Ser Lys
                165                 170                 175

Arg Gly Val Ala Val Leu Glu Val Pro Gly Asp Phe Gly Tyr Lys Glu
            180                 185                 190

Ile Ala Asn Asp Ala Phe Tyr Ser Ser Gly His Ser Tyr Arg Asp Tyr
        195                 200                 205

Val Ser Ser Ala Ile Asn Glu Val Asp Ile Asp Ala Ala Val Glu Val
    210                 215                 220

Leu Asn Lys Ser Lys Arg Ala Val Ile Tyr Ala Gly Ile Gly Thr Met
225                 230                 235                 240

Gly His Gly Pro Ala Val Gln Glu Leu Ser Arg Lys Ile Lys Ala Pro
                245                 250                 255

Ile Ile Thr Thr Ala Lys Asn Phe Glu Thr Phe Asp Tyr Asp Phe Glu
            260                 265                 270

Gly Leu Thr Gly Ser Thr Tyr Arg Val Gly Trp Lys Pro Ala Asn Glu
        275                 280                 285

Ala Val Lys Glu Ala Asp Thr Val Leu Phe Val Gly Ser Asn Phe Pro
    290                 295                 300

Phe Ala Glu Val Glu Gly Thr Phe Ser Asn Val Glu Asn Phe Ile Gln
305                 310                 315                 320

Ile Asp Asn Asn Pro Thr Met Leu Gly Lys Arg His Asn Ala Asp Val
                325                 330                 335

Ala Ile Leu Gly Asp Ala Gly Glu Ala Val Gln Met Leu Leu Glu Lys
            340                 345                 350

Val Ala Pro Val Glu Glu Ser Ala Trp Trp Asn Ala Asn Leu Lys Asn
        355                 360                 365

Ile Gln Asn Trp Arg Asp Tyr Met Thr Lys Leu Glu Thr Lys Glu Asn
    370                 375                 380

Gly Pro Leu Gln Leu Tyr Gln Val Tyr Asn Ala Ile Asn Lys Tyr Ala
385                 390                 395                 400

Asp Glu Asp Ala Ile Tyr Ser Ile Asp Val Gly Asn Thr Thr Gln Thr
                405                 410                 415

Ser Ile Arg His Leu His Met Thr Pro Lys Asn Met Trp Arg Thr Ser
            420                 425                 430

Pro Leu Phe Ala Ser Met Gly Ile Ala Leu Pro Gly Gly Ile Gly Ala
```

435                 440                 445
Lys Asn Val Tyr Pro Glu Arg Gln Val Phe Asn Leu Met Gly Asp Gly
    450                 455                 460

Ala Phe Ser Met Asn Tyr Gln Asp Ile Val Thr Asn Val Arg Tyr Asn
465                 470                 475                 480

Met Pro Val Ile Asn Val Val Phe Thr Asn Thr Glu Tyr Gly Phe Ile
                485                 490                 495

Lys Asn Lys Tyr Glu Asp Thr Asn Thr Asn Thr Phe Gly Thr Glu Phe
            500                 505                 510

Thr Asp Val Asp Tyr Ala Met Ile Gly Glu Ala Gln Gly Ala Val Gly
        515                 520                 525

Phe Thr Val Ser Arg Ile Glu Asp Met Asp Gln Val Met Ala Ala Ala
    530                 535                 540

Val Lys Ala Asn Lys Glu Gly Lys Thr Val Val Ile Asp Ala Lys Ile
545                 550                 555                 560

Thr Lys Asp Arg Pro Ile Pro Val Glu Thr Leu Lys Leu Asp Pro Ala
                565                 570                 575

Leu Tyr Ser Glu Glu Glu Ile Lys Ala Tyr Lys Glu Arg Tyr Glu Ala
            580                 585                 590

Glu Glu Leu Val Pro Phe Ser Glu Phe Leu Lys Ala Glu Gly Leu Glu
        595                 600                 605

Ser Lys Val Ala Lys
    610

<210> SEQ ID NO 5
<211> LENGTH: 257
<212> TYPE: PRT
<213> ORGANISM: Shewanella halifaxensis

<400> SEQUENCE: 5

Met Ser Asp Leu Lys Lys Ala Ala Gln Gln Ala Ile Ser Leu Met Asp
1               5                   10                  15

Leu Thr Thr Leu Asn Asp Asp Thr Asp Gln Lys Val Ile Glu Leu
            20                  25                  30

Cys His Lys Ala Lys Thr Pro Ala Gly Asp Thr Ala Ala Ile Cys Ile
        35                  40                  45

Tyr Pro Arg Phe Ile Pro Ile Ala Arg Lys Thr Leu Asn Glu Ile Gly
    50                  55                  60

Gly Asp Asp Ile Lys Ile Ala Thr Val Thr Asn Phe Pro His Gly Asn
65                  70                  75                  80

Asp Asp Ile Ala Ile Ala Val Leu Glu Thr Arg Ala Ala Val Ala Tyr
                85                  90                  95

Gly Ala Asp Glu Val Asp Val Val Phe Pro Tyr Arg Ala Leu Met Glu
            100                 105                 110

Gly Asn Glu Thr Val Gly Phe Glu Leu Val Lys Ala Cys Lys Glu Ala
        115                 120                 125

Cys Gly Glu Asp Thr Ile Leu Lys Val Ile Glu Ser Gly Val Leu
    130                 135                 140

Ala Asp Pro Ala Leu Ile Arg Lys Ala Ser Glu Leu Ser Ile Asp Ala
145                 150                 155                 160

Gly Ala Asp Phe Ile Lys Thr Ser Thr Gly Lys Val Ala Val Asn Ala
                165                 170                 175

Thr Leu Glu Ala Ala Glu Ile Met Met Thr Val Ile Ser Glu Lys Asn
            180                 185                 190

Pro Lys Val Gly Phe Lys Pro Ala Gly Val Lys Asp Ala Ala Ala
            195                 200                 205

Ala Ala Glu Phe Leu Gly Val Ala Ala Arg Leu Leu Gly Asp Asp Trp
    210                 215                 220

Ala Thr Pro Ala Thr Phe Arg Phe Gly Ala Ser Ser Leu Leu Thr Asn
225                 230                 235                 240

Leu Leu His Thr Leu Glu Leu Ala Asp Ala Pro Gln Gly Ala Gln Gly
                245                 250                 255

Tyr

<210> SEQ ID NO 6
<211> LENGTH: 257
<212> TYPE: PRT
<213> ORGANISM: Shewanella halifaxensis

<400> SEQUENCE: 6

Met Cys Asp Leu Lys Lys Ala Ala Gln Arg Ala Ile Ser Leu Met Asp
1               5                   10                  15

Leu Thr Thr Leu Asn Asp Asp Thr Asp Gln Lys Val Ile Glu Leu
            20                  25                  30

Cys His Lys Ala Lys Thr Pro Ala Gly Asp Thr Ala Ala Ile Val Ile
            35                  40                  45

Tyr Pro Arg Phe Ile Pro Ile Ala Arg Lys Thr Leu Asn Glu Ile Gly
    50                  55                  60

Gly Leu Asp Ile Lys Ile Val Thr Val Thr Asn Phe Pro His Gly Asn
65                  70                  75                  80

Asp Asp Ile Ala Ile Ala Val Leu Glu Thr Arg Ala Ala Val Ala Tyr
                85                  90                  95

Gly Ala Asp Glu Val Asp Val Val Phe Pro Tyr Arg Ala Leu Met Glu
            100                 105                 110

Gly Asn Glu Thr Val Gly Phe Glu Leu Val Lys Ala Cys Lys Glu Ala
        115                 120                 125

Cys Gly Glu Asp Thr Ile Leu Lys Val Ile Glu Ser Gly Val Leu
130                 135                 140

Lys Asp Pro Ala Leu Ile Arg Lys Ala Ser Glu Ile Ser Ile Asp Ala
145                 150                 155                 160

Gly Ala Asp Phe Ile Lys Thr Ser Thr Gly Lys Val Ala Val Asn Ala
                165                 170                 175

Thr Leu Glu Ala Ala Glu Ile Ile Met Thr Val Ile Ser Glu Lys Asn
            180                 185                 190

Pro Lys Val Gly Phe Lys Pro Ala Gly Gly Ile Lys Asp Ala Ala Ala
        195                 200                 205

Ala Ala Glu Phe Leu Gly Val Ala Ala Arg Leu Leu Gly Asp Asp Trp
    210                 215                 220

Ala Thr Pro Ala Thr Phe Arg Phe Gly Ala Thr Asp Leu Leu Thr Asn
225                 230                 235                 240

Leu Leu His Thr Leu Glu Leu Ala Asp Ala Pro Gln Gly Ala Gln Gly
                245                 250                 255

Tyr

<210> SEQ ID NO 7
<211> LENGTH: 500
<212> TYPE: PRT
<213> ORGANISM: Alloscardovia omnicolens

<400> SEQUENCE: 7

```
Met Lys Asn Lys Val Gln Leu Ile Thr Tyr Ala Asp Arg Leu Gly Asp
1               5                   10                  15
Gly Thr Leu Lys Ser Met Thr Glu Thr Leu Arg Lys His Phe Glu Gly
            20                  25                  30
Val Tyr Glu Gly Val His Ile Leu Pro Phe Phe Thr Pro Phe Asp Gly
        35                  40                  45
Ala Asp Ala Gly Phe Asp Pro Val Asp His Thr Lys Val Asp Pro Arg
    50                  55                  60
Leu Gly Ser Trp Asp Asp Val Ala Glu Leu Ser Thr Thr His Asp Ile
65                  70                  75                  80
Met Val Asp Thr Ile Val Asn His Met Ser Trp Glu Ser Glu Gln Phe
                85                  90                  95
Gln Asp Val Met Ala Lys Gly Glu Asp Ser Glu Tyr Tyr Pro Met Phe
            100                 105                 110
Leu Thr Met Ser Ser Ile Phe Pro Asp Gly Val Thr Glu Glu Asp Leu
        115                 120                 125
Thr Ala Ile Tyr Arg Pro Arg Pro Gly Leu Pro Phe Thr His Tyr Asn
    130                 135                 140
Trp Gly Gly Lys Thr Arg Leu Val Trp Thr Thr Phe Thr Pro Gln Gln
145                 150                 155                 160
Val Asp Ile Asp Thr Asp Ser Glu Met Gly Trp Asn Tyr Leu Leu Ser
                165                 170                 175
Ile Leu Asp Gln Leu Ser Gln Ser His Val Ser Gln Ile Arg Leu Asp
            180                 185                 190
Ala Val Gly Tyr Gly Ala Lys Glu Lys Asn Ser Ser Cys Phe Met Thr
        195                 200                 205
Pro Lys Thr Phe Lys Leu Ile Glu Arg Ile Lys Ala Glu Gly Glu Lys
    210                 215                 220
Arg Gly Leu Glu Thr Leu Ile Glu Val His Ser Tyr Tyr Lys Lys Gln
225                 230                 235                 240
Val Glu Ile Ala Ser Lys Val Asp Arg Val Tyr Asp Phe Ala Ile Pro
                245                 250                 255
Gly Leu Leu Leu His Ala Leu Glu Phe Gly Lys Thr Asp Ala Leu Ala
            260                 265                 270
Gln Trp Ile Asp Val Arg Pro Asn Asn Ala Val Asn Val Leu Asp Thr
        275                 280                 285
His Asp Gly Ile Gly Val Ile Asp Ile Gly Ser Asp Gln Met Asp Arg
    290                 295                 300
Ser Leu Ala Gly Leu Val Pro Asp Glu Val Asp Ala Leu Val Glu
305                 310                 315                 320
Ser Ile His Arg Asn Ser Lys Gly Glu Ser Gln Glu Ala Thr Gly Ala
                325                 330                 335
Ala Ala Ser Asn Leu Asp Leu Tyr Gln Val Asn Cys Thr Tyr Tyr Ala
            340                 345                 350
Ala Leu Gly Ser Asp Asp Gln Lys Tyr Ile Ala Ala Arg Ala Val Gln
        355                 360                 365
Phe Phe Met Pro Gly Val Pro Gln Val Tyr Tyr Val Gly Ala Leu Ala
    370                 375                 380
Gly Ser Asn Asp Met Asp Leu Leu Lys Arg Thr Asn Val Gly Arg Asp
385                 390                 395                 400
Ile Asn Arg His Tyr Tyr Ser Ala Ala Glu Val Ala Ser Glu Val Glu
                405                 410                 415
```

```
Arg Pro Val Val Gln Ala Leu Asn Ala Leu Gly Arg Phe Arg Asn Thr
            420                 425                 430

Leu Ser Ala Phe Asp Gly Glu Phe Ser Tyr Ser Asn Ala Asp Gly Val
        435                 440                 445

Leu Thr Met Thr Trp Ala Asp Asp Ala Thr Arg Ala Thr Leu Thr Phe
    450                 455                 460

Ala Pro Lys Ala Asn Ser Asn Gly Ala Ser Val Ala Arg Leu Glu Trp
465                 470                 475                 480

Thr Asp Ala Ala Gly Glu His Ala Thr Asp Asp Leu Ile Ala Asn Pro
                485                 490                 495

Pro Val Val Ala
        500

<210> SEQ ID NO 8
<211> LENGTH: 407
<212> TYPE: PRT
<213> ORGANISM: Escherichia coli

<400> SEQUENCE: 8

Met Lys Arg Ala Phe Ile Met Val Leu Asp Ser Phe Gly Ile Gly Ala
1               5                   10                  15

Thr Glu Asp Ala Glu Arg Phe Gly Asp Val Gly Ala Asp Thr Leu Gly
            20                  25                  30

His Ile Ala Glu Ala Cys Ala Lys Gly Glu Ala Asp Asn Gly Arg Lys
        35                  40                  45

Gly Pro Leu Asn Leu Pro Asn Leu Thr Arg Leu Gly Leu Ala Lys Ala
    50                  55                  60

His Glu Gly Ser Thr Gly Phe Ile Pro Ala Gly Met Asp Gly Asn Ala
65                  70                  75                  80

Glu Val Ile Gly Ala Tyr Ala Trp Ala His Glu Met Ser Ser Gly Lys
                85                  90                  95

Asp Ser Val Ser Gly His Trp Glu Ile Ala Gly Val Pro Val Leu Phe
            100                 105                 110

Glu Trp Gly Tyr Phe Ser Asp His Glu Asn Ser Phe Pro Gln Glu Leu
        115                 120                 125

Leu Asp Lys Leu Val Glu Arg Ala Asn Leu Pro Gly Tyr Leu Gly Asn
    130                 135                 140

Cys Arg Ser Ser Gly Thr Val Ile Leu Asp Gln Leu Gly Glu Glu His
145                 150                 155                 160

Met Lys Thr Gly Lys Pro Ile Phe Tyr Thr Ser Ala Ala Ser Val Phe
                165                 170                 175

Gln Ile Ala Cys His Glu Glu Thr Phe Gly Leu Asp Lys Leu Tyr Glu
            180                 185                 190

Leu Cys Glu Ile Ala Arg Glu Leu Thr Asn Gly Gly Tyr Asn Ile
        195                 200                 205

Gly Arg Val Ile Ala Arg Pro Phe Ile Gly Asp Lys Ala Gly Asn Phe
    210                 215                 220

Gln Arg Thr Gly Asn Arg Arg Asp Leu Ala Val Glu Pro Pro Ala Pro
225                 230                 235                 240

Thr Val Leu Gln Lys Leu Val Asp Glu Lys His Gly Gln Val Val Ser
                245                 250                 255

Val Gly Lys Ile Ala Asp Ile Tyr Ala Asn Cys Gly Ile Thr Lys Lys
            260                 265                 270

Val Lys Ala Thr Gly Leu Asp Ala Leu Phe Asp Ala Thr Ile Lys Glu
        275                 280                 285
```

```
Met Lys Glu Ala Gly Asp Asn Thr Ile Val Phe Thr Asn Phe Val Asp
            290                 295                 300

Phe Asp Ser Ser Trp Gly His Arg Arg Asp Val Ala Gly Tyr Ala Ala
305                 310                 315                 320

Gly Leu Glu Leu Phe Asp Arg Arg Leu Pro Glu Leu Met Ser Leu Leu
                325                 330                 335

Arg Asp Asp Asp Ile Leu Ile Leu Thr Ala Asp His Gly Cys Asp Pro
            340                 345                 350

Thr Trp Thr Gly Thr Asp His Thr Arg Glu His Ile Pro Val Leu Val
                355                 360                 365

Tyr Gly Pro Lys Val Lys Pro Gly Ser Leu Gly His Arg Glu Thr Phe
    370                 375                 380

Ala Asp Ile Gly Gln Thr Leu Ala Lys Tyr Phe Gly Thr Ser Asp Met
385                 390                 395                 400

Glu Tyr Gly Lys Ala Met Phe
                405

<210> SEQ ID NO 9
<211> LENGTH: 239
<212> TYPE: PRT
<213> ORGANISM: Escherichia coli

<400> SEQUENCE: 9

Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Ala Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

<210> SEQ ID NO 10
<211> LENGTH: 650
<212> TYPE: PRT
<213> ORGANISM: Fusarium graminearum

<400> SEQUENCE: 10

```
Met Ala Ser Ala Pro Ile Gly Val Ala Ile Pro Arg Asn Asn Trp Ala
1               5                   10                  15

Val Thr Cys Asp Ser Ala Gln Ser Gly Asn Glu Cys Asn Lys Ala Ile
            20                  25                  30

Asp Gly Asn Lys Asp Thr Phe Trp His Thr Gln Tyr Gly Val Asn Gly
        35                  40                  45

Asp Pro Lys Pro Pro His Thr Ile Thr Ile Asp Met Lys Thr Val Gln
    50                  55                  60

Asn Val Asn Gly Leu Ser Val Leu Pro Arg Gln Asp Gly Asn Gln Asn
65                  70                  75                  80

Gly Trp Ile Gly Arg His Glu Val Tyr Leu Ser Ser Asp Gly Val Asn
                85                  90                  95

Trp Gly Ser Pro Val Ala Ser Gly Ser Trp Phe Ala Asp Ser Thr Thr
            100                 105                 110

Lys Tyr Ser Asn Phe Glu Thr Arg Pro Ala Arg Tyr Val Arg Leu Val
        115                 120                 125

Ala Ile Thr Glu Ala Asn Gly Gln Pro Trp Thr Ser Ile Ala Glu Ile
    130                 135                 140

Asn Val Phe Gln Ala Ser Ser Tyr Thr Ala Pro Gln Pro Gly Leu Gly
145                 150                 155                 160

Arg Trp Gly Pro Thr Ile Asp Leu Pro Ile Val Pro Ser Ala Ala Ala
                165                 170                 175

Ile Glu Pro Thr Ser Gly Arg Val Leu Met Trp Ser Ser Tyr Arg Gln
            180                 185                 190

Asp Ala Phe Glu Gly Ser Pro Gly Gly Ile Thr Leu Thr Ser Ser Trp
        195                 200                 205

Asp Pro Ser Thr Gly Ile Val Ser Asp Arg Thr Ser Thr Val Thr Lys
    210                 215                 220

His Asp Met Phe Cys Pro Gly Ile Ser Met Asp Gly Asn Gly Gln Ile
225                 230                 235                 240

Val Val Ser Gly Gly Asn Asp Ala Lys Lys Thr Ser Leu Tyr Asp Ser
                245                 250                 255

Ser Ser Asp Ser Trp Ile Pro Gly Pro Asp Met Gln Val Ala Arg Gly
            260                 265                 270

Tyr Gln Ser Ser Ala Thr Met Ser Asp Gly Arg Val Phe Thr Ile Gly
        275                 280                 285

Gly Ser Phe Ser Gly Gly Gln Val Glu Lys Asn Gly Glu Val Tyr Ser
    290                 295                 300

Pro Ser Ser Lys Thr Trp Thr Ser Leu Pro Asn Ala Lys Val Asn Pro
305                 310                 315                 320

Met Leu Thr Ala Asp Lys Gln Gly Leu Tyr Arg Ser Asp Asn His Ala
                325                 330                 335

Trp Leu Phe Gly Trp Lys Lys Gly Ser Val Phe Gln Ala Gly Pro Ser
            340                 345                 350

Thr Ala Met Asn Trp Tyr Tyr Thr Ser Gly Ser Gly Asp Val Lys Ser
        355                 360                 365

Ala Gly Lys Arg Gln Ser Asn Arg Gly Val Ala Pro Asp Ala Met Cys
    370                 375                 380
```

```
Gly Asn Ala Val Met Tyr Asp Ala Val Lys Gly Lys Ile Leu Thr Phe
385                 390                 395                 400

Gly Gly Ser Pro Asp Tyr Glu Asp Ser Asp Ala Thr Thr Asn Ala His
            405                 410                 415

Ile Ile Thr Leu Gly Glu Pro Gly Thr Ser Pro Asn Thr Val Phe Ala
                420                 425                 430

Ser Asn Gly Leu Tyr Phe Ala Arg Thr Phe His Thr Ser Val Val Leu
            435                 440                 445

Pro Asp Gly Ser Thr Phe Ile Thr Gly Gly Gln Gln Arg Gly Ile Pro
    450                 455                 460

Thr Glu Asp Ser Thr Pro Val Phe Thr Pro Glu Ile Tyr Val Pro Glu
465                 470                 475                 480

Gln Asp Thr Phe Tyr Lys Gln Asn Pro Asn Ser Ile Val Arg Ala Tyr
                485                 490                 495

His Ser Ile Ser Leu Leu Pro Asp Gly Arg Val Phe Asn Gly Gly
            500                 505                 510

Gly Gly Leu Cys Gly Asp Cys Thr Thr Asn His Phe Asp Ala Gln Ile
            515                 520                 525

Phe Thr Pro Asn Tyr Leu Tyr Asp Ser Asn Gly Asn Leu Ala Thr Arg
530                 535                 540

Pro Lys Ile Thr Arg Thr Ser Thr Gln Ser Val Val Gly Gly Trp
545                 550                 555                 560

Ile Thr Ile Trp Thr Asp Met Ser Ile Ser Ala Ala Ser Leu Ile Arg
                565                 570                 575

Tyr Gly Thr Ala Thr His Thr Val Asn Thr Asp Gln Arg Arg Ile Pro
            580                 585                 590

Leu Thr Leu Thr Asn Asn Gly Gly Asn Ser Tyr Ser Phe Gln Val Pro
                595                 600                 605

Ser Asp Ser Gly Val Ala Leu Pro Gly Tyr Trp Met Leu Phe Val Met
    610                 615                 620

Asn Ser Ala Gly Val Pro Ser Val Ala Ser Thr Ile Arg Val Thr Gln
625                 630                 635                 640

Gly Gln Thr Gly His His His His His
            645                 650

<210> SEQ ID NO 11
<211> LENGTH: 650
<212> TYPE: PRT
<213> ORGANISM: Fusarium graminearum

<400> SEQUENCE: 11

Met Ala Ser Ala Pro Ile Gly Val Ala Ile Pro Arg Asn Asn Trp Ala
1               5                   10                  15

Val Thr Cys Asp Ser Ala Gln Ser Gly Asn Glu Cys Asn Lys Ala Ile
                20                  25                  30

Asp Gly Asn Lys Asp Thr Phe Trp His Thr Gln Tyr Gly Val Asn Gly
            35                  40                  45

Asp Pro Lys Pro Pro His Thr Ile Thr Ile Asp Met Lys Thr Val Gln
    50                  55                  60

Asn Val Asn Gly Leu Ser Val Leu Pro Arg Gln Asp Gly Asn Gln Asn
65                  70                  75                  80

Gly Trp Ile Gly Arg His Glu Val Tyr Leu Ser Ser Asp Gly Val Asn
                85                  90                  95

Trp Gly Ser Pro Val Ala Ser Gly Ser Trp Phe Ala Asp Ser Thr Thr
                100                 105                 110
```

-continued

Lys Tyr Ser Asn Phe Glu Thr Arg Pro Ala Arg Tyr Val Arg Leu Val
            115                 120                 125

Ala Ile Thr Glu Ala Asn Gly Gln Pro Trp Thr Ser Ile Ala Glu Ile
        130                 135                 140

Asn Val Phe Gln Ala Ser Ser Tyr Thr Ala Pro Gln Pro Gly Leu Gly
145                 150                 155                 160

Arg Trp Gly Pro Thr Ile Asp Leu Pro Ile Val Pro Ser Ala Ala Ala
                165                 170                 175

Ile Glu Pro Thr Ser Gly Arg Val Leu Met Trp Ser Ser Tyr Arg Gln
                180                 185                 190

Asp Ala Phe Glu Gly Ser Pro Gly Gly Ile Thr Leu Thr Ser Ser Trp
            195                 200                 205

Asp Pro Ser Thr Gly Ile Val Ser Asp Arg Thr Ser Thr Val Thr Gly
        210                 215                 220

His Asp Met Phe Cys Pro Gly Ile Ser Met Asp Gly Asn Gly Gln Ile
225                 230                 235                 240

Val Val Ser Gly Gly Asn Asp Ala Lys Lys Thr Ser Leu Tyr Asp Ser
                245                 250                 255

Ser Ser Asp Ser Trp Ile Pro Gly Pro Asp Met Gln Val Ala Arg Gly
                260                 265                 270

Tyr Asn Ser Ser Ala Thr Met Ser Asp Gly Arg Val Phe Thr Ile Gly
            275                 280                 285

Gly Ser Phe Ser Gly Gly Gln Val Glu Lys Asn Gly Glu Val Tyr Ser
        290                 295                 300

Pro Ser Ser Lys Thr Trp Thr Ser Leu Pro Asn Ala Lys Val Asn Pro
305                 310                 315                 320

Met Leu Thr Ala Asp Lys Gln Gly Leu Tyr Arg Ser Asp Asn His Ala
                325                 330                 335

Trp Leu Phe Gly Trp Lys Lys Gly Ser Val Phe Gln Ala Gly Pro Ser
                340                 345                 350

Thr Ala Met Asn Trp Tyr Tyr Thr Ser Gly Ser Gly Asp Val Lys Ser
            355                 360                 365

Ala Gly Lys Arg Gln Ser Asn Arg Gly Val Ala Pro Asp Ala Met Cys
        370                 375                 380

Gly Asn Ala Val Met Tyr Asp Ala Val Lys Gly Lys Ile Leu Thr Phe
385                 390                 395                 400

Gly Gly Ser Pro Asp Tyr Gln Asp Ser Asp Ala Thr Thr Asn Ala His
                405                 410                 415

Ile Ile Thr Leu Gly Glu Pro Gly Thr Ser Pro Asn Thr Val Phe Ala
                420                 425                 430

Ser Asn Gly Leu Leu Phe Ala Arg Thr Phe His Thr Ser Val Val Leu
        435                 440                 445

Pro Asp Gly Ser Thr Phe Ile Thr Gly Gly Gln Gln Arg Gly Ile Pro
450                 455                 460

Thr Glu Asp Ser Thr Pro Val Phe Thr Pro Glu Ile Tyr Val Pro Glu
465                 470                 475                 480

Gln Asp Thr Phe Tyr Lys Gln Asn Pro Asn Ser Ile Val Arg Ala Tyr
                485                 490                 495

His Ser Ile Ser Leu Leu Leu Pro Asp Gly Arg Val Phe Asn Gly Gly
                500                 505                 510

Gly Gly Leu Cys Gly Asp Cys Glu Thr Asn His Phe Asp Ala Gln Ile
        515                 520                 525

```
Phe Thr Pro Asn Tyr Leu Tyr Asp Ser Asn Gly Asn Leu Ala Thr Arg
        530                 535                 540

Pro Lys Ile Thr Arg Thr Ser Thr Gln Ser Val Val Gly Gly Trp
545                 550                 555                 560

Ile Thr Ile Trp Thr Asp Met Ser Ile Ser Ala Ala Ser Leu Ile Arg
                565                 570                 575

Tyr Gly Thr Ala Thr His Thr Val Asn Thr Asp Gln Arg Arg Ile Pro
                580                 585                 590

Leu Thr Leu Thr Asn Asn Gly Gly Asn Ser Tyr Ser Phe Gln Val Pro
                595                 600                 605

Ser Asp Ser Gly Val Ala Leu Pro Gly Tyr Trp Met Leu Phe Val Met
610                 615                 620

Asn Ser Ala Gly Val Pro Ser Val Ala Ser Thr Ile Asn Val Thr Gln
625                 630                 635                 640

Gly Gln Thr Gly His His His His
                645                 650

<210> SEQ ID NO 12
<211> LENGTH: 316
<212> TYPE: PRT
<213> ORGANISM: Escherichia coli

<400> SEQUENCE: 12

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
                20                  25                  30

Glu Asp Glu Ile Ala Arg Leu Lys Gly Ile Asn Glu Asp Leu Ser Leu
            35                  40                  45

Glu Glu Val Ala Glu Val Tyr Leu Pro Leu Ser Arg Leu Leu Asn Phe
        50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
                100                 105                 110

Ser Arg Trp Pro Glu His Arg Arg Val Glu Leu Ile Thr Thr Asp Gly
            115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
                180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255
```

```
Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
            275                 280                 285

Asn Ile Leu Pro Thr Arg Glu Arg Ala Ser Leu Ile Leu Thr Lys Ser
            290                 295                 300

Ala Asn His Ile Val Glu Glu Val Arg Leu Arg Lys
305                 310                 315

<210> SEQ ID NO 13
<211> LENGTH: 325
<212> TYPE: PRT
<213> ORGANISM: Escherichia coli

<400> SEQUENCE: 13

Met His His His His His Gly Gly Met Ser Ile Lys Glu Gln Thr
1               5                   10                  15

Leu Met Thr Pro Tyr Leu Gln Leu Asp Arg Asn Gln Trp Ala Ala Leu
            20                  25                  30

Arg Asp Ser Asn Pro Met Thr Leu Ser Glu Asp Glu Ile Ala Arg Leu
            35                  40                  45

Lys Gly Ile Asn Glu Asp Leu Ser Leu Glu Glu Val Ala Glu Val Tyr
50                  55                  60

Leu Pro Leu Ser Arg Leu Leu Asn Phe Tyr Ile Ser Ser Asn Leu Arg
65                  70                  75                  80

Arg Gln Ala Val Leu Glu Gln Phe Leu Gly Thr Asn Gly Gln Arg Ile
            85                  90                  95

Pro Tyr Ile Ile Ser Ile Ala Gly Ser Val Ala Val Gly Lys Ser Thr
            100                 105                 110

Thr Ala Arg Val Leu Gln Ala Leu Leu Ser Arg Trp Pro Glu His Arg
            115                 120                 125

Arg Val Glu His Ile Thr Thr Asp Gly Phe Leu His Pro Asn Gln Val
            130                 135                 140

Leu Lys Glu Arg Gly Leu Met Gly Lys Lys Gly Phe Pro Glu Ser Tyr
145                 150                 155                 160

Asp Met His Arg Leu Met Lys Phe Val Lys Asp Leu Lys Ser Gly Val
            165                 170                 175

Pro Asn Val Thr Ala Pro Val Tyr Ser His Leu Ile Tyr Asp Val Ile
            180                 185                 190

Pro Asp Gly Asp Lys Thr Val Val Gln Pro Asp Ile Leu Ile Leu Glu
            195                 200                 205

Gly Leu Asn Val Leu Gln Ser Gly Met Asp Tyr Pro His Asp Pro His
            210                 215                 220

His Val Phe Val Ser Asp Phe Val Asp Phe Ser Ile Tyr Val Asp Ala
225                 230                 235                 240

Pro Glu Asp Leu Leu Gln Thr Trp Tyr Ile Asn Arg Phe Leu Lys Phe
            245                 250                 255

Arg Glu Gly Ala Phe Thr Asp Pro Asp Ser Tyr Phe His Gly Tyr Ala
            260                 265                 270

Lys Leu Thr Lys Glu Glu Ala Ile Lys Thr Ala Met Thr Ile Trp Lys
            275                 280                 285

Glu Met Asn His Leu Asn Leu Lys Gln Asn Ile Leu Pro Thr Arg Glu
            290                 295                 300

Arg Ala Ser Leu Ile Leu Thr Lys Ser Ala Asn His Ile Val Glu Glu
```

Val Arg Leu Arg Lys
            325

<210> SEQ ID NO 14
<211> LENGTH: 263
<212> TYPE: PRT
<213> ORGANISM: Shewanella halifaxensis

<400> SEQUENCE: 14

Met His His His His His Cys Asp Leu Lys Lys Ala Ala Gln Arg
1               5                   10                  15

Ala Ile Ser Leu Met Asp Leu Thr Thr Leu Asn Asp Asp Thr Asp
                20                  25                  30

Gln Lys Val Ile Glu Leu Cys His Lys Ala Lys Thr Pro Ala Gly Asp
            35                  40                  45

Thr Ala Ala Ile Val Ile Tyr Pro Arg Phe Ile Pro Ile Ala Arg Lys
        50                  55                  60

Thr Leu Asn Glu Ile Gly Gly Leu Asp Ile Lys Ile Val Thr Val Thr
65                  70                  75                  80

Asn Phe Pro His Gly Asn Asp Asp Ile Ala Ile Ala Val Leu Glu Thr
                85                  90                  95

Arg Ala Ala Val Ala Tyr Gly Ala Asp Glu Val Asp Val Val Phe Pro
            100                 105                 110

Tyr Arg Ala Leu Met Glu Gly Asn Glu Thr Val Gly Phe Glu Leu Val
        115                 120                 125

Lys Ala Cys Lys Glu Ala Cys Gly Glu Asp Thr Ile Leu Lys Val Ile
    130                 135                 140

Ile Glu Ser Gly Val Leu Lys Asp Pro Ala Leu Ile Arg Lys Ala Ser
145                 150                 155                 160

Glu Ile Ser Ile Asp Ala Gly Ala Asp Phe Ile Lys Thr Ser Thr Gly
                165                 170                 175

Lys Val Ala Val Asn Ala Thr Leu Glu Ala Ala Glu Ile Ile Met Thr
            180                 185                 190

Val Ile Ser Glu Lys Asn Pro Lys Val Gly Phe Lys Pro Ala Gly Gly
        195                 200                 205

Ile Lys Asp Ala Ala Ala Ala Glu Phe Leu Gly Val Ala Ala Arg
    210                 215                 220

Leu Leu Gly Asp Asp Trp Ala Thr Pro Ala Thr Phe Arg Phe Gly Ala
225                 230                 235                 240

Thr Asp Leu Leu Thr Asn Leu Leu His Thr Leu Glu Leu Ala Asp Ala
                245                 250                 255

Pro Gln Gly Ala Gln Gly Tyr
            260

<210> SEQ ID NO 15
<211> LENGTH: 239
<212> TYPE: PRT
<213> ORGANISM: Escherichia coli

<400> SEQUENCE: 15

Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly

```
            35                  40                  45
Phe Thr Gly Thr Tyr Lys Gly Arg Lys Ile Ser Val Met Gly His Gly
 50                  55                  60

Met Gly Ile Pro Ser Cys Ser Ile Tyr Thr Lys Glu Leu Ile Thr Asp
 65                  70                  75                  80

Phe Gly Val Lys Lys Ile Ile Arg Val Gly Ser Cys Gly Ala Val Leu
                 85                  90                  95

Pro His Val Lys Leu Arg Asp Val Val Ile Gly Met Gly Ala Cys Thr
                100                 105                 110

Asp Ser Lys Val Asn Arg Ile Arg Phe Lys Asp His Asp Phe Ala Ala
                115                 120                 125

Ile Ala Asp Phe Asp Met Val Arg Asn Ala Val Asp Ala Ala Lys Ala
130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
                180                 185                 190

Phe Gly Ala Lys Ala Leu Thr Ile Cys Thr Val Ser Asp His Ile Arg
                195                 200                 205

Thr His Glu Gln Thr Thr Ala Ala Glu Arg Gln Thr Thr Phe Asn Asp
                210                 215                 220

Met Ile Lys Ile Ala Leu Glu Ser Val Leu Leu Gly Asp Lys Glu
225                 230                 235

<210> SEQ ID NO 16
<211> LENGTH: 650
<212> TYPE: PRT
<213> ORGANISM: Fusarium graminearum

<400> SEQUENCE: 16

Met Ala Ser Ala Pro Ile Gly Val Ala Ile Pro Arg Asn Asn Trp Ala
 1               5                  10                  15

Val Thr Cys Asp Ser Ala Gln Ser Gly Asn Glu Cys Asn Lys Ala Ile
                20                  25                  30

Asp Gly Asn Lys Asp Thr Phe Trp His Thr Gln Tyr Gly Val Asn Gly
                35                  40                  45

Asp Pro Lys Pro Pro His Thr Ile Thr Ile Asp Met Lys Thr Val Gln
 50                  55                  60

Asn Val Asn Gly Leu Ser Val Leu Pro Arg Gln Asp Gly Asn Gln Asn
 65                  70                  75                  80

Gly Trp Ile Gly Arg His Glu Val Tyr Leu Ser Ser Asp Gly Val Asn
                 85                  90                  95

Trp Gly Ser Pro Val Ala Ser Gly Ser Trp Phe Ala Asp Ser Thr Thr
                100                 105                 110

Lys Tyr Ser Asn Phe Glu Thr Arg Pro Ala Arg Tyr Val Arg Leu Val
                115                 120                 125

Ala Ile Thr Glu Ala Asn Gly Gln Pro Trp Thr Ser Ile Ala Glu Ile
                130                 135                 140

Asn Val Phe Gln Ala Ser Ser Tyr Thr Ala Pro Gln Pro Gly Leu Gly
145                 150                 155                 160

Arg Trp Gly Pro Thr Ile Asp Leu Pro Ile Val Pro Ser Ala Ala Ala
                165                 170                 175
```

-continued

```
Ile Glu Pro Thr Ser Gly Arg Val Leu Met Trp Ser Ser Tyr Arg Gln
            180                 185                 190

Asp Ala Phe Glu Pro Ser Pro Gly Gly Ile Thr Leu Thr Ser Ser Trp
        195                 200                 205

Asp Pro Ser Thr Gly Ile Val Ser Asp Arg Thr Ser Thr Val Thr Gly
    210                 215                 220

His Asp Met Phe Cys Pro Gly Ile Ser Met Asp Gly Asn Gly Gln Ile
225                 230                 235                 240

Val Val Ser Gly Gly Asn Asp Ala Lys Lys Thr Ser Leu Tyr Asp Ser
                245                 250                 255

Ser Ser Asp Ser Trp Ile Pro Gly Pro Asp Met Gln Val Ala Arg Gly
            260                 265                 270

Tyr Asn Ser Ser Ala Thr Met Ser Asp Gly Arg Val Phe Thr Ile Gly
        275                 280                 285

Gly Ser Tyr Ser Gly Gly Gln Val Glu Lys Asn Gly Glu Val Tyr Ser
    290                 295                 300

Pro Ser Ser Lys Thr Trp Thr Ser Leu Pro Asn Ala Lys Val Asn Pro
305                 310                 315                 320

Met Leu Thr Ala Asp Lys Gln Gly Leu Tyr Arg Ser Asp Asn His Ala
                325                 330                 335

Trp Leu Phe Gly Trp Lys Lys Gly Ser Val Phe Gln Ala Gly Pro Ser
            340                 345                 350

Thr Ala Met Asn Trp Tyr Tyr Thr Ser Gly Ser Gly Asp Val Lys Ser
        355                 360                 365

Ala Gly Lys Arg Gln Ser Asp Arg Gly Val Ala Pro Asp Ala Met Cys
    370                 375                 380

Gly Asn Ala Val Met Tyr Asp Ala Val Lys Gly Lys Ile Leu Thr Phe
385                 390                 395                 400

Gly Gly Ser Pro Asp Tyr Gln Asp Ser Asp Ala Thr Thr Asn Ala His
                405                 410                 415

Ile Ile Thr Leu Gly Glu Pro Gly Thr Ser Pro Asn Thr Val Phe Ala
            420                 425                 430

Ser Asn Gly Leu Leu Phe Ala Arg Thr Phe His Thr Ser Val Val Leu
        435                 440                 445

Pro Asp Gly Ser Val Phe Ile Thr Gly Gly Gln Gln Arg Gly Val Pro
    450                 455                 460

Leu Glu Asp Ser Thr Pro Val Phe Thr Pro Glu Ile Tyr Val Pro Glu
465                 470                 475                 480

Gln Asp Thr Phe Tyr Lys Gln Asn Pro Asn Ser Ile Val Arg Ala Tyr
                485                 490                 495

His Ser Ile Ser Leu Leu Leu Pro Asp Gly Arg Val Phe Asn Gly Gly
            500                 505                 510

Gly Gly Leu Cys Gly Asp Cys Glu Thr Asn His Phe Asp Ala Gln Ile
        515                 520                 525

Phe Thr Pro Asn Tyr Leu Tyr Asp Ser Asn Gly Asn Leu Ala Thr Arg
    530                 535                 540

Pro Lys Ile Thr Arg Thr Ser Thr Gln Ser Val Val Val Gly Gly Trp
545                 550                 555                 560

Ile Thr Ile Trp Thr Asp Met Ser Ile Ser Ala Ala Ser Leu Ile Arg
                565                 570                 575

Tyr Gly Thr Ala Thr His Thr Val Asn Thr Asp Gln Arg Arg Ile Gly
            580                 585                 590

Leu Thr Leu Thr Asn Asn Gly Gly Asn Ser Tyr Ser Phe Gln Val Pro
```

```
                595             600             605
Ser Asp Ser Gly Val Ala Leu Pro Gly Tyr Trp Met Leu Phe Val Met
            610             615             620
Asn Ser Ala Gly Val Pro Ser Val Ala Ser Thr Ile Asn Val Thr Gln
625             630             635             640
Gly Gln Thr Gly His His His His His His
                645             650

<210> SEQ ID NO 17
<211> LENGTH: 650
<212> TYPE: PRT
<213> ORGANISM: Fusarium graminearum

<400> SEQUENCE: 17

Met Ala Ser Ala Pro Ile Gly Val Ala Ile Pro Arg Asn Asn Trp Ala
1               5                   10                  15
Val Thr Cys Asp Ser Ala Gln Ser Gly Asn Glu Cys Ile Lys Ala Ile
            20                  25                  30
Asp Gly Asn Lys Asp Thr Phe Trp His Thr Gln Tyr Gly Val Asn Gly
        35                  40                  45
Asp Pro Lys Pro Pro His Thr Ile Thr Ile Asp Met Lys Thr Val Gln
    50                  55                  60
Asn Val Asn Gly Leu Ser Val Leu Pro Arg Gln Asp Gly Asn Gln Asn
65                  70                  75                  80
Gly Trp Ile Gly Arg His Glu Val Tyr Leu Ser Ser Asp Gly Val Asn
                85                  90                  95
Trp Gly Ser Pro Val Ala Ser Gly Ser Trp Phe Ala Asp Ser Thr Thr
            100                 105                 110
Lys Tyr Ser Asn Phe Glu Thr Arg Pro Ala Arg Tyr Val Arg Leu Val
        115                 120                 125
Ala Ile Thr Glu Ala Asn Gly Gln Pro Trp Thr Ser Ile Ala Glu Ile
    130                 135                 140
Asn Val Phe Gln Ala Ser Ser Tyr Thr Ala Pro Gln Pro Gly Leu Gly
145                 150                 155                 160
Arg Trp Gly Pro Thr Ile Asp Leu Pro Ile Val Pro Ser Ala Ala Ala
                165                 170                 175
Ile Glu Pro Thr Ser Gly Arg Val Leu Met Trp Ser Ser Tyr Arg Gln
            180                 185                 190
Asp Ala Phe Glu Asp Ser Pro Gly Gly Ile Thr Leu Thr Ser Ser Trp
        195                 200                 205
Asp Pro Ser Thr Gly Ile Val Ser Asp Arg Thr Ser Thr Val Thr Gly
    210                 215                 220
His Asp Met Phe Cys Pro Gly Ile Ser Met Asp Gly Asn Gly Gln Ile
225                 230                 235                 240
Val Val Ser Gly Gly Asn Asp Ala Lys Lys Thr Ser Leu Tyr Asp Ser
                245                 250                 255
Ser Ser Asp Ser Trp Ile Pro Gly Pro Asp Met Gln Val Ala Arg Gly
            260                 265                 270
Tyr Asn Ser Ser Ala Thr Met Ser Asp Gly Arg Val Phe Thr Ile Gly
        275                 280                 285
Gly Ser Tyr Ser Gly Gly Gln Val Glu Lys Asn Gly Glu Val Tyr Ser
    290                 295                 300
Pro Ser Ser Lys Thr Trp Thr Ser Leu Pro Asn Ala Lys Val Asn Pro
305                 310                 315                 320
```

```
Met Leu Thr Ala Asp Lys Gln Gly Leu Tyr Arg Ser Asp Asn His Ala
                325                 330                 335

Trp Leu Phe Gly Trp Lys Lys Gly Ser Val Phe Gln Ala Gly Pro Ser
            340                 345                 350

Thr Ala Met Asn Trp Tyr Tyr Thr Ser Gly Ser Gly Asp Val Lys Ser
        355                 360                 365

Ala Gly Lys Arg Gln Ser Asp Arg Gly Val Ala Pro Asp Ala Met Cys
    370                 375                 380

Gly Asn Ala Val Met Tyr Asp Ala Val Lys Gly Lys Ile Leu Thr Phe
385                 390                 395                 400

Gly Gly Ser Pro Asp Tyr Gln Asp Ser Asp Ala Thr Thr Asn Ala His
                405                 410                 415

Ile Ile Thr Leu Gly Glu Pro Gly Thr Ser Pro Asn Thr Val Phe Ala
                420                 425                 430

Ser Asn Gly Leu Leu Phe Ala Arg Thr Phe His Thr Ser Val Val Leu
            435                 440                 445

Pro Asp Gly Ser Val Phe Ile Thr Gly Gly Gln Arg Gly Val Pro
        450                 455                 460

Leu Glu Asp Ser Thr Pro Val Phe Thr Pro Glu Ile Tyr Val Pro Glu
465                 470                 475                 480

Gln Asp Thr Phe Tyr Lys Gln Asn Pro Asn Ser Ile Val Arg Ala Tyr
                485                 490                 495

His Ser Ile Ser Leu Leu Leu Pro Asp Gly Arg Val Phe Asn Gly Gly
                500                 505                 510

Gly Gly Leu Cys Gly Asp Cys Glu Thr Asn His Phe Asp Ala Gln Ile
            515                 520                 525

Phe Thr Pro Asn Tyr Leu Tyr Asp Ser Asn Gly Asn Leu Ala Thr Arg
        530                 535                 540

Pro Lys Ile Thr Arg Thr Ser Thr Gln Ser Val Val Gly Gly Trp
545                 550                 555                 560

Ile Thr Ile Trp Thr Asp Met Ser Ile Ser Ala Ala Ser Leu Ile Arg
                565                 570                 575

Tyr Gly Thr Ala Thr His Thr Val Asn Thr Asp Gln Arg Arg Ile Gly
            580                 585                 590

Leu Thr Leu Thr Asn Asn Gly Gly Asn Ser Tyr Ser Phe Gln Val Pro
        595                 600                 605

Ser Asp Ser Gly Val Ala Leu Pro Gly Tyr Trp Met Leu Phe Val Met
    610                 615                 620

Asn Ser Ala Gly Val Pro Ser Val Ala Ser Thr Ile Asn Val Thr Gln
625                 630                 635                 640

Gly Gln Thr Gly His His His His His
                645                 650

<210> SEQ ID NO 18
<211> LENGTH: 650
<212> TYPE: PRT
<213> ORGANISM: Fusarium graminearum

<400> SEQUENCE: 18

Met Ala Ser Ala Pro Ile Gly Val Ala Ile Pro Arg Asn Asn Trp Ala
1               5                   10                  15

Val Thr Cys Asp Ser Ala Gln Ser Gly Asn Gl

Asp Pro Lys Pro Pro His Thr Ile Thr Ile Asp Met Lys Thr Val Gln
50                      55                  60

Asn Val Asn Gly Leu Ser Val Leu Pro Arg Gln Asp Gly Asn Gln Asn
65                  70                  75                  80

Gly Trp Ile Gly Arg His Glu Val Tyr Leu Ser Ser Asp Gly Val Asn
                    85                  90                  95

Trp Gly Ser Pro Val Ala Ser Gly Ser Trp Phe Ala Asp Ser Thr Thr
                100                 105                 110

Lys Tyr Ser Asn Phe Glu Thr Arg Pro Ala Arg Tyr Val Arg Leu Val
                115                 120                 125

Ala Ile Thr Glu Ala Asn Gly Gln Pro Trp Thr Ser Ile Ala Glu Ile
        130                 135                 140

Asn Val Phe Gln Ala Ser Ser Tyr Thr Ala Pro Gln Pro Gly Leu Gly
145                 150                 155                 160

Arg Trp Gly Pro Thr Ile Asp Leu Pro Ile Val Pro Ser Ala Ala Ala
                165                 170                 175

Ile Glu Pro Thr Ser Gly Arg Val Leu Met Trp Ser Ser Tyr Arg Gln
                180                 185                 190

Asp Ala Phe Glu Asp Ser Pro Gly Gly Ile Thr Leu Thr Ser Ser Trp
        195                 200                 205

Asp Pro Ser Thr Gly Ile Val Ser Asp Arg Thr Ser Thr Val Thr Gly
210                 215                 220

His Asp Met Phe Cys Pro Gly Ile Ser Met Asp Gly Asn Gly Gln Ile
225                 230                 235                 240

Val Val Ser Gly Gly Asn Asp Ala Lys Lys Thr Ser Leu Tyr Asp Ser
                245                 250                 255

Ser Ser Asp Ser Trp Ile Pro Gly Pro Asp Met Gln Val Ala Arg Gly
                260                 265                 270

Tyr Asn Ser Ser Ala Thr Met Ser Asp Gly Arg Val Phe Thr Ile Gly
                275                 280                 285

Gly Ser Tyr Ser Gly Gly Gln Val Glu Lys Asn Gly Glu Val Tyr Ser
            290                 295                 300

Pro Ser Ser Lys Thr Trp Thr Ser Leu Pro Asn Ala Lys Val Asn Pro
305                 310                 315                 320

Met Leu Thr Ala Asp Lys Arg Gly Leu Tyr Arg Ser Asp Asn His Ala
                325                 330                 335

Trp Leu Phe Gly Trp Lys Lys Gly Ser Val Phe Gln Ala Gly Pro Ser
                340                 345                 350

Thr Ala Met Asn Trp Tyr Tyr Thr Ser Gly Ser Gly Asp Val Lys Ser
            355                 360                 365

Ala Gly Lys Arg Gln Ser Asp Arg Gly Val Ala Pro Asp Ala Met Cys
        370                 375                 380

Gly Asn Ala Val Met Tyr Asp Ala Val Lys Gly Lys Ile Leu Thr Phe
385                 390                 395                 400

Gly Gly Ser Pro Asp Tyr Gln Asp Ser Asp Ala Thr Thr Asn Ala His
                405                 410                 415

Ile Ile Thr Leu Gly Glu Pro Gly Thr Ser Pro Asn Thr Val Phe Ala
                420                 425                 430

Ser Asn Gly Leu Leu Phe Ala Arg Thr Phe His Thr Ser Val Val Leu
            435                 440                 445

Pro Asp Gly Ser Val Phe Ile Thr Gly Gly Gln Arg Gly Val Pro
450                 455                 460

```
Leu Glu Asp Ser Thr Pro Val Phe Thr Pro Glu Ile Tyr Val Pro Glu
465                 470                 475                 480

Gln Asp Thr Phe Tyr Lys Gln Asn Pro Asn Ser Ile Val Arg Ala Tyr
            485                 490                 495

His Ser Ile Ser Leu Leu Leu Pro Asp Gly Arg Val Phe Asn Gly Gly
                500                 505                 510

Gly Gly Leu Cys Gly Asp Cys Glu Thr Asn His Phe Asp Ala Gln Ile
            515                 520                 525

Phe Thr Pro Asn Tyr Leu Tyr Asp Ser Asn Gly Asn Leu Ala Thr Arg
        530                 535                 540

Pro Lys Ile Thr Arg Thr Ser Thr Gln Ser Val Val Val Gly Gly Trp
545                 550                 555                 560

Ile Thr Ile Trp Thr Asp Met Ser Ile Ser Ala Ala Ser Leu Ile Arg
                565                 570                 575

Tyr Gly Thr Ala Thr His Thr Val Asn Thr Asp Gln Arg Arg Ile Gly
            580                 585                 590

Leu Thr Leu Thr Asn Asn Gly Gly Asn Ser Tyr Ser Phe Gln Val Pro
        595                 600                 605

Ser Asp Ser Gly Val Ala Leu Pro Gly Tyr Trp Met Leu Phe Val Met
610                 615                 620

Asn Ser Ala Gly Val Pro Ser Val Ala Ser Thr Ile Asn Val Thr Gln
625                 630                 635                 640

Gly Gln Thr Gly His His His His His His
            645                 650

<210> SEQ ID NO 19
<211> LENGTH: 650
<212> TYPE: PRT
<213> ORGANISM: Fusarium graminearum

<400> SEQUENCE: 19

Met Ala Ser Ala Pro Ile Gly Val Ala Ile Pro Arg Asn Asn Trp Ala
1               5                   10                  15

Val Thr Cys Asp Ser Ala Gln Ser Gly Asn Glu Cys Ile Lys Ala Ile
            20                  25                  30

Asp Gly Asn Lys Asp Thr Phe Trp His Thr Gln Tyr Gly Val Asn Gly
        35                  40                  45

Asp Pro Lys Pro Pro His Thr Ile Thr Ile Asp Met Lys Thr Val Gln
    50                  55                  60

Asn Val Asn Gly Leu Ser Val Leu Pro Arg Gln Asp Gly Asn Gln Asn
65                  70                  75                  80

Gly Trp Ile Gly Arg His Glu Val Tyr Leu Ser Ser Asp Gly Val Asn
                85                  90                  95

Trp Gly Ser Pro Val Ala Ser Gly Ser Trp Phe Ala Asp Ser Thr Thr
            100                 105                 110

Lys Tyr Ser Asn Phe Glu Thr Arg Pro Ala Arg Tyr Val Arg Leu Val
        115                 120                 125

Ala Ile Thr Glu Ala Asn Gly Gln Pro Trp Thr Ser Ile Ala Glu Ile
    130                 135                 140

Asn Val Phe Gln Ala Ser Ser Tyr Thr Ala Pro Gln Pro Gly Leu Gly
145                 150                 155                 160

Arg Trp Gly Pro Thr Ile Asp Leu Pro Ile Val Pro Ser Ala Ala Ala
                165                 170                 175

Ile Glu Pro Thr Ser Gly Arg Val Leu Met Trp Ser Ser Tyr Arg Gln
            180                 185                 190
```

```
Asp Ala Phe Arg Asp Ser Pro Gly Gly Ile Thr Leu Thr Ser Ser Trp
        195                 200                 205

Asp Pro Ser Thr Gly Ile Val Ser Asp Arg Thr Ser Thr Val Thr Gly
        210                 215                 220

His Asp Met Phe Cys Pro Gly Ile Ser Met Asp Gly Asn Gly Gln Ile
225                 230                 235                 240

Val Val Ser Gly Gly Asn Asp Ala Lys Lys Thr Ser Leu Tyr Asp Ser
                245                 250                 255

Ser Ser Asp Ser Trp Ile Pro Gly Pro Asp Met Gln Val Ala Arg Gly
            260                 265                 270

Tyr Asn Ser Ser Ala Thr Met Ser Asp Gly Arg Val Phe Thr Ile Gly
                275                 280                 285

Gly Ser Tyr Ser Gly Gly Gln Val Glu Lys Asn Gly Glu Val Tyr Ser
        290                 295                 300

Pro Ser Ser Lys Thr Trp Thr Ser Leu Pro Asn Ala Lys Val Asn Pro
305                 310                 315                 320

Met Leu Thr Ala Asp Lys Gln Gly Leu Tyr Arg Ser Asp Asn His Ala
                325                 330                 335

Trp Leu Phe Gly Trp Lys Lys Gly Ser Val Phe Gln Ala Gly Pro Ser
            340                 345                 350

Thr Ala Met Asn Trp Tyr Tyr Thr Ser Gly Ser Gly Asp Val Lys Ser
                355                 360                 365

Ala Gly Lys Arg Gln Ser Asp Arg Gly Val Ala Pro Asp Ala Met Cys
        370                 375                 380

Gly Asn Ala Val Met Tyr Asp Ala Val Lys Gly Lys Ile Leu Thr Phe
385                 390                 395                 400

Gly Gly Ser Pro Asp Tyr Gln Asp Ser Asp Ala Thr Thr Asn Ala His
                405                 410                 415

Ile Ile Thr Leu Gly Glu Pro Gly Thr Ser Pro Asn Thr Val Phe Ala
            420                 425                 430

Ser Asn Gly Leu Leu Phe Ala Arg Thr Phe His Thr Ser Val Val Leu
        435                 440                 445

Pro Asp Gly Ser Val Phe Ile Thr Gly Gly Gln Gln Arg Gly Val Pro
        450                 455                 460

Leu Glu Asp Ser Thr Pro Val Phe Thr Pro Glu Ile Tyr Val Pro Glu
465                 470                 475                 480

Gln Asp Thr Phe Tyr Lys Gln Asn Pro Asn Ser Ile Val Arg Ala Tyr
                485                 490                 495

His Ser Ile Ser Leu Leu Leu Pro Asp Gly Arg Val Phe Asn Gly Gly
            500                 505                 510

Gly Gly Leu Cys Gly Asp Cys Glu Thr Asn His Phe Asp Ala Gln Ile
        515                 520                 525

Phe Thr Pro Asn Tyr Leu Tyr Asp Ser Asn Gly Asn Leu Ala Thr Arg
        530                 535                 540

Pro Lys Ile Thr Arg Thr Ser Thr Gln Ser Val Val Gly Gly Trp
545                 550                 555                 560

Ile Thr Ile Trp Thr Asp Met Ser Ile Ser Ala Ala Ser Leu Ile Arg
                565                 570                 575

Tyr Gly Thr Ala Thr His Thr Val Asn Thr Asp Gln Arg Arg Ile Gly
            580                 585                 590

Leu Thr Leu Thr Asn Asn Gly Gly Asn Ser Tyr Ser Phe Gln Val Pro
        595                 600                 605
```

```
Ser Asp Ser Gly Val Ala Leu Pro Gly Tyr Trp Met Leu Phe Val Met
    610             615                 620

Asn Ser Ala Gly Val Pro Ser Val Ala Ser Thr Ile Asn Val Thr Gln
625             630                 635                 640

Gly Gln Thr Gly His His His His His His
                645             650

<210> SEQ ID NO 20
<211> LENGTH: 326
<212> TYPE: PRT
<213> ORGANISM: Escherichia coli

<400> SEQUENCE: 20

Met His His His His His Gly Gly Ser Gly Ser Ile Lys Glu Gln
1               5                   10                  15

Thr Leu Met Thr Pro Tyr Leu Gln Leu Asp Arg Asn Gln Trp Ala Ala
            20                  25                  30

Leu Arg Asp Ser Asn Pro Met Thr Leu Ser Glu Asp Glu Ile Ala Arg
        35                  40                  45

Leu Lys Gly Ile Asn Glu Asp Leu Ser Leu Glu Glu Val Ala Glu Val
    50                  55                  60

Tyr Leu Pro Leu Ser Arg Leu Leu Asn Phe Tyr Ile Ser Ser Asn Leu
65                  70                  75                  80

Arg Arg Gln Ala Gln Leu Glu Gln Phe Leu Gly Thr Asn Gly Gln Arg
                85                  90                  95

Ile Pro Tyr Ile Ile Ser Ile Ala Gly Ser Val Ala Val Gly Lys Ser
            100                 105                 110

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Phe Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn His Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
                325
```

<210> SEQ ID NO 21
<211> LENGTH: 413
<212> TYPE: PRT
<213> ORGANISM: Thermotoga maritima

<400> SEQUENCE: 21

| Met | Gly | Ser | His | His | His | His | His | Gly | Ser | Arg | Val | Leu | Asn | Ile |
|---|---|---|---|---|---|---|---|---|---|---|---|---|---|---|
| 1 | | | | 5 | | | | | 10 | | | | | 15 |

| Asn | Ser | Gly | Ser | Ser | Ile | Lys | Tyr | Gln | Leu | Ile | Glu | Met | Glu | Gly |
|---|---|---|---|---|---|---|---|---|---|---|---|---|---|---|
| | | | 20 | | | | | 25 | | | | | 30 | |

| Glu | Lys | Val | Leu | Cys | Lys | Gly | Ile | Ala | Glu | Arg | Ile | Gly | Ile | Glu | Gly |
|---|---|---|---|---|---|---|---|---|---|---|---|---|---|---|---|
| | | | 35 | | | | | 40 | | | | | 45 | | |

Ser Arg Leu Val His Arg Val Gly Asp Glu Lys His Val Ile Glu Arg
     50                  55                  60

Glu Leu Pro Asp His Glu Ala Leu Lys Leu Ile Leu Asn Thr Leu
65                  70                  75                  80

Val Asp Glu Lys Leu Gly Val Ile Lys Asp Leu Lys Glu Ile Asp Ala
                85                  90                  95

Val Gly His Arg Val Val His Gly Gly Glu Arg Phe Lys Glu Ser Val
                100                 105                 110

Leu Val Asp Glu Glu Val Leu Lys Ala Ile Glu Glu Val Ser Pro Leu
            115                 120                 125

Ala Pro Leu His Asn Pro Ala Asn Leu Met Gly Ile Lys Ala Ala Met
        130                 135                 140

Lys Leu Leu Pro Gly Val Pro Asn Val Gln Val Phe Asp Thr Ala Phe
145                 150                 155                 160

His Gln Thr Ile Pro Gln Lys Ala Tyr Leu Tyr Ala Ile Pro Tyr Glu
                165                 170                 175

Tyr Tyr Glu Lys Tyr Lys Ile Arg Arg Tyr Gly Phe His Gly Ile Ser
            180                 185                 190

His Arg Tyr Val Ser Lys Arg Ala Ala Glu Ile Leu Gly Lys Lys Leu
        195                 200                 205

Glu Glu Leu Lys Ile Ile Thr Cys His Ile Gly Asn Gly Ala Ser Val
210                 215                 220

Ala Ala Val Lys Tyr Gly Lys Cys Val Asp Thr Ser Met Gly Phe Thr
225                 230                 235                 240

Pro Leu Glu Gly Leu Val Met Gly Thr Arg Ser Gly Asp Leu Asp Pro
                245                 250                 255

Ala Ile Pro Phe Phe Ile Met Glu Lys Glu Gly Ile Ser Pro Gln Glu
            260                 265                 270

Met Tyr Asp Ile Leu Asn Lys Lys Ser Gly Val Tyr Gly Leu Ser Lys
        275                 280                 285

Gly Phe Ser Ser Asp Met Arg Asp Asn Leu Glu Ala Ala Leu Lys Gly
    290                 295                 300

Asp Glu Trp Cys Lys Leu Val Leu Glu Ile Tyr Asp Tyr Arg Ile Ala
305                 310                 315                 320

Lys Tyr Ile Gly Ala Tyr Ala Ala Met Asn Gly Val Asp Ala Ile
                325                 330                 335

Val Phe Thr Ala Gly Val Gly Glu Asn Ser Pro Ile Thr Arg Glu Asp
                340                 345                 350

Val Cys Lys Tyr Leu Glu Phe Leu Gly Val Lys Leu Asp Lys Gln Lys
            355                 360                 365

Asn Glu Glu Thr Ile Arg Gly Lys Glu Gly Ile Ile Ser Thr Pro Asp

```
            370                 375                 380
Ser Arg Val Lys Val Leu Val Val Pro Thr Asn Glu Glu Leu Met Ile
385                 390                 395                 400

Ala Arg Asp Thr Lys Glu Ile Val Glu Lys Ile Gly Arg
                405                 410
```

ENZYMATIC SYNTHESIS OF 4'-ETHYNYL NUCLEOSIDE ANALOGS

CROSS-REFERENCE TO RELATED APPLICATIONS

This application is a National Stage application of International Patent Application No. PCT/US2019/040316, filed Jul. 2, 2019, which claims priority to U.S. Provisional Patent Application No. 62/695,508, filed Jul. 9, 2018 and U.S. Provisional Patent Application No. 62/822,320, filed Mar. 22, 2019.

REFERENCE TO SEQUENCE LISTING SUBMITTED ELECTRONICALLY

The sequence listing of the present application is submitted electronically via EFS-Web as an ASCII formatted sequence listing with a file name "24608WOPCT-SEQLIST-02JUl2019.txt", having a creation date of Jul. 2, 2019 and a size of 80.5 kb. This sequence listing submitted via EFS-Web is part of the specification and is herein incorporated by reference in its entirety.

BACKGROUND OF THE INVENTION

4'-Ethynyl-2'-deoxy nucleoside analogs are known for activity against HIV, AIDS and related diseases.

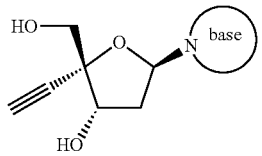

One example of a 4'-ethynyl nucleoside analog is 4'-ethynyl-2-fluoro-2'-deoxyadenosine (EFdA, also known as MK-8591) which is a nucleoside reverse transcriptase translocation inhibitor that blocks HIV-1 and SIV viral replication in vitro (Kawamoto, A, Kodama, E., Sarafianos S. F. et al, Int. J. Biochem. Cell Biol.; 40(11):2410-20 [2008]; Ohrui, H., Kohgo, S., Hayakawa, H. et al, *Nucleosides, Nucleotides & Nucleic Acids,* 26, 1543-1546 [2007]) and in vivo (Hattori, S., Ide, K., Nakata, H. et al. Antimicrobial. Agents and Chemotherapy, 53, 3887-3893 [2009]). EFdA is claimed in U.S. Pat. No. 7,339,053 (referred to in the '053 patent as 2'-deoxy-4'-C-ethynyl-2-fluoroadenosine). EFdA has the following chemical structure:

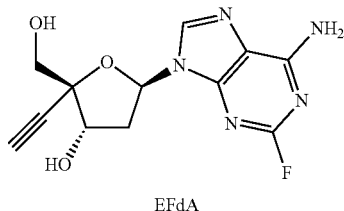 [SMILES: C#C[C@]1(CO)O[C@@H](n2cnc3c(N)nc(F)nc32)C[C@@H]1O]

EFdA

EFdA is metabolized in cells to its active triphosphate anabolite which inhibits HIV reverse transcriptase. In contrast to nucleoside reverse transcriptase inhibitors (NsRTIs) and nucleotide reverse transcriptase inhibitors (NtRTIs) currently available for the treatment of HIV infection which lack a 3'-OH group to block incorporation of incoming nucleotide, EFdA retains a 3' OH group and acts as a chain terminator by preventing translocation of the primer:template in the reverse transcriptase (RT) active site and preventing binding of incoming deoxyribonucleotide triphosphates (dNTPs). In addition, the pucker of the modified ribose ring of EFdA is believed to contribute to inhibition of reverse transcriptase by placing the 3'-OH in a vector in which phosphotransfer from the incoming nucleotide is inefficient. (Michailidis E, et al., Mechanism of inhibition of HIV-1 reverse transcriptase by 4'-ethynyl-2-fluoro-2'-deoxyadenosine triphosphate, J Biol Chem 284:35681-35691 [2009]; Michailidis E, et al., 4'-Ethynyl-2-fluoro-2'-deoxyadenosine (EFdA) inhibits HIV-1 reverse transcriptase with multiple mechanisms, J Biol Chem 289:24533-24548 [2014]).

In in-vitro HIV replication assays, EFdA is a potent antiretroviral and exhibits comparable antiviral activity against clinical isolates across all subtypes that have been evaluated. It is rapidly anabolized in both lymphoid derived cell lines and in peripheral blood mononuclear cells to the active triphosphate in vitro, and the intracellular half-life of EFdA Triphosphate (EFdA-TP) exceeds 72 hrs. (Stoddart, C. A., Galkina, et al., Oral Administration of the Nucleoside EFdA (4'-Ethynyl-2-Fluoro-2'-Deoxyadenosine) Provides Rapid Suppression of HIV Viremia in Humanized Mice and Favorable Pharmacokinetic Properties in Mice and the Rhesus Macaque, Antimicrob Agents Chemother, 2015 July; 59(7): 4190-4198, Published online 2015 May 4).

EFdA has been shown to have efficacy in animal models of HIV infection including humanized mouse models and an SIV infected rhesus macaque model. Pharmacokinetic studies of orally administered EFdA in mouse and rhesus monkey have demonstrated rapid absorption and high plasma concentrations. A long intracellular half-life was demonstrated by the fact that isolated peripheral blood mononuclear cells from the rhesus macaque were refractory to SIV infection 24 hr after drug administration. (Ibid.)

Previous syntheses of 4'-ethynyl nucleoside analogs including EFdA suffer from modest stereoselectivity in the formation of the C—N bond between the ethynyl-deoxyribose sugar and the 2-fluoroadenine (also referred to as 2-fluoro-9H-purin-6-amine) nucleobase. The previous syntheses also require protecting groups to carry out the glycosylation reaction which reduces the efficiency of the syntheses.

The synthesis described in Kei Fukuyama, et al., Synthesis of EFdA via a Diastereoselective Aldol Reaction of a Protected 3-Keto Furanose, Organic Letters 2015, 17(4), pp. 828-831; DOI: 10.1021/ol5036535) is a 14-step synthesis from D-glucose diacetonide that uses diastereoselective reactions to set the three stereocenters. The stereochemistry of the anomeric center is controlled by having a 2'-acetoxy directing group that is subsequently removed by hydrolysis and deoxygenation. This route requires 4 chromatographic purifications, and the stoichiometric use of a toxic organotin reagent for late-stage deoxygenation.

In another route (see Mark McLaughlin, et al., Enantioselective Synthesis of 4'-Ethynyl-2-fluoro-2'-deoxyadenosine (EFdA) via Enzymatic Desymmetrization, Organic Letters 2017, 19 (4), pp. 926-929), the fully-substituted 4'-carbinol is generated stereoselectively with an enzymatic desymmetrization. The 3'-stereocenter is set with a catalytic asymmetric transfer hydrogenation, and the anomeric 1'-linkage is established in modest stereoselectivity using substrate control, with an upgrade in stereochemical purity achieved by crystallization of an intermediate. This process requires 15 steps, requires the use of several protecting groups and generates the glycosyl linkage between the nucleobase and sugar fragments in low stereoselectivity (1.8:1).

A 12-step synthesis for making EFdA from R-glyceraldehyde acetonide is described in Kageyama, M., et al., Concise Synthesis of the Anti-HIV Nucleoside EFdA, Biosci. Biotechnol. Biochem, 2012, 76, pp. 1219-1225; and Enantioselective Total Synthesis of the Potent Anti-HIV Nucleoside EFdA, Masayuki Kageyama, et al., Organic Letters 2011 13 (19), pp. 5264-5266 [DOI: 10.1021/ol202116k]. The syntheses use the chiral starting material to set the 3'-stereocenter with moderate diastereoselectivity. After chromatographic separation of stereoisomers, the new stereocenter is used to guide a diastereoselective alkyne addition to set the fully-substituted 4'-stereocenter. The anomeric 1'-position is established with little stereocontrol and requires chromatography to separate the anomers. This route requires chromatographic separation of diastereoisomers at two different stages and starts from an expensive chiral starting material.

Kohgo, S., et al., Design, Efficient Synthesis, and Anti-HIV Activity of 4'-C-Cyano- and 4'-C-Ethynyl-2'-deoxy Purine Nucleosides, Nucleosides, Nucleotides and Nucleic Acids, 2004, 23, pp. 671-690 [ DOI: 10.1081/NCN-120037508] describes a synthetic route that starts from an existing nucleoside and modifies both the sugar and nucleobase portions. It is an 18-step synthesis starting from 2-amino-2'-deoxyadenosine with a low 2.5% overall yield.

It is known that enzymes such as purine nucleoside phosphorylase (PNP, EC 2.4.2.1) can form the glycosyl linkage in nucleosides and nucleoside analogs in high stereoselectivity and without the use of protecting groups. See for example the review: New Trends in Nucleoside Biotechnology, Mikhailopulo, I. A., Miroshnikov, A. I, *Acta Naturae* 2010, 2, pp. 36-58. However, the current scope of the sugar fragments capable of undergoing reaction catalyzed by PNP has been limited to the α-1-phosphates of natural ribose and deoxyribose along with a small number of analogs with small H, $NH_2$, or F substituents at the C2' and C3' positions and replacements of the C5' OH group. There have been no reports of successful glycosylation catalyzed by PNP using sugars with carbon substituents on the ring or any substitution at the C4' position.

Access to the ribose and deoxyribose α-1-phosphate substrates for the PNP-catalyzed glycosylation has been demonstrated by translocation of the phosphate group from the 5'-hydroxyl to 1'-hydroxyl position with the enzyme phosphopentomutase (PPM, EC 5.4.2.7) (see Mikhailopulo, I. A., et al. supra). However, the scope of the sugars for which PPM is capable of catalyzing this reaction has been limited to ribose, arabinose, 2-deoxyribose, and 2,3-dideoxyribose. No examples have been reported of successful reaction with sugar phosphates containing any additional substituents.

Deoxyribose phosphate aldolase (DERA, EC 4.1.2.4) enzymes are known to catalyze the aldol addition of acetaldehyde to other short-chain aldehydes (see review: Stephen M. Dean, et al., Recent Advances in Aldolase-Catalyzed Asymmetric Synthesis, Adv. Synth. Catal. 2007, 349, pp. 1308-1320; DOI: 10.1002/adsc.200700115). However, no examples have been reported with aldehydes bearing a fully substituted carbon α to the aldehyde.

U.S. Pat. No. 7,229,797 describes the formation of deoxyribonucleosides from the natural unsubstituted deoxyribose 1-phosphate by use of purine nucleoside phosphorylase (PNP) and additionally using enzymes such as sucrose phosphorylase to remove the inorganic phosphate byproduct and drive the equilibrium. It does not disclose enzyme engineering for the creation of PNP enzymes that can generate nucleosides from the unnatural 4-ethynyl-D-2-deoxyribose 1-phosphate, nor that through engineering of PPM and DERA enzymes to act on unnatural substrates, 4-ethynyl-D-2-deoxyribose 1-phosphate can be generated.

In view of the difficult and lengthy synthetic options developed to date for producing 4'-ethynyl nucleoside analogs, it would be desirable to develop an improved enzymatic synthesis for 4'-ethynyl nucleoside analogs such as EFdA that reduces the number of process steps, minimizes the use of protecting groups, improves the stereoselectivity of glycosylation and avoids the use of toxic materials.

Surprisingly, it has been found that PPM enzymes have some activity with the 3-atom ethynyl substituent at the 4' position on ribose and that the PPM enzyme activity could be improved by introducing mutations into the enzymes to successfully develop a reaction for isomerization of 4-ethynyl-D-2-deoxyribose 5-phosphate (6) to 4-ethynyl-D-2-deoxyribose 1-phosphate (6.5) catalyzed by PPM to enable a more efficient method for production of 4'-ethynyl-2'-deoxy nucleosides.

Additionally, PNP enzymes have also been found to have some activity with the 3-atom ethynyl substituent at the 4 position on deoxyribose and that the PNP enzyme activity could be improved by introducing mutations into the enzymes to successfully develop a glycosylation reaction catalyzed by PNP to enable a more efficient method for production of 4'-ethynyl-2'-deoxy nucleosides.

Even further improvement to the overall synthetic method came from the finding that DERA enzymes, particularly the DERA from *Shewanella halifaxensis*, have activity for aldol reaction with 2-ethynyl-glyceraldehyde 3-phosphate which has a fully substituted α-carbon. This discovery allowed for the efficient synthesis of 4-ethynyl-D-2-deoxyribose 5-phosphate, a precursor to 4'-ethynyl-2'-deoxy nucleoside analogs, e.g., including EFdA.

SUMMARY OF THE INVENTION

The present invention involves the use of engineered enzymes in a novel enzymatic synthesis of 4'-ethynyl-2'-deoxy nucleoside analogs, including EFdA, that eliminates the use of protecting groups on intermediates, improves the stereoselectivity of glycosylation and greatly reduces the number of process steps needed to make said compounds compared to prior methods, among other process improvements. It further relates to novel intermediates which are an integral part of the enzymatic process.

The overall process is summarized in the following Scheme 1 and Scheme 2; the latter scheme provides an alternative method for making compound 5:

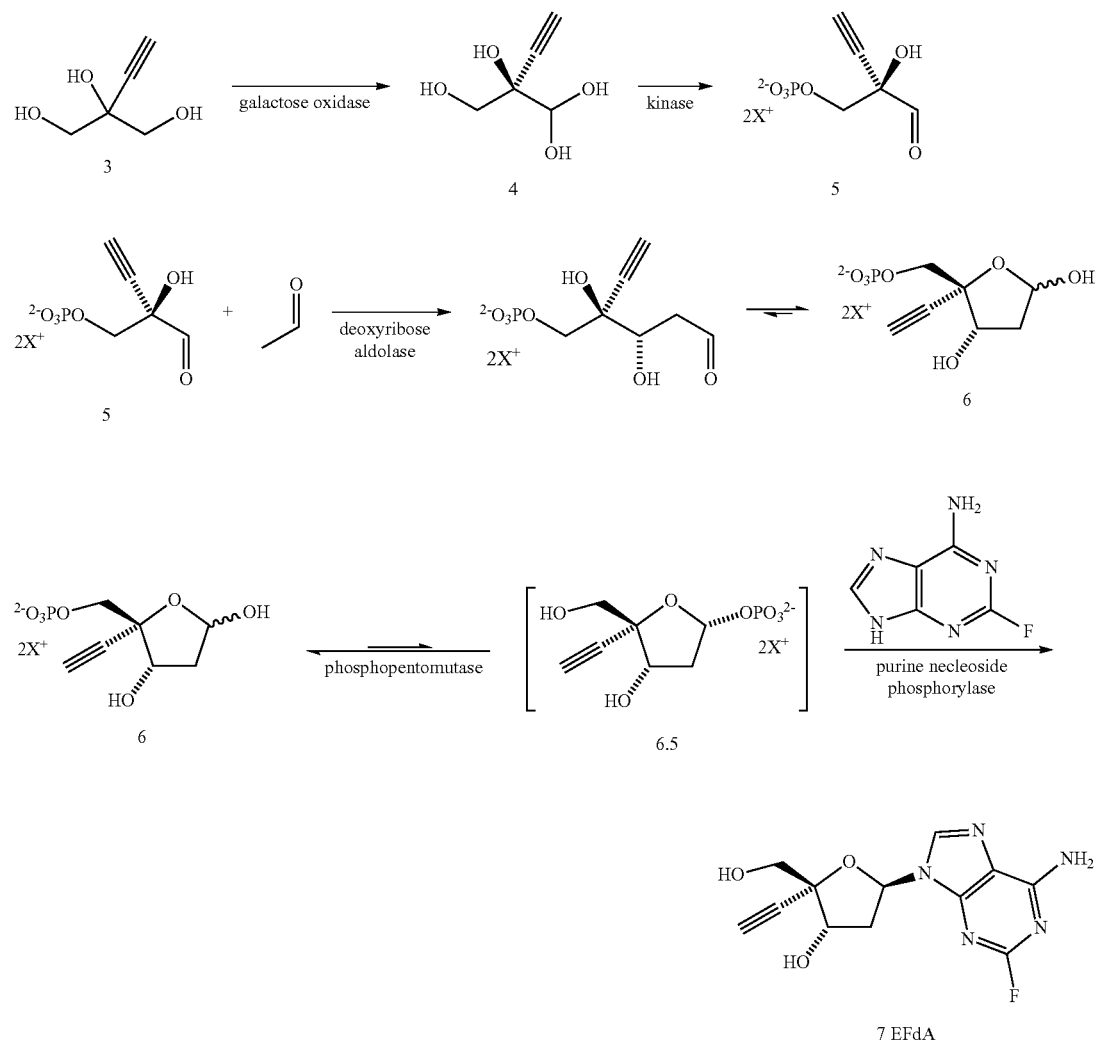
Scheme 1
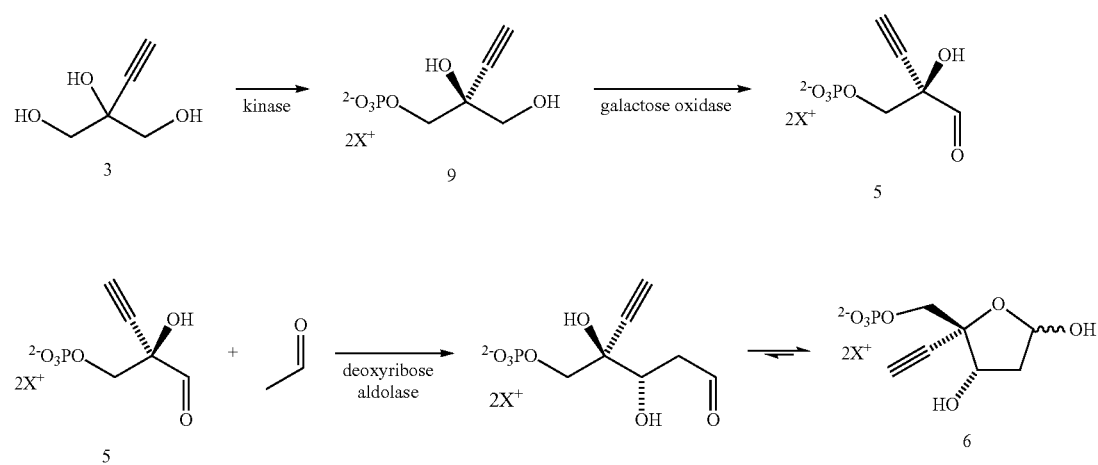
Scheme 1A

-continued

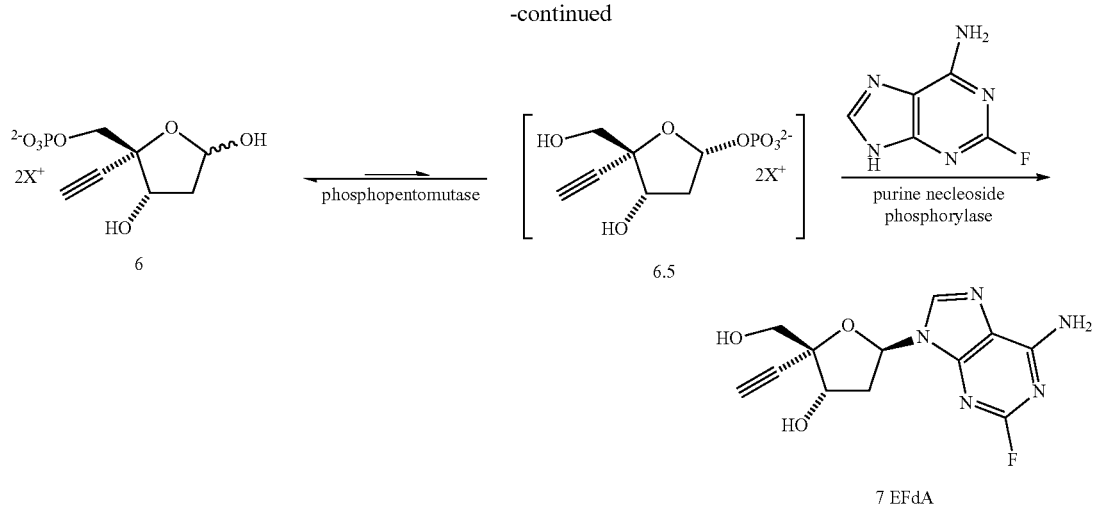

The acid form or salts of phosphate intermediates can be employed in the process described herein and are not limited to specific acid or salt forms provided in exemplifications of the process steps herein. For all phosphate intermediates described herein, $2X^+$ represents any combination of two protons, one proton with one other monovalent cation, two monovalent cations (the same or different) or one divalent cation. Phosphate intermediates drawn herein with —HO$_3$PO— likewise can have any combination of two protons, one proton with one other monovalent cation, two monovalent cations (the same or different) or one divalent cation, associated with the phosphate group. Examples include, but are not limited to, salts of calcium, magnesium, or zinc; mono or di-sodium salts, mono or di-potassium salts, mono or di-lithium salts; mono or di-ammonium salts; or mono- or di-valent salts with primary, secondary or tertiary amines.

As is well understood in the art, the intermediate compounds shown or named herein as aldehyde or hydrate in the synthetic steps herein can exist in either form or a mixture of such forms in the reactions described herein. For example, compounds (4) and (5) are depicted in Scheme 1 as a hydrate and an aldehyde, respectively, but each can exist in hydrate or aldehyde form or a mixture thereof in the reaction steps where each is present. Each such form is encompassed by reference to compound numbers (4) or (5) within the process steps herein:

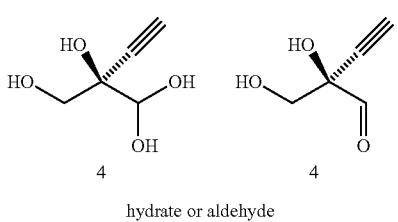

hydrate or aldehyde

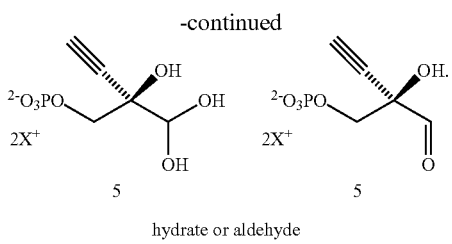

hydrate or aldehyde

Compound (3) is achiral and may be shown herein as either of the following:

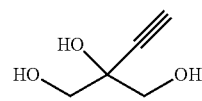

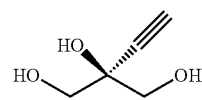

Compound (6) can exist in its ring form or as an open chain aldehyde or hydrate, each as an acid or a salt thereof, in the reaction steps where it is present:

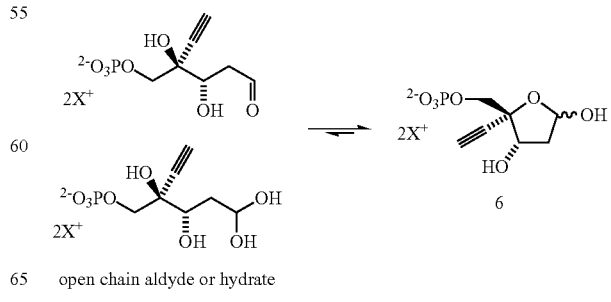

open chain aldyde or hydrate

DETAILED DESCRIPTION OF THE INVENTION

4'-Ethynyl-2'-deoxy nucleosides and analogs thereof

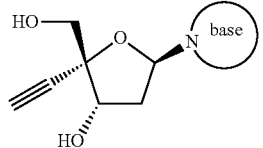

having an anomeric C—N linkage have been explored for activity against HIV, AIDS and related diseases. 4'-Ethynyl-2'-deoxy nucleosides and analogs thereof comprise a 4'-ethynyl-2'-deoxy ribose attached via an anomeric C—N linkage to a purine or pyrimidine nucleobase (adenine, guanine, cytosine, thymine or uracil) or a modified purine or pyrimidine nucleobase.

It has been discovered that 4'-ethynyl-2'-deoxy nucleoside analogs such as EFdA can be synthesized employing a final step one-pot process by combining 4-ethynyl-D-2-deoxyribose 5-phosphate (6) with two enzymes, phosphopentomutase (PPM) [for example but not limited to SEQ ID NO.: 8] and purine nucleoside phosphorylase (PNP) [for example but not limited to SEQ ID NO.: 9, SEQ ID NO.: 15], as shown in Scheme 2.

Scheme 2

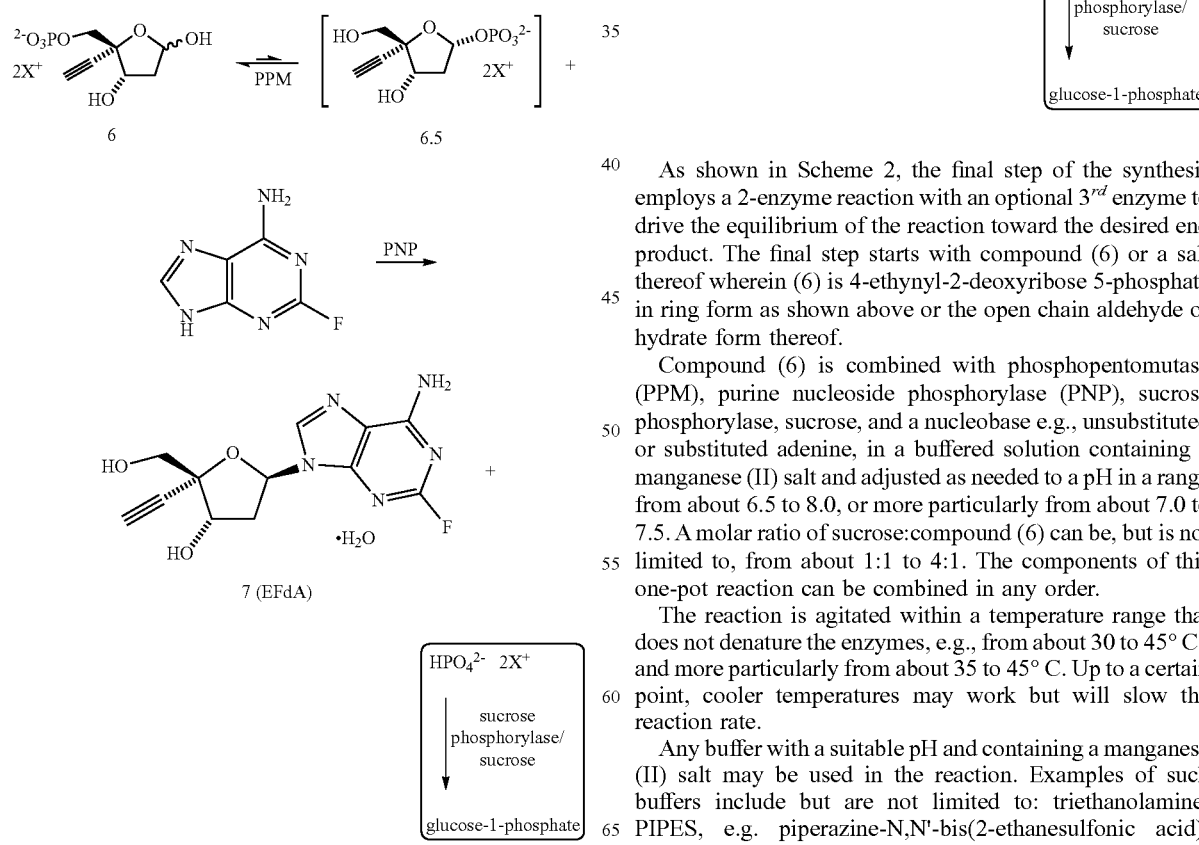

Scheme 2A

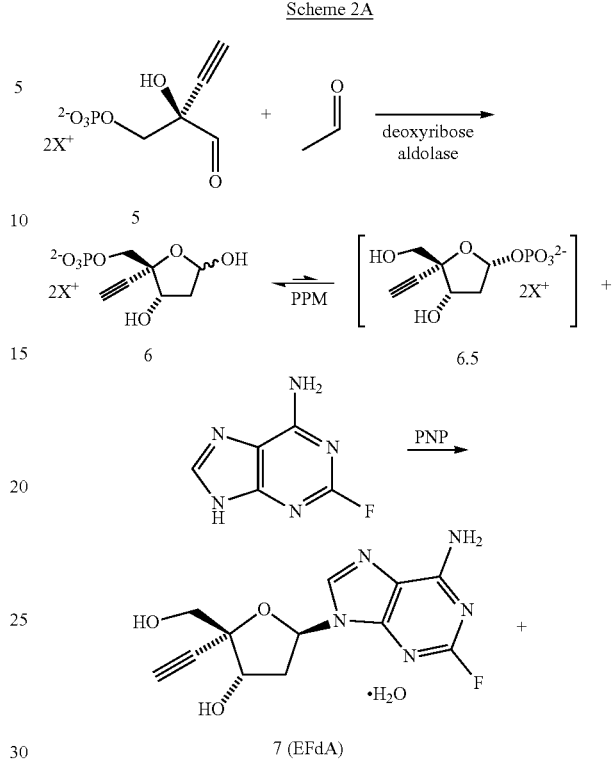

As shown in Scheme 2, the final step of the synthesis employs a 2-enzyme reaction with an optional $3^{rd}$ enzyme to drive the equilibrium of the reaction toward the desired end product. The final step starts with compound (6) or a salt thereof wherein (6) is 4-ethynyl-2-deoxyribose 5-phosphate in ring form as shown above or the open chain aldehyde or hydrate form thereof.

Compound (6) is combined with phosphopentomutase (PPM), purine nucleoside phosphorylase (PNP), sucrose phosphorylase, sucrose, and a nucleobase e.g., unsubstituted or substituted adenine, in a buffered solution containing a manganese (II) salt and adjusted as needed to a pH in a range from about 6.5 to 8.0, or more particularly from about 7.0 to 7.5. A molar ratio of sucrose:compound (6) can be, but is not limited to, from about 1:1 to 4:1. The components of this one-pot reaction can be combined in any order.

The reaction is agitated within a temperature range that does not denature the enzymes, e.g., from about 30 to 45° C., and more particularly from about 35 to 45° C. Up to a certain point, cooler temperatures may work but will slow the reaction rate.

Any buffer with a suitable pH and containing a manganese (II) salt may be used in the reaction. Examples of such buffers include but are not limited to: triethanolamine; PIPES, e.g. piperazine-N,N'-bis(2-ethanesulfonic acid); MOPS, e.g., 3-(N-morpholino)propanesulfonic acid or 3-morpholinopropane-1-sulfonic acid; HEPES, e.g., 4-(2- hydroxyethyl)-1-piperazineethanesulfonic acid or 2-[4-(2-hydroxyethyl)piperazin-1-yl]ethanesulfonic acid; TRIS, e.g., tris(hydroxymethyl)aminomethane or 2-Amino-2-(hydroxymethyl)propane-1,3-diol; and BIS-TRIS methane, e.g., 2-[Bis(2-hydroxyethyDamino]-2-(hydroxymethyl)propane-1,3-diol. More particularly, the buffer is triethanolamine. The manganese (II) salt in the buffer can be, for example, manganese chloride, manganese chloride hydrate, manganese bromide, manganese iodide, manganese nitrate, and/or manganese sulfate. The manganese concentration in the buffer can range from about 0.05 mM to about 10 mM, and particularly it is about 5 mM.

The equilibrium reaction can be driven forward to high conversion of the final product by consumption of the byproduct inorganic phosphate salt by phosphorolysis of sucrose to D-fructose and α-D-glucose-1-phosphate, catalyzed by sucrose phosphorylase (EC 2.4.1.7) added to the reaction mixture. However, any other options for removing phosphate during the reaction can be employed, e.g., adding calcium, magnesium, or manganese to the reaction to precipitate a phosphate salt instead of using sucrose phosphorylase and sucrose. This highly efficient and ecologically friendly process has the advantage of forming the anomeric linkage between sugar and nucleobase with very high stereoselectivity without the use of protecting groups or organic solvents and can be performed as a one pot reaction.

Once the reaction is complete, the final product can be isolated using standard procedures known to persons of ordinary skill in the art, such as but not limited to, isolation by crystallization of the final product and collection by filtration, or extraction into an appropriate solvent followed by crystallization.

As shown in Scheme 2A, the final step of the synthesis can alternatively employ a 3-enzyme reaction with an optional 4$^{th}$ enzyme to drive the equilibrium of the reaction toward the desired end product. The final step starts with compound (5) or a salt thereof, wherein (5) is (R)-2-ethynyl-glyceraldehyde 3-phosphate or a hydrate form thereof.

Compound (5) is combined with deoxyribose-phosphate aldolase (DERA), acetaldehyde, phosphopentomutase (PPM), purine nucleoside phosphorylase (PNP), sucrose phosphorylase, sucrose, and a nucleobase or an analog thereof e.g., unsubstituted or substituted adenine, in a buffered solution containing a manganese (II) salt and adjusted as needed to a pH in a range from about 4 to 10, or particularly from about 6.5 to 8.0, or more particularly from about 7.0 to 7.5. A molar ratio of sucrose:compound (5) can be, but is not limited to, from about 1:1 to 4:1. The components of this one-pot reaction can be combined in any order.

The reaction is performed within a temperature range that does not denature the enzymes, for example from about 30 to 45° C., or particularly from about 35 to 45° C. Up to a certain point, cooler temperatures may work but will slow the reaction rate.

The acetaldehyde is added as a solution, and more particularly as a 40 wt % solution in isopropyl alcohol. Any suitable solution of acetaldehyde or neat acetaldehyde may be used in the reaction. Examples of such solutions include but are not limited to: acetaldehyde solution in isopropanol, acetaldehyde solution in ethanol, acetaldehyde solution in water, acetaldehyde solution in THF. A molar ratio of aldehyde:compound (5) can be, but is not limited to, from about 0.5:1 to 4:1, and more particularly 1.5:1.

Any buffer with a suitable pH and containing a manganese (II) salt may be used in the reaction. Examples of such buffers include but are not limited to: triethanolamine; PIPES, e.g. piperazine-N,N'-bis(2-ethanesulfonic acid); MOPS, e.g., 3-(N-morpholino)propanesulfonic acid or 3-morpholinopropane-1-sulfonic acid; HEPES, e.g., 4-(2-hydroxyethyl)-1-piperazineethanesulfonic acid or 2-[4-(2-hydroxyethyl)piperazin-1-yl]ethanesulfonic acid; TRIS, e.g., tris(hydroxymethyl)aminomethane or 2-Amino-2-(hydroxymethyl)propane-1,3-diol; and BIS-TRIS methane, e.g., 2-[Bis(2-hydroxyethyDamino]-2-(hydroxymethyl)propane-1,3-diol. More particularly, the buffer is triethanolamine. The manganese (II) salt in the buffer can be, for example, manganese chloride, manganese chloride hydrate, manganese bromide, manganese iodide, manganese nitrate, and/or manganese sulfate. The manganese concentration in the buffer can range from about 0.05 mM to about 10 mM, and particularly it is about 5 mM.

The equilibrium reaction can be driven forward to high conversion of the final product by consumption of the byproduct inorganic phosphate salt by phosphorolysis of sucrose to D-fructose and α-D-glucose-1-phosphate, catalyzed by sucrose phosphorylase (EC 2.4.1.7) added to the reaction mixture. However, any other options for removing phosphate during the reaction can be employed, e.g., adding calcium, magnesium, or manganese to the reaction to precipitate a phosphate salt instead of using sucrose phosphorylase and sucrose. This highly efficient and ecologically friendly process has the advantage of forming the anomeric linkage between sugar and nucleobase with very high stereoselectivity without the use of protecting groups or organic solvents and can be performed as a one pot reaction.

Once the reaction is complete, the final product can be isolated using standard procedures known to persons of ordinary skill in the art, such as but not limited to, isolation by crystallization of the final product and collection by filtration, or extraction into an appropriate solvent followed by crystallization.

Several upstream intermediates used in the present process for the synthesis of the final product 4'-ethynyl-2'-deoxy nucleosides and analogs thereof are also made using enzymatic reaction methods as shown in Scheme 3; Scheme 3A and Scheme 3B

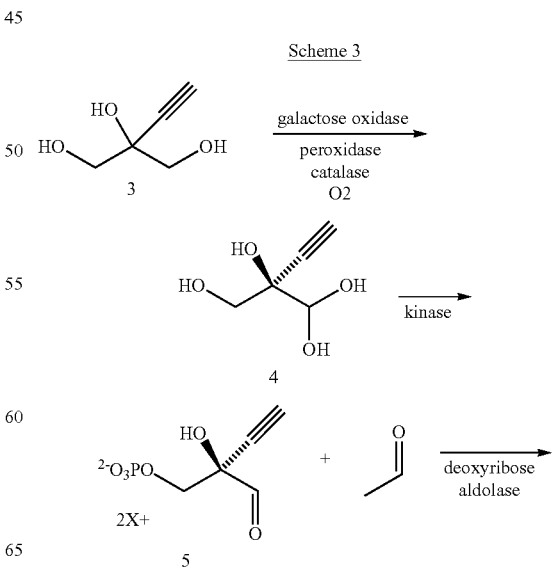

Scheme 3

Scheme 3A

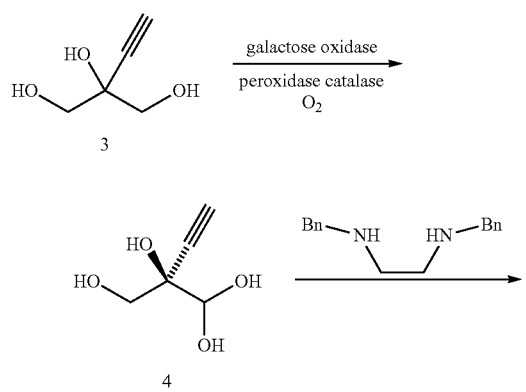

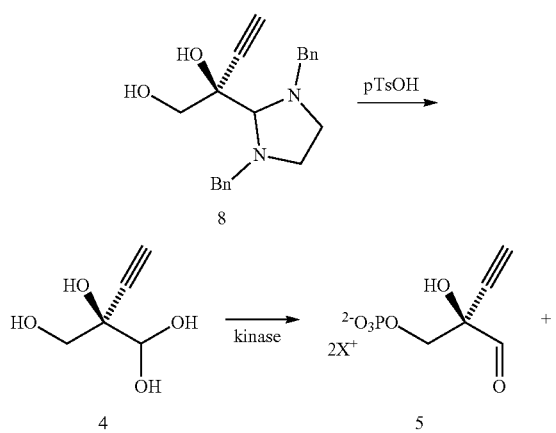

Scheme 3B

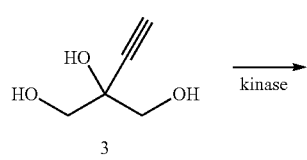

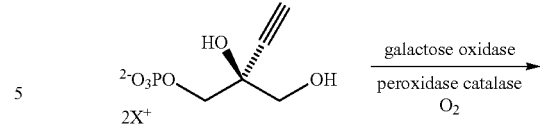

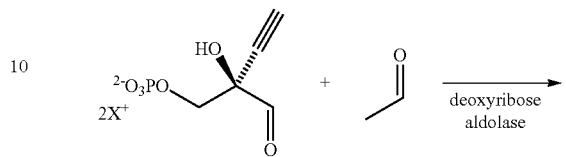

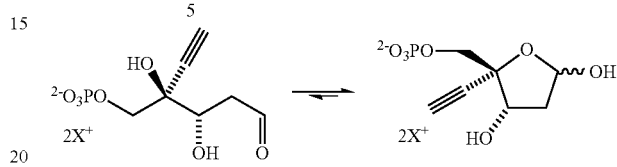

Compound 4: Oxidase Reaction

As shown in Scheme 3, (R)-2-ethynyl-glyceraldehyde (4) is prepared by reacting galactose oxidase with 2-ethynyl-propane-1,2,3-triol (3) in a buffered solution adjusted as needed to a pH in a range from about 3 to 10, or more particularly from about 6 to 8. Any buffer having a suitable pH range can be used, for example but not limited to, sodium phosphate; sodium acetate; PIPES, e.g. piperazine-N,N'-bis(2-ethanesulfonic acid); MOPS, e.g., 3-(N-morpholino)propanesulfonic acid or 3-morpholinopropane-1-sulfonic acid; HEPES, e.g., 4-(2-hydroxyethyl)-1-piperazineethanesulfonic acid or 2-[4-(2-hydroxyethyl)piperazin-1-yl]ethanesulfonic acid; TRIS, e.g., tris(hydroxymethyl)aminomethane or 2-Amino-2-(hydroxymethyl)propane-1,3-diol; and BIS-TRIS methane, e.g., 2-[Bis(2-hydroxyethyl)amino]-2-(hydroxymethyl)propane-1,3-diol; borate; CAPS, e.g., N-cyclohexyl-3-aminopropanesulfonic acid; MES, e.g. 2-(N-morpholino)ethanesulfonic acid; CHES, e.g., N-Cyclohexyl-2-aminoethanesulfonic acid; Glycine; or Bicine (N,N-Bis(2-hydroxyethyl)glycine); with sodium phosphate being preferred.

Copper and a peroxidase are both used in the reaction to activate galactose oxidase (GOase). Copper can be supplied to the reaction mixture by addition of $CuSO_4$, $Cu(OAc)_2$, $CuCl_2$ or other salts of Cu(II) or Cu(I). The peroxidase can be a horseradish peroxidase, or a peroxidase derived from other organisms, or it can be replaced by an oxidant such as ferricyanide, iridate, manganese (III) salts, persulfate salts and other one electron or two electron oxidants, or inorganic or organic oxidants. Preferably, the peroxidase is a horseradish peroxidase. A catalase is also added to help prevent GOase deactivation. The catalase can be from a mammalian source (bovine) or from a bacterial or fungal source such as *Corynebacterium*, *Aspergillus* or other organisms known in the art for this purpose.

The reaction proceeds in the presence of oxygen. One convenient method is sparging the reaction with air. Alternatively, other systems to generate oxygen can employed, such as hydrogen peroxide/catalase, superoxide or use of other methods known in the art for this purpose.

The reaction can be performed with substrate concentration of about 10 to 180 g/L, and particularly 20 to 50 g/L.

The reaction can be run at a temperature from about 0 to 40° C., and particularly from about 10 to 30° C.

Compound 8: Animal Formation

As exemplified in Scheme 3A, (R)-2-ethynyl-glyceraldehyde (4) can be isolated in its animal form (for example, compound 8) by reacting it with any amine, diamine or amino alcohol that forms a stable N,N-acetal or N,O-acetal, for example but not limited to, N,N'-dibenzylethane-1,2-diamine, N,N'-dimethylethane-1,2-diamine, N,N'-diphenylethane-1,2-diamine, and N-benzylethanolamine; with N,N'-dibenzylethane-1,2-diamine being preferred. The reaction is performed in an organic solvent at a temperature at or below about 50° C., preferably from 20 to 30° C., to avoid the decomposition of the animal. Any solvent that is not miscible with water can be used, for example but not limited to, MTBE, 2-MeTHF, CPME, diethyl ether, diisopropyl ether, ethyl acetate, isopropyl acetate, toluene, DCM or a mixture thereof, with MTBE being preferred. The reaction can be performed with a substrate concentration of about 10 to 100 g/L, and particularly 20 to 50 g/L.

Optionally the animal can be further purified by crystallization from an organic solvent, for example but not limited to, MTBE, 2-MeTHF, CPME, diethyl ether, diisopropyl ether, ethyl acetate, isopropyl acetate, toluene, DCM or a mixture thereof, with MTBE being preferred. The crystallization is performed at or below 50° C., for example at about 40° C., to avoid the decomposition of the animal.

The reaction proceeds in the absence of oxygen. One convenient method is sparging the reaction with $N_2$. Alternatively, other systems to exclude oxygen can employed, such as argon, helium, or use of other methods known in the art for this purpose.

Compound 4: Aldehyde 4 Regeneration from the Animal 8

(R)-2-Ethynyl-glyceraldehyde (4) can be regenerated from its respective animal by reacting it with an organic or inorganic acid in the presence of organic solvent that is not miscible with water, at a temperature at or below 50° C., for example from about 0 to 15° C., to avoid the decomposition of the animal. Any organic or inorganic acid can be used, for example but not limited to, p-toluenesulfonic acid, methanesulfonic acid, camphoresulfonic acid, acetic acid, hydrochloric acid, phosphoric acid, sulphuric acid. p-Toluenesulfonic acid is preferred in the reaction with animal 8 due to low solubility of the N,N'-dibenzylethane-1,2-diamine bis p-toluenesulfonate salt in water. Any solvent that is not miscible with water can be used, for example but not limited to, MTBE, 2-MeTHF, CPME, diethyl ether, diisopropyl ether, ethyl acetate, isopropyl acetate, toluene, DCM or a mixture thereof; with MTBE and 2-MeTHF being preferred. The reaction can be performed with a substrate concentration of about 5 to 100 g/L, and particularly 20 to 50 g/L.

Optionally the aldehyde 4 solution can be further treated with a resin to remove the excess of the organic or inorganic acid. The resin treatment can be performed with basic resins such as DOWEX™ MARATHON™ A resin (hydroxide form) and AMBERLYST® 15 resin (hydrogen form), or the mixture thereof, preferably a mixture DOWEX™ MARATHON™ A resin (hydroxide form) and AMBERLYST® 15 resin.

Optionally the aldehyde 4 solution can be further evaporated under vacuum or sweept with a gas to remove the excess of organic solvent.

Compound 5: Kinase Reaction

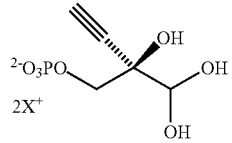

As shown in Scheme 3 and Scheme 3A, (R)-2-ethynyl-glyceraldehyde 3-phosphate hydrate (5) is prepared by reacting pantothenate kinase (PanK) wild type from *E. coli* or a variant thereof, with compound (4) in a buffered solution adjusted as needed to a pH in a range from about 4 to 10, or particularly about 6.5 to 8.5 or more particularly 5.5 to 8.5 Any buffer having a suitable pH range can be used, for example but not limited to, sodium phosphate, PIPES, e.g. piperazine-N,N'-bis(2-ethanesulfonic acid); BIS-TRIS methane, e.g., 2-[Bis(2-hydroxyethyl)amino]-2-(hydroxymethyl)propane-1,3-diol; borate; HEPES, e.g., 4-(2-hydroxyethyl)-1-piperazinethanesulfonic acid or 2-[4-(2-hydroxyethyl)piperazin-1-yl]ethanesulfonic acid; triethanolamine and TRIS, e.g., TRIS, e.g., tris(hydroxymethyl)aminomethane or 2-Amino-2-(hydroxymethyl)propane-1,3-diol; with sodium phosphate being preferred. The reaction can be performed in the presence of any suitable bi-valent metal salt, for example but not limited to a magnesium salt, for example magnesium chloride, and salts of cobalt, manganese, zinc or calcium.

This reaction utilizes adenosine 5'-diphosphate (ADP) as the phosphate source which requires regenerating to 5'-triphosphate (ATP). ATP can be generated in situ and subsequently regenerated by any method known in the art from ADP, adenosine 5'-monophosphate (AMP) or adenosine. For example, a combination of acetyl phosphate together with acetate kinase can be used for regenerating ADP to ATP. For example, in the presence of pyruvate, phosphate and oxygen, a combination of pyruvate oxidase and catalase generates acetyl phosphate, and therefore in the presence of acetate kinase, can be used for regenerating ADP to ATP.

The reaction can be performed with a substrate concentration of about 10 to 100 g/L, and particularly about 20 to 40 g/L. The reaction can be run at a temperature from about 0 to 40° C., and particularly at about 10 to 25° C.

The reaction can also be performed with pantothenate kinase (PanK) immobilized on a resin, or with both PanK and acetate kinase immobilized on the resin. Any suitable enzyme immobilization method known in the art can be used, for example but not limited to, Immobilized Metal-Ion Affinity Chromatography (IMAC) resin, or an affinity resin-immobilization using other biological tags, co-valent immobilization, immobilization on ionic resins, immobilization by adsorption, encapsulation, and/or crosslinked enzymes. For example, the Metal-Ion Affinity Chromatography (IMAC) resin can be used, or any suitable combination of IMAC resin and bi-valent cation can be used wherein the cation can be, for example but not limited to, nickel, cobalt, copper, zinc, iron, and/or aluminum. Particularly, IMAC resin charged with nickel can be used. Preferably, both acetate kinase and pantothenate kinase (PanK) are immobilized on the resin.

Compound 9: Kinase Reaction

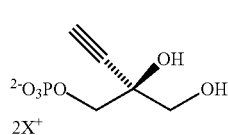

As shown in Scheme 3B, (S)-2-ethynyl-propane-1,2,3-triol 1-phosphate (9) is prepared by reacting pantothenate kinase (PanK) wild type from *E. coli* or a variant thereof, with compound (3) in a buffered solution adjusted as needed to a pH in a range from about 4 to 10, or particularly about 6.5 to 8.5 or more particularly 5.5 to 8.5 Any buffer having a suitable pH range can be used, for example but not limited to, sodium phosphate, PIPES, e.g. piperazine-N,N'-bis(2-ethanesulfonic acid); BIS-TRIS methane, e.g., 2-[Bis(2-hydroxyethyl)amino]-2-(hydroxymethyl)propane-1,3-diol; borate; HEPES, e.g., 4-(2-hydroxyethyl)-1-piperazineethanesulfonic acid or 2-[4-(2-hydroxyethyl)piperazin-1-yl]ethanesulfonic acid; triethanolamine and TRIS, e.g., tris(hydroxymethyl)aminomethane or 2-Amino-2-(hydroxymethyl)propane-1,3-diol, with sodium phosphate being preferred. The reaction can be performed in the presence of any suitable bi-valent metal salt, for example but not limited to a magnesium salt, for example magnesium chloride, and salts of cobalt, manganese, zinc or calcium.

This reaction utilizes adenosine 5'-diphosphate (ADP) as the phosphate source which requires regenerating to 5'-triphosphate (ATP). ATP can be generated in situ and subsequently regenerated by any method known in the art from ADP, adenosine 5'-monophosphate (AMP) or adenosine. For example, a combination of acetyl phosphate together with acetate kinase can be used for regenerating ADP to ATP. Alternatively, (a) a combination of pyruvate oxidase, catalase and acetate kinase in the presence of pyruvate, phosphate and oxygen can be used for regenerating ADP to ATP, or (b) a combination of pyruvate oxidase, catalase and acetate kinase in the presence of pyruvate, phosphate, and oxygen in combination with acetyl phosphate and acetate kinase can be used for ATP regeneration from ADP.

The reaction can be performed with a substrate concentration of about 10 to 100 g/L, and particularly about 20 to 40 g/L. The reaction can be run at a temperature from about 0 to 40° C., and particularly at about 10 to 25° C.

The reaction can also be performed with pantothenate kinase (PanK) immobilized on a resin, or with both PanK and acetate kinase immobilized on the resin. Any suitable enzyme immobilization method known in the art can be used, for example but not limited to, Immobilized Metal-Ion Affinity Chromatography (IMAC) resin, or an affinity resin-immobilization using other biological tags, co-valent immobilization, immobilization on ionic resins, immobilization by adsorption, encapsulation, and/or crosslinked enzymes. For example, the Metal-Ion Affinity Chromatography (IMAC) resin can be used, or any suitable combination of IMAC resin and bi-valent cation can be used wherein the cation can be, for example but not limited to, nickel, cobalt, copper, zinc, iron, and/or aluminum. Particularly, IMAC resin charged with nickel can be used. Preferably, both acetate kinase and pantothenate kinase (PanK) are immobilized on the resin.

Compound 5: Oxidase Reaction

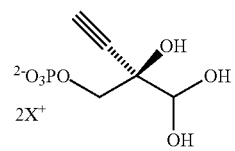

As shown in Scheme 3B, (R)-2-ethynyl-glyceraldehyde hydrate 3-phosphate (5) is prepared by reacting galactose oxidase with (S)-2-ethynyl-propane-1,2,3-triol 1-phosphate (9) in a buffered solution adjusted as needed to a pH in a range from about 3 to 10, or more particularly from about 6 to 8. Any buffer having a suitable pH range can be used, for example but not limited to, sodium phosphate; sodium acetate; PIPES, e.g. piperazine-N,N'-bis(2-ethanesulfonic acid); MOPS, e.g., 3-(N-morpholino)propanesulfonic acid or 3-morpholinopropane-1-sulfonic acid; HEPES, e.g., 4-(2-hydroxyethyl)-1-piperazineethanesulfonic acid or 2-[4-(2-hydroxyethyl)piperazin-1-yl]ethanesulfonic acid; TRIS, e.g., tris(hydroxymethyl)aminomethane or 2-Amino-2-(hydroxymethyl)propane-1,3-diol; and BIS-TRIS methane, e.g., 2-[Bis(2-hydroxyethyl)amino]-2-(hydroxymethyl)propane-1,3-diol; borate; CAPS, e.g., N-cyclohexyl-3-aminopropanesulfonic acid; MES, e.g. 2-(N-morpholino)ethanesulfonic acid; CHES, e.g., N-Cyclohexyl-2-aminoethanesulfonic acid; Glycine; or Bicine (N,N-Bis(2-hydroxyethyl)glycine); with sodium phosphate being preferred.

Copper and a peroxidase are both used in the reaction to activate galactose oxidase (GOase). Copper can be supplied to the reaction mixture by addition of $CuSO_4$, $Cu(OAc)_2$, $CuCl_2$ or other salts of Cu(II) or Cu(I). The peroxidase can be a horseradish peroxidase, or a peroxidase derived from other organisms, or it can replaced by an oxidant such as ferricyanide, iridate, manganese (III) salts, persulfate salts and other one electron or two electron oxidants, or inorganic or organic oxidants. Preferably, the peroxidase is a horseradish peroxidase. A catalase is also added to help prevent GOase deactivation. The catalase can be from a mammalian source (bovine) or from a bacterial or fungal source such as *Corynebacterium*, *Aspergillus* or other organisms known in the art for this purpose.

The reaction proceeds in the presence of oxygen. One convenient method is sparging the reaction with air. Alternatively, other systems to generate oxygen can employed, such as hydrogen peroxide/catalase, superoxide or use of other methods known in the art for this purpose.

The reaction can be performed with a substrate concentration of about 10 to 180 g/L, and particularly 20 to 50 g/L. The reaction can be run at a temperature from about 0 to 40° C., and particularly from about 10 to 30° C.

Compound 6: Deoxyribose-Phosphate Aldolase (DERA) Reaction

An important advantage of this new route for producing compound (6) over prior known processes is that it creates the sugar framework at the correct oxidation state without the use of protecting groups.

4-Ethynyl-D-2-deoxyribose 5-phosphate (6) is prepared by reacting deoxyribose-phosphate aldolase (DERA) with (R)-2-ethynyl-glyceraldehyde 3-phosphate (5) as an acid or salt thereof, and acetaldehyde in an aqueous solution adjusted as needed to a pH in a range from about 5 to 9, or more particularly about 6 to 8. Examples of salts of (5) include, but are not limited to, calcium, magnesium, zinc, mono- or di-Na salts, mono- or di-K salts, or mono- or di-Li salts; mono- or di-ammonium or salts; or mono-valent or di-valent salts with primary, secondary or tertiary amines. The reaction can be performed in an open vessel or is preferably performed in a sealed vessel to prevent evaporation of acetaldehyde.

The reaction can be performed with a substrate concentration of about 10 to100 g/L, particularly about 30 to 60 g/L. It can be run at a temperature from about 0 to 40° C., and particularly from about 25 to 35° C.

The reaction can be run without any buffers. Alternatively, buffers can be used, for example but not limited to, triethanolamine; phosphate; MOPS, e.g., 3-(N-morpholino)propanesulfonic acid or 3-morpholinopropane-1-sulfonic acid; HEPES, e.g., 4-(2-hydroxyethyl)-1-piperazineethanesulfonic acid or 2-[4-(2-hydroxyethyl)piperazin-1-yl]ethanesulfonic acid; BIS-TRIS methane, e.g., 2-[Bis(2-hydroxyethyl)amino]-2-(hydroxymethyl)propane-1,3-diol; borate; PIPES, e.g. piperazine-N,N'-bis(2-ethanesulfonic acid); MES, e.g., 2-(N-morpholino)ethanesulfonic acid; and borate; or other buffers having a suitable pH range which do not have any primary amine groups.

Each step and method of the processes described herein which comprise the use of one or more enzymes is performed at a temperature that does not denature said one or more enzymes. Each step and method of the processes described herein which comprise the use of one or more enzymes can be performed at a pH in a range from about 3 to 10 or from about 4 to 10.

A "nucleobase" (or"nitrogenous base" or "base") is a pyrimidine or purine heterocycle of nucleic acids such as DNA and RNA. As used herein, nucleobase includes adenine, guanine, cytosine, thymine or uracil, as well as nucleobases with non-natural modifications, for example, wherein the base has one or more non-natural substituents, or a modification affecting heteroatom(s) in a base excluding any change to the anomeric C—N linkage.

A 4'-ethynyl-2'-deoxy nucleoside contains a nucleobase. As used herein, an analog of a 4'-ethynyl-2'-deoxy nucleoside means a non-natural modification to the base of the nucleoside, for example wherein the base has one or more non-natural substituents, or a modification affecting heteroatom(s) in the base excluding any change to the anomeric C—N linkage.

As used herein, "phosphopentomutase" ("PPM") enzymes (e.g. EC 5.4.2.7) are enzymes that catalyze the reversible isomerization of ribose 1-phosphate to ribose 5-phosphate and related compounds such as deoxyribose phosphate and analogs of ribose phosphate and deoxyribose phosphate.

As used herein, "purine nucleoside phosphorylase" ("PNP") enzymes (EC 2.4.2.2) are enzymes that catalyze the reversible phosphorolysis of purine ribonucleosides and related compounds (e.g., deoxyribonucleosides and analogs of ribonucleosides and deoxyribonucleosides) to the free purine base and ribose-1-phosphate (and analogs thereof).

As used herein, "sucrose phosphorylase" ("SP") enzymes (EC 2.4.1.7) are enzymes that catalyze the reversible phosphorolysis of sucrose to D-fructose base and glucose-1-phosphate (and analogs thereof). Sucrose phosphorylase (SP) in combination with sucrose is employed in combination with purine nucleoside phosphorylase (PNP) and phosphomutase (PPM) to remove free phosphate ions from the reaction, where the combination of the enzymes catalyzes the formation of nucleoside MK-8591 (EFdA), while in some embodiments it could be replaced by other methods known in the art.

As used herein, "deoxyribose-phosphate aldolase" ("DERA") (e.g., EC 4.1.2.4) refers to an enzyme in a family of lyases that reversibly cleave or create carbon-carbon bonds. Deoxyribose-phosphate aldolases as used herein include naturally occurring (wild type) deoxyribose-phosphate aldolase as well as non-naturally occurring engineered polypeptides generated by human manipulation. The wild-type deoxyribose-phosphate aldolase catalyzes the reversible reaction of 2-deoxy-D-ribose 5-phosphate into D-glyceraldehyde 3-phosphate and acetaldehyde.

As used herein, "pantothenate kinase," ("PanK") refers to enzymes (EC 2.7.1.33) which in nature phosphorylate pantothenate to form 4'-phosphopantothenate. Variant enzymes derived from such PanK enzymes may display improved activity and stereoselectivity towards 3'OH— group of D-ethynylglyceraldehyde regardless of whether such variants retain their natural function towards pantothenate.

As used herein, "galactose oxidase" ("GOase"; EC 1.1.3.9) enzymes are copper-dependent enzymes, that, in the presence of bimolecular oxygen, catalyze the oxidation of primary alcohols to the corresponding aldehydes. They act in both regio- and enantiospecific manners, enabling synthetic approaches that require little or no functional group protection and yield the desired stereoisomer. The manner of oxidation is mild and controlled, such that activity does not lead to over-oxidation of the alcohol to its corresponding carboxylic acid.

As used herein, "horseradish peroxidase" (HRP, EC 1.11.1.7) enzyme is an iron-dependent enzyme that activates and maintains GOase catalytic activity by oxidizing an inactive redox state of the active site that occurs during normal GOase catalytic cycling. Type I HRP is employed in a catalytic manner in the examples included herein, however it is not meant to be exclusive in this role, as there are other electron-transferring enzymes that belong to this and other enzyme classes as well as chemical reagents that can fulfill this role.

As used herein, "catalase" refers to a heme-dependent enzyme (EC 1.11.1.6) which acts on hydrogen peroxide, a byproduct of galactose oxidase or pyruvate oxidase reactions, which can render the enzymes inactive above certain levels of hydrogen peroxide. Catalase is employed as a catalytic maintenance enzyme in the examples herein to convert hydrogen peroxide to water and oxygen, while in some embodiments it could be replaced by other methods, such as electrochemical decomposition of hydrogen peroxide. A heme-dependent catalase is employed in a catalytic manner in the examples included herein, however it is not meant to be exclusive in this role, as there are other enzymes that belong to this class that can fulfill this role.

As used herein, "acetate kinase" ("AcK") refers to an enzyme (EC 2.7.2.1), which catalyzes the formation of acetyl phosphate from acetate and adenosine triphosphate (ATP). It can also catalyze the reverse reaction, where it phosphorylates adenosine 5'-diphosphate (ADP) to adenosine 5'-triphosphate (ATP) in the presence of acetyl phosphate. Acetate kinase is employed to recycle ATP required by pantothenate kinase (PanK) in the examples herein, while in some embodiments the acetyl phosphate-acetate kinase recycling combination could be replaced by other methods known in the art.

As used herein, "pyruvate oxidase" ("PO") refers to an enzyme (EC 1.2.3.3) dependent on Flavin adenine dinucleotide (FAD) and Thiamin diphosphate. Pyruvate oxidase is an enzyme belonging to the family of oxidoreductases, specifically those acting on the aldehyde or oxo group of a donor with oxygen as acceptor and it catalyzes the chemical reaction between pyruvate, phosphate ion and bimolecular oxygen to form acetyl phosphate, carbon dioxide and hydrogen peroxide. Pyruvate oxidase (PO) is employed in combination with acetate kinase (AcK) and catalase as a catalytic ATP-regenerating combination in the examples herein, where the combination of the enzymes catalyzes the formation of ATP from ADP in the presence of oxygen, pyruvate and phosphate ions, while in some embodiments it could be replaced by other methods known in the art.

As used herein, "wild-type" and "naturally-occurring" enzyme refers to the form found in nature. For example, a wild-type polypeptide sequence is a sequence present in an organism that can be isolated from a source in nature and which has not been intentionally modified by human manipulation.

As used herein, "engineered," "variant," "mutant" and "non-naturally occurring" when used with reference to an enzyme including a polypeptide, refers to a material, or a material corresponding to the natural or native form of the material, that has been modified in a manner that would not otherwise exist in nature. In some embodiments, the polypeptide is identical to a naturally occurring polypeptide, but is produced or derived from synthetic materials and/or by manipulation using recombinant techniques.

"Percentage of sequence identity," "percent identity," and "percent identical" with respect to enzymes are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation € of 10, M=5, N=-4, and a comparison of both strands. For amino acid sequences, the BLASTP program uses as defaults a wordlength (W) of 3, an expectation €(E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelerys, Madison WI), using default parameters provided.

"Substantial identity" refers to a polynucleotide or polypeptide sequence that has at least 85%, 86%, 87%, 88%, 89%, 90%, 91%, 92%, 93%, 94%, 95%, 96%, 97%, 98%, 99%, or more sequence identity, as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

The phrase "suitable reaction conditions" refers to those conditions in the enzymatic conversion reaction solution (e.g., ranges of enzyme loading, substrate loading, temperature, pH, buffers, co-solvents, etc.) under which each polypeptide used in the present invention is capable of converting a substrate to the desired product compound. Some exemplary suitable reaction conditions are provided herein.

As used herein, "substrate" in the context of an enzymatic conversion reaction process refers to the compound or molecule acted on by the engineered enzymes used herein.

As used herein, "product" in the context of an enzymatic conversion process refers to the compound or molecule resulting from the action of an enzymatic polypeptide on a substrate.

As used herein, "increasing" yield of a product (e.g., a 4'-ethynyl-2'-deoxyribose phosphate analog or 4'-ethynyl-2'-deoxy nucleoside analog) from a reaction occurs when a particular component present during the reaction (e.g., an enzyme) causes more product to be produced, compared with a reaction conducted under the same conditions with the same substrate but in the absence of the component of interest.

As used herein, "equilibration" or "equilibrium" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

"Enantiomeric excess" (ee) is a measurement of purity used for chiral substances. It reflects the degree to which a sample contains one enantiomer in greater amounts than the other. For example, a racemic mixture has an e.e. of 0%, while a single completely pure enantiomer has an e.e. of 100%; and a sample with 70% of one enantiomer and 30% of the other has an e.e. of 40% (70%–30%). Diastereomer excess (de) is calculated the same way as e.e. when only two diastereoisomers are present in the mixture.

"Protein", "enzyme," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

As used herein, the term "about" means an acceptable error for a particular value. In some instances "about" means within 0.05%, 0.5%, 1.0%, or 2.0% at the lower end and the upper end of given value range. With respect to pH, "about" means plus or minus 0.5.

As used herein, "substantially pure" polypeptide or "purified" protein refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. However, in some embodiments, the composition comprising the polypeptide comprises polypeptide that is less than 50% pure (e.g., about 10%, about 20%, about 30%, about 40%, or about 50%). Generally, a substantially pure polypeptide composition comprises about 60% or more, about 70% or more, about 80% or more, about 90% or more, about 95% or more, and about 98% or more of all macromolecular species by mole or % weight present in the composition. In some embodiments, the polypeptide is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated polypeptides are substantially pure polypeptide compositions.

As used herein, "improved property" of an enzyme refers to at least one improved property of an enzyme. In some embodiments, the present invention employs engineered PPM, PNP, DERA, PanK, AcK, SP and/or GOase polypeptides that exhibit an improvement in any enzyme property as compared to a reference PPM, PNP, DERA, PanK, AcK, SP or GOase polypeptide, respectively, and/or a wild-type PPM, PNP, DERA, PanK, AcK, SP or GOase polypeptide, respectively, and/or another engineered PPM, PNP, DERA, PanK, AcK, SP or GOase polypeptide, respectively. Thus, the level of "improvement" can be determined and compared between the various polypeptides, including wild-type, as well as engineered polypeptides. Improved properties include, but are not limited, to such properties as increased protein expression, increased production of the intended product, increased substrate specificity or affinity (i.e., increased activity on the substrate), increased thermoactivity, increased thermostability, increased pH activity, increased stability, increased enzymatic activity, increased specific activity, increased resistance to substrate or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, and altered temperature profile. In additional embodiments, the term is used in reference to the at least one improved property of PPM, PNP, DERA, PanK, AcK, SP and/or GOase enzymes. In some embodiments, the present invention employs engineered PPM, PNP, DERA, PanK, AcK, SP and/or GOase polypeptides that exhibit an improvement in any enzyme property as compared to a reference PPM, PNP, DERA, PanK, AcK, SP and/or GOase polypeptide, respectively; and/or a wild-type polypeptide, and/or another engineered PPM, PNP, DERA, PanK, AcK, SP and/or GOase polypeptide, respectively. Thus, the level of "improvement" can be determined and compared between the various polypeptides, including wild-type, as well as engineered polypeptides.

As used herein, "conversion" ("cony" or "conv.") refers to the enzymatic conversion (or biotransformation) of a substrate(s) to the corresponding product(s). "Percent" conversion refers to the percent of the substrate that is converted to the product within a period of time under specified conditions. Thus, the "enzymatic activity" or "activity" of a polypeptide can be expressed as percent conversion of the substrate to the product in a specific period of time.

As used herein, "stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess ("e.e.") calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess ("de."). Enantiomeric excess and diastereomeric excess are types of stereomeric excess.

The present process invention encompasses the use of engineered PPM, PNP, DERA, PanK, AcK, SP and GOase polypeptides, particularly those having SEQ ID NO.s 1 to 21, and said sequences which comprise one or more conservative amino acid substitutions which may be referred to as conservatively modified variants of each of SEQ ID NO.s 1 to 21.

As used herein, "conservative" amino acid substitution and refers to substitutions of amino acids in a protein with other amino acids having similar characteristics (e.g. acidic, basic, positively or negatively charged, polar or non-polar, side-chain size, hydrophobicity/hydrophilicity, backbone conformation and rigidity, etc.), such that the changes can frequently be made without altering the biological activity of the protein. This includes one or more substitutions of an amino acid in the polypeptide with a different amino acid within the same or similar defined class of amino acids. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. By way of example and not limitation, in some embodiments, an amino acid with an aliphatic side chain is substituted with another aliphatic amino acid (e.g., alanine, valine, leucine, and isoleucine); an amino acid with an hydroxyl side chain is substituted with another amino acid with an hydroxyl side chain (e.g., serine and threonine); an amino acid having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively. Additional exemplary conservative amino acid substitutions are set forth in Table 1.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions.

A "functional fragment" refers to a polypeptide that has an amino-terminal and/or carboxy-terminal deletion(s) and/or internal deletions, but where the remaining amino acid sequence is identical to the corresponding positions in the sequence to which it is being compared (e.g., a full-length engineered PPM, PNP, DERA, PanK, AcK, SP or GOase enzyme used in the present invention) and that retains substantially all of the activity of the full-length polypeptide.

As used herein, "deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered PPM, PNP, DERA, PanK, AcK, SP or GOase enzyme. Deletions can be directed to the internal portions and/or terminal portions of the polypeptide. In various embodiments, the deletion can comprise a continuous segment or can be discontinuous. Deletions are typically indicated by "-" in amino acid sequences.

As used herein, "insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

Additional acronyms and abbreviations used herein are as follows:

| LC-MS | liquid chromatography mass spectrometry |
|---|---|
| THF | tetrahydrofuran |
| NMR | nuclear magnetic resonance spectroscopy |
| RT or rt | room temperature (ambient, about 25° C.) |
| sccm | standard cubic centimeter per minute |
| rpm | revolutions per minute |
| M | mole/molarity |
| mM | millimolar |
| μL | microliter(s) |
| DMSO | dimethyl sulfoxide |
| TsOH | p-toluenesulfonic acid |
| Bn | benzyl |

| | |
|---|---|
| CPME | Cyclopentyl methyl ether |
| MTBE | methyl tert-butyl ether |
| HR-MS | High Resolution Mass Spectrometry |
| g/L | gram(s) per liter |
| mL | milliliter(s) |
| mmol | millimole |
| mg | milligram |
| kg | kilogram |
| N | Normal |
| conv | conversion |
| NMR | nuclear magnetic resonance |
| aq | aqueous |
| hr, h | hour(s) |
| HPLC | high performance liquid chromatography |
| DCM | dichloromethane |
| 2-MeTHF | 2-Methyltetrahydrofuran |
| ESI | Electrospray ionization |

Experimental Procedures

Preparation of 2-ethynyl-2-hydroxypropane-1,3-diyl diacetate (2)

Method A

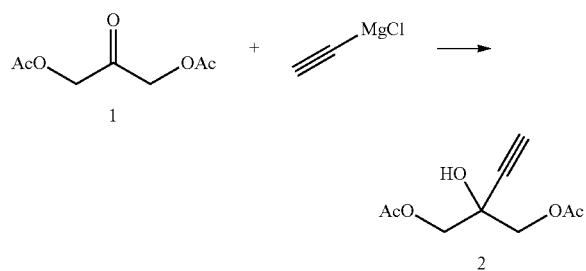

To a −35° C. solution of diacetoxyacetone (1) (159 g, 914.0 mmol) in THF (1000 mL) was added 1600 mL of a 0.5 M solution of ethynyl magnesium chloride in THF maintaining the temperature below −20° C. After the reaction reached completion, acetic acid (78 mL) in 400 mL methyl tert-butyl ether (MTBE) was added dropwise keeping the temperature below −20° C. MTBE (800 mL) was then added and the mixture was warmed to room temp. Saturated NaCl in water (1000 mL) was added followed by saturated NH$_4$Cl solution in water (1050 mL). The organic layer was separated, dried over Na$_2$SO$_4$ and evaporated to give compound (2) as an oil (160 g, 88%). $^1$H NMR (CDCl$_3$, 500 MHz): δ 4.26 (dd, 4H), 2.55 (s, 1H), 2.14 (s, 6H).

Preparation of 2-ethynyl-propane-1,2,3-triol (3)

Method B

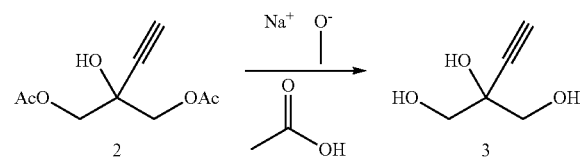

To a solution of 2-ethynyl-2-hydroxypropane-1,3-diyl diacetate (2) (70 g, 350 mmol) in ethanol was added a 0.5M solution of sodium methoxylate in methanol (69.9 mL, 35.0 mmol) at room temperature (rt). The reaction was stirred at rt for 2 hours (h) to reach completion. The solvents were evaporated and the residue was re-dissolved in 100 mL water and extracted with 3×50 mL MTBE. The aqueous layer was sparged with nitrogen to remove residual solvents to give a 40.9% solution of 2-ethynyl-propane-1,2,3-triol (3) (108 g, 100% yield) as determined by nuclear magnetic resonance (NMR) (maleic acid as internal standard). $^1$H NMR (D$_2$O, 500 MHz): δ 3.60 (dd, 4H), 2.85 (s, 1H).

Alternate Preparations of (R)-2-ethynyl-glyceraldehyde (4)

Method C1

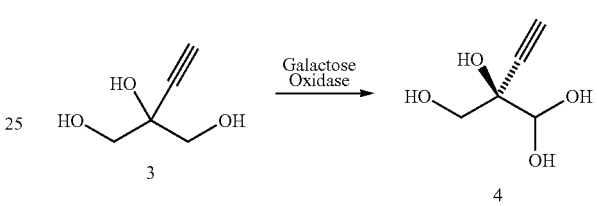

In a stirred reactor, 2-ethynyl-propane-1,2,3-triol (3) (1.1 g, 9.47 mmol) in sodium phosphate buffer (30 mL, 100 mM, pH 7.0) containing antifoam 204 (Sigma A6426, 1 drop ~20 μL) was warmed to 30° C. with air sparging at 12.5 sccm. Galactose oxidase (GOase, SEQ ID NO.: 1) (250 mg), Horseradish Peroxidase* (Type I, 5 mg) and bovine catalase** (5 mg) dissolved in sodium phosphate buffer (5 mL 100 mM, pH 7.0) were added to the reactor, followed by the addition of CuSO$_4$ aq. solution (100 mM, 150 μL). The reaction mixture was stirred at 600 rpm with air sparging for 47h to give (R)-2-ethynyl-glyceraldehyde (4) in 47% conversion (by NMR) and 72% e.e. (The product was not isolated). $^1$H NMR (D$_2$O, 500 MHz): δ 4.29 (s, 1H), 3.65 (dd, 2H), 2.83 (s, 1H).

*Horse Radish Peroxidase: wild type peroxidase from horseradish Type I, commercially available from SIGMA (P8125), isolated from horseradish roots (*Amoracia rusticana*).
**Bovine catalase: heme-dependent catalase from bovine source, commercially available from Sigma (C1345)

Method C2

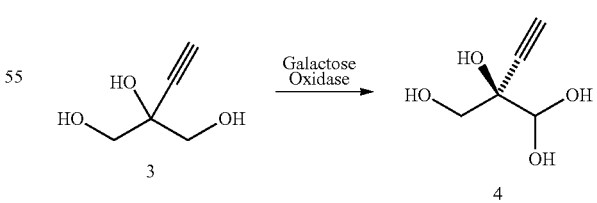

In a stirred 100 L jacketed reactor charged with deionized water (56.2 kg), sodium dihydrogen phosphate (1.212 kg, 10 moles) was added. The pH was adjusted to 7.02 using 10 N sodium hydroxide solution (852.6 g) at 25° C. The reactor was charged with Antifoam 204 (A6426, 10 mL), followed CuSO4.5H$_2$O (6.5 g). Galactose oxidase (451.2 g) (SEQ ID NO.: 10) was added and stirred for 15 min while sparged with air. Horseradish peroxidase* (200.2 g) and catalase** (502.6 g) were added and the reactor was rinsed with water (2.0 kg). Next 2-ethynyl-propane-1,2,3-triol (3) solution in water (9.48%, 30.34 kg, 24.72 mol) was added followed by an additional portion of Antifoam 204 (A6426, 10 mL). The reaction was sparged with air and stirred overnight to give 94.0 kg of (R)-2-ethynyl-glyceraldehyde (4) in 66% conversion (by NMR) and 84% e.e. Assay yield 60%: 1H NMR (D$_2$O, 500 MHz): δ 4.29 (s, 1H), 3.65 (dd, 2H), 2.83 (s, 1H).

*Horse Radish Peroxidase: wild type peroxidase from horseradish purified, commercially available from Toyobo (PEO-301), isolated from horseradish roots (*Amoracia rusticana*).

**Bovine catalase: heme-dependent catalase from bovine source, commercially available from Sigma (C1345).

The above reaction was also performed using the galactose oxidase (SEQ ID NO.: 11) and the product (4) was obtained in 67% conversion (by NMR) and 88% e.e. and assay yield 59%: $^1$H NMR (D$_2$O, 500 MHz): δ 4.29 (s, 1H), 3.65 (dd, 2H), 2.83 (s, 1H).

Method C3

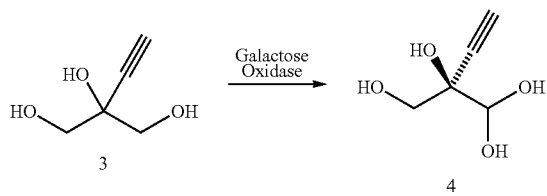

In a 100 mL EasyMax vessel equipped with sparger and flow controller, water (82 mL) and PIPES potassium buffer (5 mL, 0.5 M) were charged. The pH was adjusted to 7.5 using 5 M KOH solution at 25° C. Antifoam 204 (200 μL) was added, followed by evolved galactose oxidase (SEQ ID NO.: 17, 450 mg enzyme powder) and copper(II) sulfate pentahydrate (100 μL, 100 mM). The reaction mixture was sparged with air at 125 standard cubic centimeters per minute (sccm) for 15 min. Bovine catalase (C1345, Sigma-Aldrich, 150 mg, 2000-5000 U/mg, 0.75 MU) was charged, followed by horseradish peroxidase (HRP, Toyobo PEO-301, 100 mg, 130 U/mg, 1.3 kU) and the aqueous solution of 2-ethynyl-propane-1,2,3-triol (3) (25 wt %, 12 mL, 25.8 mmol). The reaction mixture was stirred at 30° C. with aeration at 125 sccm and sampled using EasySampler over 20 h to give 70% conversion and form compound (4) ((R)-2-ethynyl-glyceraldehyde) in 58% assay yield and 99% e.e. $^1$H NMR (D$_2$O, 500 MHz): δ 4.29 (s, 1H), 3.65 (dd, 2H), 2.83 (s, 1H). The crude reaction stream was carried directly into the subsequent phosphorylation step.

Method C4: Oxidation With Immobilized Galactose Oxidase

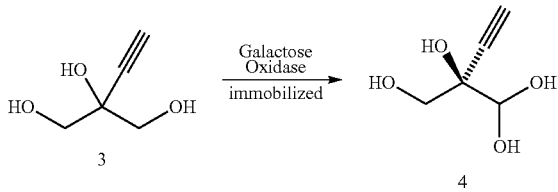

Enzyme Immobilization Procedure

Nuvia IMAC Ni-charged resin (16 mL based on settled volume) was added to a filter funnel and washed with binding buffer (10 column volumes, 160 mL; 500 mM sodium chloride, 50 mM sodium phosphate, 15 mM imidazole, pH 8.0) to remove the resin storage solution. In a vessel evolved galactose oxidase (SEQ ID NO.: 17, 2.00 g) lyophilized powders were resuspended in copper (II) sulphate solution (100 μM; 5.00 mL), followed by addition of binding buffer (50 mL) and the resin. The solution was mixed using rotating mixer at 20° C. for 5 h. The resin was filtered and washed with binding buffer (10 column volumes, 160 mL) and potassium PIPES buffer (10 column volumes, 160 mL; 50 mM, pH 7.5) and it was used directly in a reaction.

Reaction Procedure

In a 100 mL EasyMax vessel equipped with sparger and flow controller, water (82 mL) and PIPES potassium buffer (5 mL, 1 M) were charged. The pH was adjusted to 7.5 using 5 M KOH solution at 25° C. Antifoam 204 (200 μL) was added, followed by evolved galactose oxidase immobilized on the resin (SEQ ID NO.: 17, 750 mg enzyme powder per 6 mL resin) and copper(II) sulfate pentahydrate (100 μL, 100 mM). The reaction mixture was sparged with air at 125 standard cubic centimeters per minute (sccm) for 15 min. Bovine catalase (C1345, Sigma-Aldrich, 210 mg, 2000-5000 U/mg, 1.05 MU) was charged, followed by horseradish peroxidase (HRP, Toyobo PEO-301, 100 mg, 130 U/mg, 1.3 kU) and the aqueous solution of 2-ethynyl-propane-1,2,3-triol (3) (25 wt %, 13 mL, 29.4 mmol). The reaction mixture was stirred at 25° C. with aeration at 125 sccm. After 22h the reaction reached 91% conversion to give 200 mM (R)-2-ethynyl-glyceraldehyde (4) solution (100 mL, 68% assay yield, 97% e.e. $^1$H NMR (D$_2$O, 500 MHz): δ 4.29 (s, 1H), 3.65 (dd, 2H), 2.83 (s, 1H). The crude reaction stream was carried directly into the subsequent phosphorylation step.

Method C5: Optional Isolation of Aldehyde Via Formation of Animal (8)

Step 1: Preparation of (S)-2-(1,3-dibenzylimidazolidin-2-yl)but-3-yne-1,2-diol

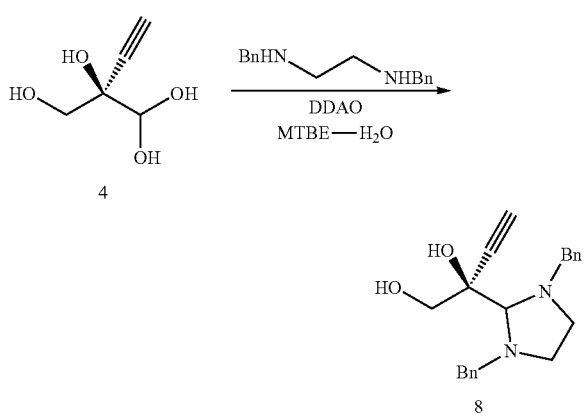

A 100 L jacketed cylindrical vessel equipped with nitrogen bubbler, mechanical stirrer and thermocouple was charged with crude oxidase reaction stream containing (R)-

2-ethynyl-glyceraldehyde ((4), 26.0 kg, 1.85 wt % aldehyde, 3.64 mol) and inerted with $N_2$ atmosphere. The aqueous solution was warmed to 20° C. and N,N-dimethyldodecan-1-amine oxide (DDAO) (30 wt % in water, 798 g, 0.96 mol) was added, followed by MTBE (55.3 kg, 76 L) and N,N'-dibenzylethane-1,2-diamine (1.55 kg, 6.43 mol). The brown, biphasic mixture was stirred overnight at 20° C. under nitrogen atmosphere. After 17 hours the stirring was stopped and the organic phase was removed and discarded. A light brown MTBE solution of (S)-2-(1,3-dibenzylimidazolidin-2-yl)but-3-yne-1,2-diol (56.5 kg, 2.02 wt % animal, 3.39 mmol, 93% assay yield) was obtained.

Six similar MTBE solutions were processed together in a single distillation and crystallization step (in total 374.4 kg of solution, containing 7.91 kg animal).

A 50 L jacketed cylindrical vessel equipped with mechanical stirrer, distillation head (condenser at −20° C.) and thermocouple was charged with animal solution (45 L). Vacuum was applied to the vessel (65-95 torr) and the jacket was set to 40° C. Solvent was removed by distillation until a volume of 35 L had been reached. At this point, the internal temperature was 6.1° C. and an off-white solid had begun to crystallize. The remaining MTBE solution was slowly added, maintaining a constant volume of 35-40 L and an internal temperature of 0-10° C. Once all the MTBE solution had been added the volume was decreased to 25 L. Distillation was halted, the vessel was inerted with nitrogen and the jacket temperature was decreased to 10° C. The resulting pale yellow suspension was aged at this temperature for 2 hours and the solids were collected by filtration. The filter cake was washed with cold (−2° C.) MTBE (12.7 kg) and then dried under nitrogen flow for 7 hours. (S)-2-(1,3-dibenzylimidazolidin-2-yl)-but-3-yne-1,2-diol was obtained as an off-white crystalline solid (5.75 kg). 1H NMR (500 MHz, DMSO-$d_6$) δ 7.42-7.35 (m, 4H), 7.32 (td, J=7.5, 1.6 Hz, 4H), 7.27-7.21 (m, 2H), 5.10 (t, J=5.6 Hz, 1H), 5.03 (s, 1H), 4.28 (d, J=13.3 Hz, 1H), 4.16 (d, J=13.3 Hz, 1H), 3.76 (s, 1H), 3.70-3.58 (m, 4H), 3.21 (d, J=0.9 Hz, 1H), 2.90-2.80 (m, 2H), 2.60-2.51 (m, 2H). $^{13}$C NMR (126 MHz, DMSO-$d_6$) δ 140.0, 140.0, 128.5, 128.3, 128.2, 128.1, 126.8, 126.8, 88.6, 86.9, 75.0, 74.0, 66.4, 60.7, 60.5, 50.4, 50.3, 39.5. HR-MS (ESI) Animal (M+H$^+$) $C_{21}H_{25}N_2O_2^+$ calculated 337.1911; found 337.1922.

Step 2: Preparation of (R)-2-ethynyl-glyceraldehyde (4) from animal (8)

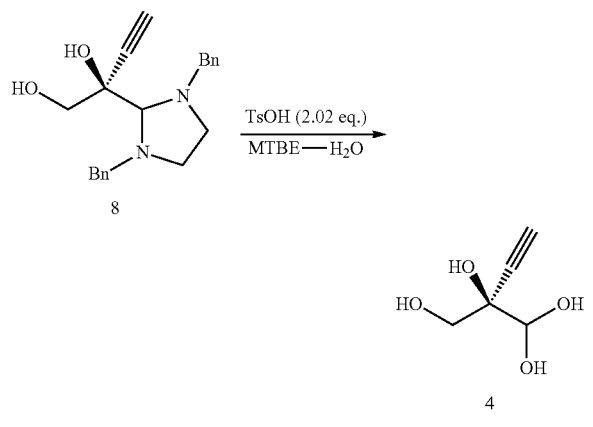

A 4 L jacketed cylindrical vessel equipped with nitrogen bubbler and mechanical stirrer was charged with of TsOH.H$_2$O (12.0 g, 63.1 mmol), water (60 mL), (S)-2-(1,3-dibenzylimidazolidin-2-yl)but-3-yne-1,2-diol (110 g, 327 mmol) and MTBE (1700 mL). The biphasic mixture was placed under nitrogen and the jacket temperature was set to 15° C. A solution of TsOH.H2O (114 g, 599.3 mmol) in water (600 mL) was added dropwise over 1.5 hours with overhead stirring (200 rpm). After addition had completed, the jacket temperature was lowered to 5° C. and the resulting slurry was aged for 1 hour. The solids were removed by filtration and washed with cold water (270 mL). The biphasic solution was transferred to a separating funnel and the organic phase was removed and discarded. The aqueous phase was treated with DOWEX™ MARATHON™ A resin (hydroxide form, 11.0 g) and AMBERLYST® 15 resin (hydrogen form, 11.0 g) while sparging with N$_2$ at a rate of 200 sccm for 24 hours to remove residual MTBE. The resins were removed by filtration to give a colorless aqueous solution of (R)-2-hydroxy-2-(hydroxymethyl)but-3-ynal (774 g, 4.6 wt % aldehyde, 82% yield). 1H NMR (500 MHz, D$_2$O) δ 5.01 (s, 1H), 3.77 (d, J=11.7 Hz, 1H), 3.73 (d, J=11.7 Hz, 1H), 2.92 (s, 1H). 13C NMR (126 MHz, D$_2$O) δ 129.4, 125.4, 90.3, 81.0, 76.0, 73.9, 65.3. HRMS (ESI) Aldehyde dimer (2M+Na$^+$) $C_{10}H_{12}NaO_6^+$ calculated 251.0526; found 251.0530.

Alternate Preparations of (R)-2-ethynyl-glyceraldehyde 3-phosphate (5)

Method D1: Acetate Kinase: ATP-Regeneration System

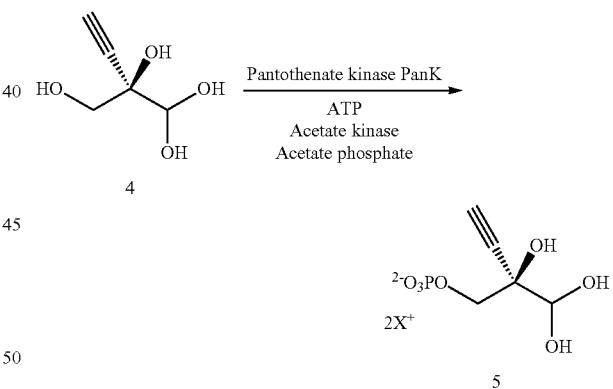

In a stirred reactor, to a solution of adenosine diphosphate disodium salt (40 mg, 0.087 mmol) and magnesium chloride (38 mg, 0.400 mmol) in HEPES buffer (66 mM, pH 7.5, 30 mL) was added (R)-2-ethynyl-glyceraldehyde (4) (1.9 mL, 210 g/L solution in water, 3.51 mmol), followed by acetate kinase (SEQ ID NO.: 3) (40 mg), and pantothenate kinase (SEQ ID NO.: 2) (120 mg). The reaction mixture was warmed to 25° C. and a solution of acetyl phosphate lithium potassium salt (1.3 g, 7.01 mmol) in HEPES buffer (50 mM, pH 7.5, 10 mL) was added dropwise over 4 hours, with pH maintained at 7.5 using 5M sodium hydroxide. The reaction was stirred for 18 hours to give (R)-2-ethynyl-glyceraldehyde 3-phosphate (5) in 85% conversion (by HPLC) (The product was not isolated). 1H NMR (D$_2$O, 400 MHz): δ 5.02

(s, 1H), 4.00 (dq, 2H), 2.88 (s, 1H). LC-MS: (ES, m/z): calculated for $C_5H_7O_6P$ (M−H): 193.1; found 193.0.

Method D2: Pyruvate Oxidase ATP-Regeneration System

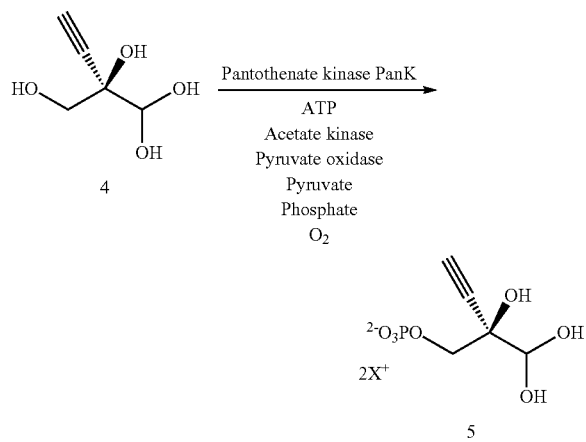

In a stirred reactor, a solution of sodium pyruvate (3.11 g, 28 mmol) and phosphoric acid (0.523 mL, 7.71 mmol) in 76 mL water pH 7.5 was charged with (R)-2-ethynyl-glyceraldehyde (4) (3.8 mL, 210 g/L solution in water, 7.01 mmol), adenosine diphosphate disodium salt (80 mg, 0.174 mmol), thiamine pyrophosphate (40 mg, 0.086 mmol), flavin adenine dinucleotide disodium salt hydrate (64 mg, 0.077 mmol), and magnesium chloride (400 μL, 1 M solution in water, 0.4 mmol). The pH was re-adjusted to 7.5 with 5M aq sodium hydroxide and the reaction volume was re-adjusted to 80 mL with water. Acetate kinase (SEQ ID NO.: 3) (80 mg), pyruvate oxidase (SEQ ID NO.: 4) (80 mg, lyophilized cell free extract), pantothenate kinase (SEQ ID NO.: 2) (400 mg), and catalase (800 μL, ammonium sulfate suspension CAT-101, Biocatalytics) were added. The reaction was stirred at 500 rpm and 30° C. with air sparging for 72 hours to give (R)-2-ethynyl-glyceraldehyde 3-phosphate 5 in 95% conversion (by HPLC) (The product was not isolated). 1H NMR ($D_2O$, 400 MHz): δ 5.02 (s, 1H), 4.00 (dq, 2H), 2.88 (s, 1H). LC-MS: (ES, m/z): calculated for $C_5H_7O_6P$ (M−H): 193.1; found 193.0.

The above reaction was also performed using the pantothenate kinase (SEQ ID NO.: 13) and the product 5 was obtained in 66% conversion. (The product was not isolated). $^1H$ NMR ($D_2O$, 400 MHz): δ 5.02 (s, 1H), 4.00 (dq, 2H), 2.88 (s, 1H).

Method D3: Acetate Kinase: ATP-Regeneration System Using Immobilized Enzymes

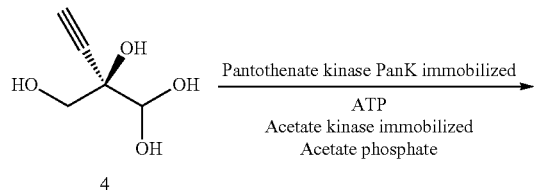

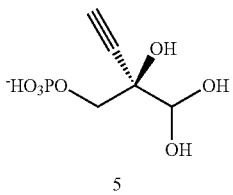

Enzyme Immobilization Procedure

NUVIA™ Immobilized Metal-ion Affinity Chromatography (IMAC) nickel-charged resin (168 mL based on settled volume) was added to a filter funnel and washed with binding buffer (1.6 L; 500 mM sodium chloride, 50 mM sodium phosphate, pH 8.0). In a vessel, pantothenate kinase (8.4 g) (SEQ ID NO.: 12) and acetate kinase (2.8 g) (SEQ ID NO.: 3) were dissolved in binding buffer (500 mL). The washed resin was charged to the vessel and the solution was stirred for 4 hours at 20° C. The resin was filtered and washed first with binding buffer (1.6 L) followed by piperazine-N,N'-bis(2-ethanesulfonic acid) (PIPES) buffer (840 mL; 50 mM, pH 6.5). The washed resin was used directly in the next step.

Reaction Procedure

To a 1 L reactor, a solution of (R)-2-ethynyl-glyceraldehyde (4) in water (608.7 g, 4.6 wt %, 212 mmol) was charged and cooled to 5° C. To the cooled solution piperazine-N,N'-bis(2-ethanesulfonic acid) (PIPES) buffer (32.7 mL, 1 M, pH 6.5, 32.7 mmol), magnesium chloride (9.33 mL, 1 M, 9.33 mmol), acetyl phosphate diammonium salt (51.8 g, 265 mmol), adenosine diphosphate disodium salt hydrate (1.17 g, 2.12 mmol), and water (192 mL) were added. The solution was allowed to stir and pH was adjusted to 6.4 using 5 N KOH. The reaction was warmed to 20° C. and 168 mL of resin with co-immobilized pantothenate kinase (SEQ ID NO.: 12) and acetate kinase (SEQ ID NO.: 3) was added. The reaction was stirred for 10 hours with 5 N KOH used to maintain a pH of 6.4 to give (R)-2-ethynyl-glyceraldehyde 3-phosphate (5) in 92% conversion (by HPLC) and 91% yield (by $^{31}P$ NMR with tetraphenylphosphonium chloride as internal standard) (the product was not isolated). $^1H$ NMR ($D_2O$, 400 MHz): δ 5.02 (s, 1H), 4.00 (dq, 2H), 2.88 (s, 1H). LC-MS: (ES, m/z): calculated for $C_5H_7O_6P$ (M−H): 193.1; found 193.0.

Preparation of 4-ethynyl-D-2-deoxyribose 5-phosphate (6)

Method E

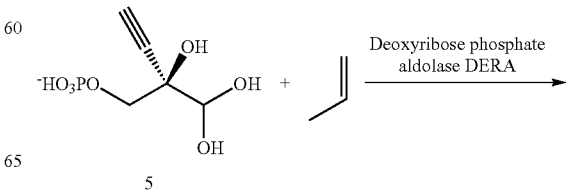

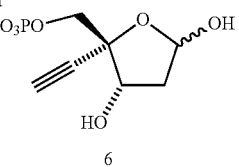

To a solution of (R)-2-ethynyl-glyceraldehyde 3-phosphate (5) (5, 20 mL, 5.3 mmol) in water, a solution of acetaldehyde in water (40 wt. %, 2.02 mL, 15.9 mmol) was added at room temperature, followed by the addition of Deoxyribose-phosphate aldolase (DERA) (SEQ ID NO.: 6), 25 mg solution in triethanolamine hydrochloride buffer (1 mL, 1 M, pH 7.0). The reactor was sealed and the mixture was stirred overnight at 30° C. and 600 rpm to give 4-ethynyl-D-2-deoxyribose 5-phosphate (6) in 99% conv. and 99% e.e., 99% d.e. as a 1:1 anomer mixture (The product was not isolated). α-anomer: $^1$H NMR (D$_2$O, 600 MHz) δ 5.31 (t, 1H), 4.13 (t, 1H), 3.81-3.72 (m, 2H), 2.89 (s, 1H), 2.42-2.34 (m, 1H), 1.87-1.79 (m, 1H); $^{13}$C NMR (D$_2$O, 151 MHz) δ 97.7 (s), 81.4 (d), 79.4 (s), 78.9 (s), 71.1 (s), 67.7 (d), 39.6 (s). β-anomer: 1H NMR (D$_2$O, 600 MHz) δ 5.40 (dd, 1H), 4.28 (t, 1H), 3.88-3.80 (m, 2H), 2.87 (s, 1H), 2.13-2.06 (m, 1H), 2.04-1.97 (m, 1H); 13C NMR (D$_2$O, 151 MHz) δ 97.3 (s), 82.2 (d), 78.7 (s), 78.5 (s), 71.3 (s), 68.4 (d), 39.6 (s). LC-MS: (ES, m/z): calculated for C$_7$H$_{10}$O$_7$P (M−H): 237.0; found 237.0

Alternate Preparations of (2R,3S,5R)-5-(6-amino-2-fluoro-9H-purin-9-yl)-2-ethynyl-2-(hydroxymethyl)tetrahydrofuran-3-ol monohydrate (7) [alternative name 4'-ethynyl-2-fluoro-2'-deoxyadenosine or EFdA]

Method F1

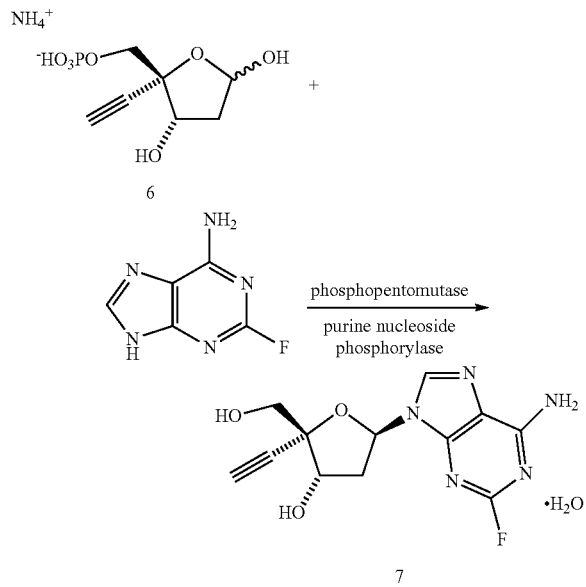

Ammonium ((2R,3S)-2-ethynyl-3,5-dihydroxytetrahydrofuran-2-yl)methyl hydrogen phosphate (1.00 g, 3.91 mmol) was dissolved in 10 mL of pH 7.5 buffer (100 mM triethanolamine•HCl containing 5 mM MnCl$_2$). The solution pH was adjusted to 7.3 with 5 N NaOH. To the solution was added 2-fluoroadenine (0.599 g, 3.91 mmol) and sucrose (2.68 g, 7.82 mmol). The enzyme solution was prepared by dissolving phosphopentomutase (SEQ ID NO.: 8) (100 mg), purine nucleoside phosphorylase (SEQ ID NO.: 9) (50 mg), and sucrose phosphorylase (SEQ ID NO.: 7) (10 mg) in 10 mL of the pH 7.5 buffer. The enzyme solution was added to the reagent mixture and the resulting suspension was shaken at 40° C. After 20 h, the suspension was cooled to 0° C. and filtered, rinsing with cold water. The solid was suction dried to give the title compound (1.12 g, 92%) as a single isomer.

1H NMR: (300 MHz, DMSO-d6, ppm): δ 7.68 (br s, 2H), 7.32 (d, J=2.0 Hz, 1H), 6.44 (t, J=5.8 Hz, 1H), 5.52 (d, J=5.6 Hz, 1H), 5.27 (t, J=6.0 Hz, 1H), 4.44 (q, J=6.4 Hz, 1H), 3.60 (q, J=6.0 Hz, 1H), 3.53 (q, J=6.4 Hz, 1H), 3.48 (s, 1H), 2.48-2.41 (m, 1H), 2.37-2.30 (m, 1H). 13C NMR (150.92 MHz, DMSO-d6, ppm) δ 158.5 (d, JCF=203.5), 157.6 (d, JCF=21.2), 150.2 (d, JCF=20.2), 139.7 (d, JCF=2.4), 117.4 (d, JCF=4.0), 85.1, 82.0, 81.4, 78.7, 70.1, 64.2, 38.1. LC-MS: (ES, m/z): calculated for C$_{12}$H$_{12}$FN$_5$O$_3$ (M+Na): 316.0822; found 316.0818.

The PPM and PNP enzymes used in this step were each derived from mutations starting from the enzymes from *E. coli* (*Escherichia coli*). The sucrose phosphorylase (SP) used in this step was derived from *Alloscardovia omnicolens*; SP derived from other organisms could also be used.

Method F2

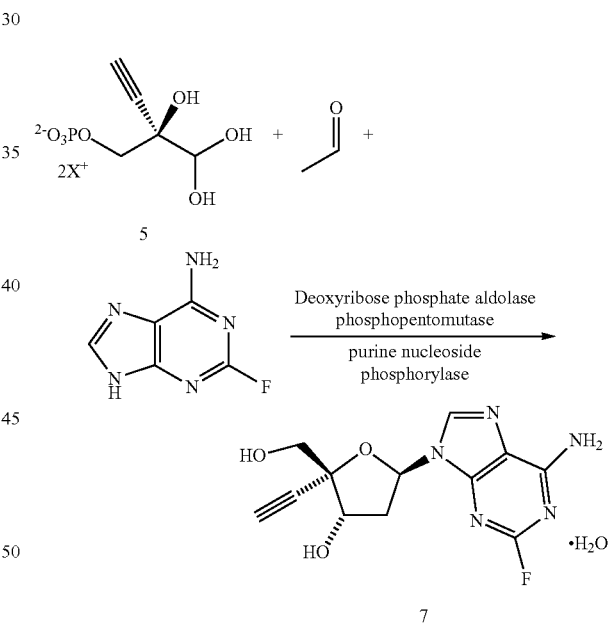

To an aqueous solution of (R)-2-ethynyl-glyceraldehyde 3-phosphate (5) (950 mL, 157 mmol) containing piperazine-N,N'-bis(2-ethanesulfonic acid) (PIPES) buffer at a pH from about 5.5 to 6.0 was added triethanolamine (7.09 g, 47.5 mmol). The pH of the solution was adjusted from 7.1 to 7.6 using potassium hydroxide (8 mL, 8M). Manganese(II) chloride hydrate (0.592 g, 4.70 mmol) was added followed by sucrose (161 g, 470 mmol), giving a pH of 7.5 To the solution was added the following enzymes: deoxyribose-phosphate aldolase (SEQ ID NO.: 14) (461 mg), sucrose phosphorylase (SEQ ID NO.: 7) (494 mg), phosphopentomutase (SEQ ID NO.: 8)(2.63 g), and purine nucleoside phosphorylase (SEQ ID NO.: 15) (659 mg). Once the enzymes were dissolved, 2-fluoroadenine (19.80 g, 125 mmol) was added. The reaction was heated to 35° C. and acetaldehyde was added (40 wt % in isopropyl alcohol, 29.8 mL, 235 mmol). After reacting for 2h, the mixture was seeded with EFdA crystalline product (0.96 g, 2 mol %). After reacting over 26 h at 35° C., the slurry was cooled to 0° C., and the solids were collected by filtration, washing with water two times (40 mL ea.). The solids were dried under a nitrogen sweep. Yield 43.2 g, 92 wt %, 96.2% corrected. $^1$H NMR: (300 MHz, DMSO-d6, ppm): δ 7.68 (br s, 2H), 7.32 (d, J=2.0 Hz, 1H), 6.44 (t, J=5.8 Hz, 1H), 5.52 (d, J=5.6 Hz, 1H), 5.27 (t, J=6.0 Hz, 1H), 4.44 (q, J=6.4 Hz, 1H), 3.60 (q, J=6.0 Hz, 1H), 3.53 (q, J=6.4 Hz, 1H), 3.48 (s, 1H), 2.48-2.41 (m, 1H), 2.37-2.30 (m, 1H). $^{13}$C NMR (150.92 MHz, DMSO-d6, ppm) δ 158.5 (d, JCF=203.5), 157.6 (d, JCF=21.2), 150.2 (d, JCF=20.2), 139.7 (d, JCF=2.4), 117.4 (d, JCF=4.0), 85.1, 82.0, 81.4, 78.7, 70.1, 64.2, 38.1. LC-MS: (ES, m/z): calculated for $C_{12}H_{12}FN_5O_3$ (M+Na): 316.0822; found 316.0818.

Alternate Preparations of
(S)-2-ethynyl-propane-1,2,3-triol 1 1-phosphate (9)

Method G1: Acetate Kinase: ATP-Regeneration System Using Enzymes SEQ. ID No.: 2 and SEQ. ID No.: 3

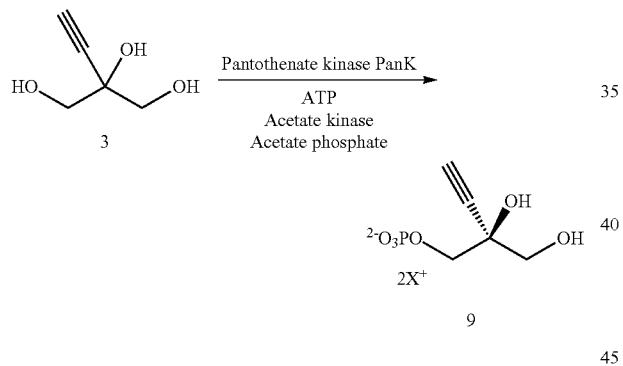

A 50 mL reactor was charged with a solution of 2-ethynyl-propane-1,2,3-triol (3) in water (9.29 g, 9.46 wt %, 7.57 mmol) potassium PIPES buffer (1.02 mL, 1 M, pH 6.5, 1.02 mmol), magnesium chloride (292 μL, 1 M, 0.292 mmol), acetyl phosphate diammonium salt (1.851 g, 89 wt %, 9.46 mmol), adenosine diphosphate disodium salt hydrate (ADP, 42 mg, 0.076 mmol, 0.01 eq), and water (28 mL). The pH was adjusted to 6.4 using 5 M KOH, the solution was warmed to 20° C. and evolved pantothenate kinase PanK SEQ. ID No.: 2 (264 mg) and acetate kinase AcK SEQ. ID No.: 3 (88 mg) were added. The reaction was stirred for 16 hours with pH maintained at 6.4 using 5 N KOH. The final reaction contents provided (S)-2-ethynyl-propane-1,2,3-triol 1-phosphate (9) in >95% e.e. and 99% conversion (by $^{31}$P NMR). The product was not isolated. $^1$H NMR (D$_2$O, 500 MHz) δ 3.89 (m, 2H), 3.72 (d, J=11.6 Hz, 1H), 3.65 (d, J=11.6 Hz, 1H), 2.93 (s, 1H). $^{13}$C NMR (D$_2$O, 126 MHz) δ 82.9 (s), 75.1 (s), 71.0 (d, J=6.9 Hz), 67.0 (d, J=4.5 Hz), 64.7 (s). 31P NMR (D$_2$O, 202 MHz) δ 3.39. HRMS: (ESI, m/z): calculated for [M−1]$^-$ $C_5H_8O_6P$: 195.0058; Found 195.0068 [M−H]$^-$: 195.0058.

Method G2: Acetate Kinase: ATP-Regeneration System Using Enzyme SEQ. ID No.: 20 and Enzyme SEQ. ID No.: 21

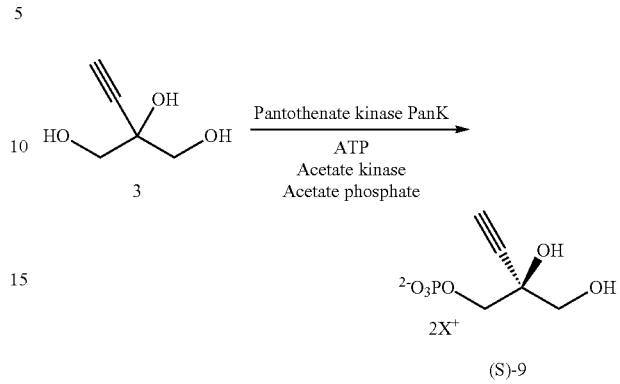

To a jacketed reactor aqueous solution 2-ethynyl-propane-1,2,3-triol (3) (11.47 kg, 8.7% wt, 8.61 mol) and water (7.5 kg) was charged, followed by 1M BIS-TRIS methane buffer pH 6.5 (1 L) and magnesium chloride (41.4 g). ATP (48g, 0.086 mol, 0.01 equivalent) and diammonium acetyl phosphate (2.021 kg, 89%, 10.33 mmol) were added, the solution was warmed up to 20° C. and the pH of the solution was re-adjusted to 6.8 using KOH (270.4 g). Evolved pantothenate kinase SEQ. ID No.: 20 (20.4 g) and evolved acetate kinase SEQ. ID No.: 21 (3 g) were then charged as solids. The reaction was stirred for at 20° C. for 16 h during which pH dropped to 5.5. Quantitative conversion of 2-ethynyl-propane-1,2,3-triol (3) was obtained as judged by $^1$H and 31P NMR. Such prepared (S)-2-ethynyl-propane-1,2,3-triol 1-phosphate (9) solution (397 mM, 22.5 kg, 98% yield) was used in subsequent oxidation step without any further purification. $^1$H NMR (D$_2$O, 500 MHz) δ 3.89 (m, 2H), 3.72 (d, J=11.6 Hz, 1H), 3.65 (d, J=11.6 Hz, 1H), 2.93 (s, 1H).

Method G3: Acetate Kinase: ATP-Regeneration System Using Enzyme SEQ. ID No.: 20 and Enzyme SEQ. ID No.: 21 With Deuterated Compound (3) to Assign Absolute Stereochemistry and Demonstrate Desymmetrizing Phosphorylation

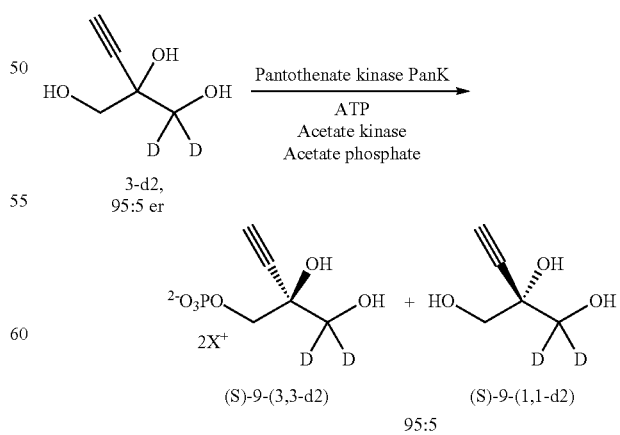

Evolved pantothenate kinase SEQ. ID No.: 20 (100 μL of 10 g/L solution in water) and evolved acetate kinase SEQ.

ID No.: 21 (100 μL of 2 g/L solution in water) were added to a solution containing diammonium acetyl phosphate (41 mg), 2-ethynyl-propane-1,1-d2-1,2,3-triol ((R)-3-d2, 20 mg, 170 μmol, magnesium chloride (10 μL of 1 M solution in water), ADP (10 μL of 100 g/L solution in water), and sodium phosphate buffer (10 μL of 1 M solution in water) in water (8004) at pH 6.5. The reaction was incubated for 24h at rt to give deuterated 2-ethynyl-propane-1,2,3-triol 1-phosphate analogs (S)-9-(3,3-d2) and (S)-9-(1,1-d2) in 95:5 ratio and 99% overall yield. The ratio of phosphorylated compounds was determined by $^{31}$P NMR to be ~95:5, confirming stereoselective phosphorylation of the 2-ethynyl-propane-1,2,3-triol (3) at the pro-(S) hydroxyl group (i.e. a desymmetrizing phosphorylation). $^{1}$H NMR (D$_2$O, 500 MHz) δ 3.89 (m, 2H), 3.72 (d, J=11.6 Hz, 1H), 3.65 (d, J=11.6 Hz, 1H), 2.93 (s, 1H). $^{13}$C NMR (D$_2$O, 126 MHz) δ 82.9 (s), 75.1 (s), 71.0 (d, J=6.9 Hz), 67.0 (d, J=4.5 Hz), 64.7 (s).

Method G4: Acetate Kinase: ATP-SEQ. ID No.: 20 and Enzyme SEQ. ID No.: 21

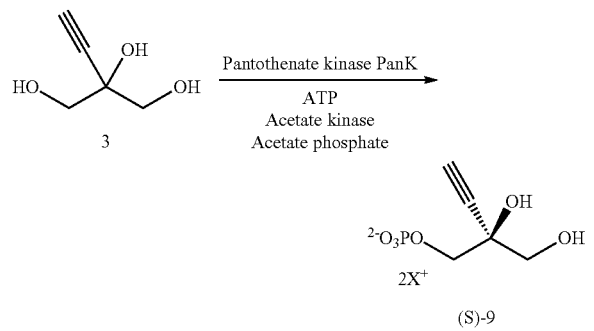

Enzyme Immobilization Procedure

Nuvia IMAC Ni-charged resin (75 mL based on settled volume) was added to a filter funnel and washed with water (9 column volumes, 3×225 mL) and binding buffer (1 column volume, 75 mL; 500 mM sodium chloride, 50 mM sodium phosphate, 15 mM imidazole, pH 8.0). In a vessel pantothenate kinase (SEQ ID NO.: 20, 6.0 g) lyophilized powder was resuspended in binding buffer (200 mL) and the washed resin was added. The solution was mixed using rotating mixer at 25° C. for 6h. The resin was filtered and washed with binding buffer (6 column volumes, 6×225 mL) and BIS-TRIS buffer (8 column volumes, 600 mL; 50 mM, pH 6.2).

Reaction Procedure

An aqueous solution of 2-ethynyl-propane-1,2,3-triol (3) (574 g, 8.7% wt, 0.430 mol) and water (350 mL) was charged to a jacketed reactor, followed by 1M BIS-TRIS methane buffer pH 6.5 (50 mL) and magnesium chloride (2.033 g, 0.01 mol). ATP (2.37 g, 0.0043 mol, 0.01 equivalent) and diammonium acetyl phosphate (101 g, 89%, 0.530 mmol, 1.2 eq) were added, the solution was warmed up to 20° C. and the pH of the solution was re-adjusted to 6.8 using 5 M KOH.

Resin with immobilized pantothenate kinase SEQ. ID No.: 20 (25 mL) and evolved acetate kinase SEQ. ID No.: 21 (0.15 g) were then charged as solids. The reaction was stirred for at 20° C. for 16 h during which the pH dropped to 5.5. Quantitative conversion of 2-ethynyl-propane-1,2,3-triol (3) to (S)-2-ethynyl-propane-1,2,3-triol 1-phosphate (9) was obtained as judged by $^{1}$H and $^{31}$P NMR. $^{1}$H NMR (D$_2$O, 500 MHz) δ 3.89 (m, 2H), 3.72 (d, J=11.6 Hz, 1H), 3.65 (d, J=11.6 Hz, 1H), 2.93 (s, 1H).

Alternate Preparations of (R)-2-ethynyl-glyceraldehyde 3-phosphate (5)

Method H1: Immobilized Galactose Oxidases SEQ ID No.: 16

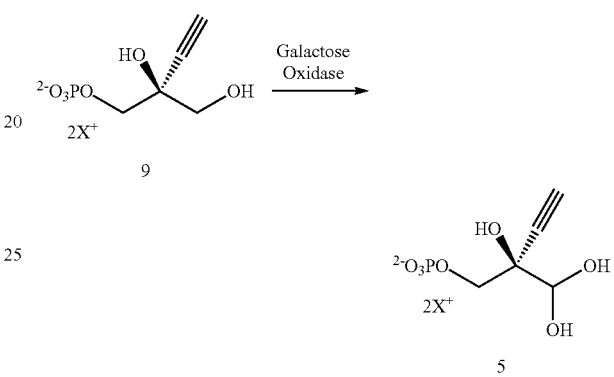

Enzyme Immobilization Procedure

Nuvia IMAC Ni-charged resin (10 mL based on settled volume) was added to a filter funnel and washed with binding buffer (10 column volumes, 100 mL; 500 mM sodium chloride, 50 mM sodium phosphate, 15 mM imidazole, pH 8.0) to remove the resin storage solution and give 16 g of washed resin. In a vessel evolved galactose oxidase (SEQ ID NO.: 16, 750 mg) lyophilized powders were resuspended in copper (II) sulphate solution (100 μM; 5.00 mL), followed by addition of binding buffer (20 mL) and the washed resin (3.0 g). The solution was mixed using rotating mixer at 20° C. for 5 h. The resin was filtered and washed with binding buffer (10 column volumes, 100 mL) and BIS-TRIS buffer (10 column volumes, 100 mL; 50 mM, pH 7.5) and it was used directly in the glycosylation reaction.

Reaction Procedure

The resin with immobilized galactose oxidase SEQ ID NO.: 16 (3.0 g) was added to a solution of (S)-2-ethynyl-propane-1,2,3-triol 1-phosphate (9, 5.4 mmol, 270 mM, 20 mL) in BIS-TRIS methane buffer (35 mM, pH adjusted to 7.2), followed by addition of copper (II) sulphate solution in water (30 μL, 100 mM) and horseradish peroxidase (PEO-301, 18 mg) and bovine catalase (C1345, 120 mg) resuspended in water (600 μL). The reaction was sealed with gas permeable membrane and shaken vigorously at 22° C. for 4 days to reach final conversion of 77% and give (R)-2-ethynyl-glyceraldehyde 3-phosphate (5) in 95% e.e. The enzyme resin was filtered off and the solution of the(R)-2-ethynyl-glyceraldehyde 3-phosphate (5) was used directly in the glycosylation reaction. 1H NMR (D$_2$O, 400 MHz): δ 5.02 (s, 1H), 4.00 (dq, 2H), 2.88 (s, 1H). LC-MS: (ES, m/z): calculated for C$_5$H$_7$O$_6$P (M−H): 193.1; found 193.0.

Method H2: Immobilized Galactose Oxidases SEQ ID No.: 17

Method H3: Immobilized Galactose Oxidases SEQ ID No.: 18

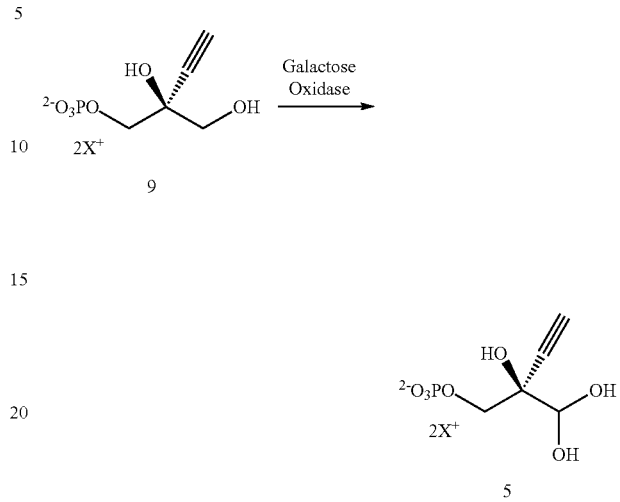

Enzyme Immobilization Procedure

Nuvia IMAC Ni-charged resin (10 mL based on settled volume) was added to a filter funnel and washed with binding buffer (10 column volumes, 100 mL; 500 mM sodium chloride, 50 mM sodium phosphate, 15 mM imidazole, pH 8.0) to remove the resin storage solution and give 16g of washed resin. In a vessel, evolved galactose oxidase (SEQ ID NO.: 16, 750 mg) lyophilized powders were resuspended in copper (II) sulphate solution (100 µM; 5.00 mL), followed by addition of binding buffer (20 mL) and the washed resin (3.0 g). The solution was mixed using rotating mixer at 20° C. for 5 h. The resin was filtered and washed with binding buffer (10 column volumes, 100 mL) and BIS-TRIS methane buffer (10 column volumes, 100 mL; 50 mM, pH 7.5) and it was used directly in the reaction.

Reaction Procedure

The resin with immobilized evolved galactose oxidase SEQ ID NO.: 17 (3.0 g) was added to a solution of (S)-2-ethynyl-propane-1,2,3-triol 1-phosphate (9, 5.4 mmol, 270 mM, 20 mL) in BIS-TRIS methane buffer (35 mM, pH adjusted to 7.2), followed by addition of copper (II) sulphate solution in water (30 µL, 100 mM) and horseradish peroxidase (PEO-301, 18 mg) and bovine catalase (C1345, 120 mg) resuspended in water (600 µL). The reaction was sealed with gas permeable membrane and shaken vigorously at 22° C. for 4 days to reach final conversion of 77% and give (R)-2-ethynyl-glyceraldehyde 3-phosphate (5) in 95% e.e. The enzyme resin was filtered off and the solution of the (R)-2-ethynyl-glyceraldehyde 3-phosphate (5) was used directly in the glycosylation reaction. $^1$H NMR (D$_2$O, 400 MHz): δ 5.02 (s, 1H), 4.00 (dq, 2H), 2.88 (s, 1H). LC-MS: (ES, m/z): calculated for C$_5$H$_7$O$_6$P (M−H): 193.1; found 193.0.

Enzyme Immobilization Procedure

Nuvia IMAC Ni-charged resin (3 mL based on settled volume) was added to a filter funnel and washed with binding buffer (10 column volumes, 30 mL; 500 mM sodium chloride, 50 mM sodium phosphate, 15 mM imidazole, pH 8.0) to remove the resin storage solution and give 2.4 g of washed resin. In a vial evolved galactose oxidase (SEQ ID NO.: 18, 75 mg) lyophilized powders were resuspended in copper (II) sulphate solution (100 µM; 1.00 mL), followed by addition of binding buffer (5 mL) and the washed resin (400 mg). The solution was mixed using rotating mixer at 20° C. for 5 h. The resin was filtered and washed with binding buffer (10 column volumes, 4 mL) and BIS-TRIS methane buffer (10 column volumes, 4 mL; 50 mM, pH 7.5) and it was used directly in a reaction.

Reaction Procedure

Immobilized evolved GOase SEQ ID NO.: 18 was added (400 mg) to a solution of (S)-2-ethynyl-propane-1,2,3-triol 1-phosphate solution ((9), 5.4 mmol, 270 mM, 1 mL) in BIS-TRIS methane buffer (35 mM, pH adjusted to 7.2), followed by addition of horseradish peroxidase (PEO-301, 1 mg) and catalase from *Corynebacterium glutamicum* (Roche, lyophilizate, #11650645103, 3 mg) resuspended in water (100 µL). The reaction was sealed with gas permeable membrane and shaken vigorously at 30° C. for 48 h. Final conversion after 2 days reached 90% conversion and the (R)-2-ethynyl-glyceraldehyde 3-phosphate (5) >99% e.e. The enzyme resin was filtered off and the solution of the (R)-2-ethynyl-glyceraldehyde 3-phosphate (5) was used directly without further purification. $^1$H NMR (D$_2$O, 400 MHz): δ 5.02 (s, 1H), 4.00 (dq, 2H), 2.88 (s, 1H). LC-MS: (ES, m/z): calculated for C$_5$H$_7$O$_6$P (M−H): 193.1; found 193.0.

Method H4: Immobilized Galactose Oxidases SEQ ID No.: 19

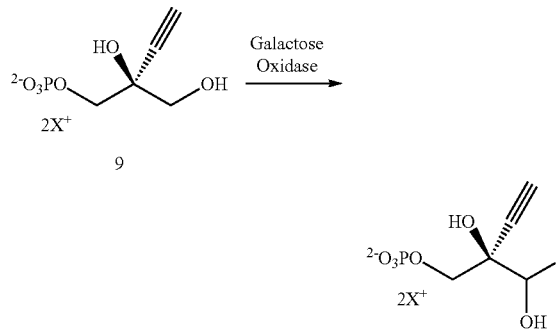

Enzyme Immobilization Procedure

Nuvia IMAC Ni-charged resin (3 mL based on settled volume) was added to a filter funnel and washed with binding buffer (10 column volumes, 30 mL; 500 mM sodium chloride, 50 mM sodium phosphate, 15 mM imidazole, pH 8.0) to remove the resin storage solution and give 2.4 g of washed resin. In a vial evolved galactose oxidase (SEQ ID NO.: 19, 75 mg) lyophilized powders were resuspended in copper (II) sulphate solution (100 µM; 1.00 mL), followed by addition of binding buffer (5 mL) and the washed resin (400 mg). The solution was mixed using rotating mixer at 20° C. for 5 h. The resin was filtered and washed with binding buffer (10 column volumes, 4 mL) and BIS-TRIS methane buffer (10 column volumes, 4 mL; 50 mM, pH 7.5) and it was used directly in a reaction.

Reaction Procedure

Immobilized evolved GOase SEQ ID NO.: 18 was added (400 mg) to a solution of (S)-2-ethynyl-propane-1,2,3-triol 1-phosphate solution (9, 5.4 mmol, 270 mM, 1 mL) in BIS-TRIS methane buffer (35 mM, pH adjusted to 7.2), followed by addition of horseradish peroxidase (PEO-301, 1 mg) and catalase from *Corynebacterium glutamicum* (Roche, lyophilizate, #11650645103, 3 mg) resuspended in water (100 µL). The reaction was sealed with gas permeable membrane and shaken vigorously at 30° C. for 48 h. Final conversion after 2 days reached 100% conversion and (R)-2-ethynyl-glyceraldehyde 3-phosphate (5) was obtained in >99% e.e. The enzyme resin was filtered off and the solution of the (R)-2-ethynyl-glyceraldehyde 3-phosphate (5) was used directly without further purification. $^1$H NMR ($D_2O$, 400 MHz): δ 5.02 (s, 1H), 4.00 (dq, 2H), 2.88 (s, 1H). LC-MS: (ES, m/z): calculated for $C_5H_7O_6P$ (M−H): 193.1; found 193.0.

"Amino acids" are referred to herein by either their commonly known by the one-letter symbols recommended by IUPAC-IUB Biochemical Nomenclature Commission. For the purposes of the description herein, the codes used for the genetically encoded amino acids for the enzymes used in the methods herein are conventional in Table 2:

TABLE 2

| Amino acid | One letter code |
| --- | --- |
| alanine | A |
| arginine | R |
| asparagine | N |
| aspartic acid | D |
| asparagine or aspartic acid | B |
| cysteine | C |
| glutamic acid | E |
| glutamine | Q |
| glutamine or glutamic acid | Z |
| glycine | G |
| histidine | H |
| isoleucine | I |
| leucine | L |
| lysine | K |
| methionine | M |
| phenylalanine | F |
| proline | P |
| serine | S |
| threonine | T |
| tryptophan | W |
| tyrosine | Y |
| valine | V |

Sequence ID numbers for the enzymes employed, or that could be employed, in the process for synthesizing EFdA described herein and in the exemplified process steps in the Experimental Procedures described herein are provided, but not limited to, those in Table 3.

TABLE 3

| SEQ ID NO: | ENZYME AND AMINO ACID SEQUENCE |
| --- | --- |
| 1 | Galactose Oxidase (GOase) = Variant of Galactose Oxidase from *Fusarium graminearum* (formerly known as *Dactylium dendroides*)<br>MASAPIGSAIPRNNWAVTCDSAQSGNECNKAIDGNKDTFWHTFYGANGDPKPP<br>HTYTIDMKTTQNVNGLSVLPRQDGNQNGWIGRHEVYLSSDGTNWGSPVASGS<br>WFADSTTKYSNFETRPARYVRLVAITEANGQPWTSIAEINVFQASSYTAPQPGL<br>GRWGPTIDLPIVPAAAAIEPTSGRVLMWSSYRNDAFEGSPGGITLTSSWDPSTGI<br>VSDRTSTVTKHDMFCPGISMDGNGQIVVDETATGGNDAKKTSLYDSSSDSWIP<br>GPDMQVARGYQSSATMSDGRVFTIGGSFSGGRVEKNGEVYSPSSKTWTSLPNA<br>KVNPMLTADKQGLYRSDNHAWLFGWKKGSVFQAGPSTAMNWYYTSGSGDV<br>KSAGKRQSNRGVAPDAMCGNAVMYDAVKGKILTFGGSPDYEDSDATTNAHIIT<br>LGEPGTSPNTVFASNGLYFARTFHTSVVLPDGSTFITGGQRRGIPTEDSTPVFTPE<br>IYVPEQDTFYKQNPNSIVRAYHSISLLLPDGRVFNGGGGLCGDCTTNHFDAQIFT<br>PNYLYDSNGNLATRPKITRTSTQSVKVGGRITISTDSSISKASLIRYGTATHTVNT<br>DQRRIPLTLTNNGGNSYSFQVPSDSGVALPGYWMLFVMNSAGVPSVASTIRVT<br>QGGGGSWSHPQFEK |
| 2 | Pantothenate Kinase (PanK) = Variant of Pantothenate Kinase from *E. coli*<br>MSIKEQTLMTPYLQFDRNQWAALRDSVPMTLSEDEIARLKGINEDLSLEEVAEI<br>YLPLSRLLNFYISSNLRRQAVLEQFLGTNGQRIPYIISIAGSVAVGKSTTARVLQA |

TABLE 3-continued

| SEQ ID NO: | ENZYME AND AMINO ACID SEQUENCE |
|---|---|
| | LLSRWPEHRRVELITTDGFLHPNQVLKERGLMKKKGFPESYDMHRLVKFVSDL<br>KSGVPNVTAPVYSHLIYDVIPDGDKTVVQPDILILEGLNVLQSGMDYPHDPHHV<br>FVSDFVDFSIYVDAPEDLLQTWYINRFLKFREGAFTDPDSYFHNYAKLTKEEAIK<br>TAMTIWKEMNWLNLKQNILPTRERASLILTKSANHAVEEVRLRK |
| 3 | Acetate Kinase (AcK) = wild type Acetate Kinase from *Thermotoga maritima*<br>MGSHHHHHHGSRVLVINSGSSSIKYQLIEMEGEKVLCKGIAERIGIEGSRLVHRV<br>GDEKHVIERELPDHEEALKLILNTLVDEKLGVIKDLKEIDAVGHRVVHGGERFK<br>ESVLVDEEVLKAIEEVSPLAPLHNPANLMGIKAAMKLLPGVPNVAVFDTAFHQ<br>TIPQKAYLYAIPYEYYEKYKIRRYGFHGTSHRYVSKRAAEILGKKLEELKIITCHI<br>GNGASVAAVKYGKCVDTSMGFTPLEGLVMGTRSGDLDPAIPFFIMEKEGISPQE<br>MYDILNKKSGVYGLSKGFSSDMRDIEEAALKGDEWCKLVLEIYDYRIAKYIGA<br>YAAAMNGVDAIVFTAGVGENSPITREDVCSYLEFLGVKLDKQKNEETIRGKEGI<br>ISTPDSRVKVLVVPTNEELMIARDTKEIVEKIGR |
| 4 | Pyruvate Oxidase (PO) = wild type Pyruvate oxidase from *Streptococcus thermophilus*<br>MGSSHHHHHHSSGLVPRGSHMTVGKTKVSTASLKVLAGWGIDTIYGIPSGTLA<br>PLMEALGEQEETDIKFLQVKHEEVGAMAAVMQWKFGGKLGVCVGSGGPGAS<br>HLINGLYDAAMDNTPVLAILGSPPQRELNMDAFQELNQNPMYDHIAVYNRRVA<br>YAEQLPKLIDDAIRTAISKRGVAVLEVPGDFGYKEIANDAFYSSGHSYRDYVSS<br>AINEVDIDAAVEVLNKSKRAVIYAGIGTMGHGPAVQELSRKIKAPIITTAKNFET<br>FDYDFEGLTGSTYRVGWKPANEAVKEADTVLFVGSNFPFAEVEGTFSNVENFIQ<br>IDNNPTMLGKRHNADVAILGDAGEAVQMLLEKVAPVEESAWWNANLKNIQN<br>WRDYMTKLETKENGPLQLYQVYNAINKYADEDAIYSIDVGNTTQTSIRHLHMT<br>PKNMWRTSPLFASMGIALPGGIGAKNVYPERQVFNLMGDGAFSMNYQDIVTN<br>VRYNMPVINVVFTNTEYGFIKNKYEDTNTNTFGTEFTDVDYAMIGEAQGAVGF<br>TVSRIEDMDQVMAAAVKANKEGKTVVIDAKITKDRPIPVETLKLDPALYSEEEI<br>KAYKERYEAEELVPFSEFLKAEGLESKVAK |
| 5 | Deoxyribose-phosphate Aldolase (DERA) = wild type Deoxyribose-phosphate<br>Aldolase from *Shewanella halifaxensis*<br>MSDLKKAAQQAISLMDLTTLNDDDTDQKVIELCHKAKTPAGDTAAICIYPRFIPI<br>ARKTLNEIGGDDIKIATVTNFPHGNDDIAIAVLETRAAVAYGADEVDVVFPYRA<br>LMEGNETVGFELVKACKEACGEDTILKVIIESGVLADPALIRKASELSIDAGADFI<br>KTSTGKVAVNATLEAAEIMMTVISEKNPKVGFKPAGGVKDAAAAAEFLGVAA<br>RLLGDDWATPATFRFGASSLLTNLLHTLELADAPQGAQGY |
| 6 | Deoxyribose-phosphate Aldolase (DERA) = Variant of Deoxyribose-phosphate<br>Aldolase (DERA) from *Shewanella halifaxensis*<br>MCDLKKAAQRAISLMDLTTLNDDDTDQKVIELCHKAKTPAGDTAAIVIYPRFIPI<br>ARKTLNEIGGLDIKIVTVTNFPHGNDDIAIAVLETRAAVAYGADEVDVVFPYRA<br>LMEGNETVGFELVKACKEACGEDTILKVIIESGVLKDPALIRKASEISIDAGADFI<br>KTSTGKVAVNATLEAAEIIMTVISEKNPKVGFKPAGGIKDAAAAAEFLGVAARL<br>LGDDWATPATFRFGATDLLTNLLHTLELADAPQGAQGY |
| 7 | Sucrose phosphorylase (SP) = wild type Sucrose phosphorylase from *Alloscardovia omnicolens*<br>MKNKVQLITYADRLGDGTLKSMTETLRKHFEGVYEGVHILPFFTPFDGADAGF<br>DPVDHTKVDPRLGSWDDVAELSTTHDIMVDTIVNHMSWESEQFQDVMAKGED<br>SEYYPMFLTMSSIFPDGVTEEDLTAIYRPRPGLPFTHYNWGGKTRLVWTTFTPQ<br>QVDIDTDSEMGWNYLLSILDQLSQSHVSQIRLDAVGYGAKEKNSSCFMTPKTF<br>KLIERIKAEGEKRGLETLIEVHSYYKKQVEIASKVDRVYDFAIPGLLLHALEFGK<br>TDALAQWIDVRPNNAVNVLDTHDGIGVIDIGSDQMDRSLAGLVPDEEVDALVE<br>SIHRNSKGESQEATGAAASNLDLYQVNCTYYAALGSDDQKYIAARAVQFFMPG<br>VPQVYYVGALAGSNDMDLLKRTNVGRDINRHYYSAAEVASEVERPVVQALNA<br>LGRFRNTLSAFDGEFSYSNADGVLTMTWADDATRATLTFAPKANSNGASVARL<br>EWTDAAGEHATDDLIANPPVVA |
| 8 | Phosphopentomutase (PPM) = Variant of Phosphopentomutase from *E. coli*<br>MKRAFIMVLDSFGIGATEDAERFGDVGADTLGHIAEACAKGEADNGRKGPLNL<br>PNLTRLGLAKAHEGSTGFIPAGMDGNAEVIGAYAWAHEMSSGKDSVSGHWEI<br>AGVPVLFEWGYFSDHENSFPQELLDKLVERANLPGYLGNCRSSGTVILDQLGEE<br>HMKTGKPIFYTSAASVFQIACHEETFGLDKLYELCEIAREELTNGGYNIGRVIAR<br>PFIGDKAGNFQRTGNRRDLAVEPPAPTVLQKLVDEKHGQVVSVGKIADIYANC<br>GITKKVKATGLDALFDATIKEMKEAGDNTIVFTNFVDFDSSWGHRRDVAGYAA<br>GLELFDRRLPELMSLLRDDDILILTADHGCDPTWTGTDHTREHIPVLVYGPKVK<br>PGSLGHRETFADIGQTLAKYFGTSDMEYGKAMF |
| 9 | Purine Nucleoside Phosphorylase (PNP) = Variant of Purine Nucleoside Phosphorylase<br>from *E. coli*<br>MATPHINAEMGDFADVVLMPGDPLRAKYIAETFLEDAREVNNVRGMLGFTGT<br>YKGRKISVMGHGAGIPSCSIYTKELITDFGVKKIIRVGSCGAVLPHVKLRDVVIG<br>MGACTDSKVNRIRFKDHDFAAIADFDMVRNAVDAAKALGIDARVGNLFSADL<br>FYSPDGEMFDVMEKYGILGVEMEAAGIYGVAAEFGAKALTICTVSDHIRTHEQ<br>TTAAERQTTFNDMIKIALESVLLGDKE |

TABLE 3-continued

| SEQ ID NO: | ENZYME AND AMINO ACID SEQUENCE |
|---|---|
| 10 | Galactose Oxidase (GOase) = Variant of Galactose Oxidase from *Fusarium graminearum* (formerly known as *Dactylium dendroides*)<br>MASAPIGVAIPRNNWAVTCDSAQSGNECNKAIDGNKDTFWHTQYGVNGDPKP<br>PHTITIDMKTVQNVNGLSVLPRQDGNQNGWIGRHEVYLSSDGVNWGSPVASGS<br>WFADSTTKYSNFETRPARYVRLVAITEANGQPWTSIAEINVFQASSYTAPQPGL<br>GRWGPTIDLPIVPSAAAIEPTSGRVLMWSSYRQDAFEGSPGGITLTSSWDPSTGI<br>VSDRTSTVTKHDMFCPGISMDGNGQIVVSGGNDAKKTSLYDSSSDSWIPGPDM<br>QVARGYQSSATMSDGRVFTIGGSFSGGQVEKNGEVYSPSSKTWTSLPNAKVNP<br>MLTADKQGLYRSDNHAWLFGWKKGSVFQAGPSTAMNWYYTSGSGDVKSAG<br>KRQSNRGVAPDAMCGNAVMYDAVKGKILTFGGSPDYEDSDATTLNHIITLGEP<br>GTSPNTVFASNGLYFARTFHTSVVLPDGSTFITGGQQRGIPTEDSTPVFTPEIYVP<br>EQDTFYKQNPNSIVRAYHSISLLLPDGRVFNGGGGLCGDCTTNHFDAQIFTPNY<br>LYDSNGNLATRPKITRTSTQSVVVGGWITIWTDMSISAASLIRYGTATHTVNTD<br>QRRIPLTLTNNGGNSYSFQVPSDSGVALPGYWMLFVMNSAGVPSVASTIRVTQ<br>GQTGHHHHHH |
| 11 | Galactose Oxidase (GOase) = Variant of Galactose Oxidase from *Fusarium graminearum* (formerly known as *Dactylium dendroides*)<br>MASAPIGVAIPRNNWAVTCDSAQSGNECNKAIDGNKDTFWHTQYGVNGDPKP<br>PHTITIDMKTVQNVNGLSVLPRQDGNQNGWIGRHEVYLSSDGVNWGSPVASGS<br>WFADSTTKYSNFETRPARYVRLVAITEANGQPWTSIAEINVFQASSYTAPQPGL<br>GRWGPTIDLPIVPSAAAIEPTSGRVLMWSSYRQDAFEGSPGGITLTSSWDPSTGI<br>VSDRTSTVTGHDMFCPGISMDGNGQIVVSGGNDAKKTSLYDSSSDSWIPGPDM<br>QVARGYNSSATMSDGRVFTIGGSFSGGQVEKNGEVYSPSSKTWTSLPNAKVNP<br>MLTADKQGLYRSDNHAWLFGWKKGSVFQAGPSTAMNWYYTSGSGDVKSAG<br>KRQSNRGVAPDAMCGNAVMYDAVKGKILTFGGSPDYQDSDATTNAHIITLGEP<br>GTSPNTVFASNGLLFARTFHTSVVLPDGSTFITGGQQRGIPTEDSTPVFTPEIYVP<br>EQDTFYKQNPNSIVRAYHSISLLLPDGRVFNGGGGLCGDCETNHFDAQIFTPNY<br>LYDSNGNLATRPKITRTSTQSVVVGGWITIWTDMSISAASLIRYGTATHTVNTD<br>QRRIPLTLTNNGGNSYSFQVPSDSGVALPGYWMLFVMNSAGVPSVASTINVTQ<br>GQTGHHHHHH |
| 12 | Pantothenate Kinase (PanK) = Variant of Pantothenate Kinase from *E. coli*<br>MSIKEQTLMTPYLQLDRNQWAALRDSNPMTLSEDEIARLKGINEDLSLEEVAEV<br>YLPLSRLLNFYISSNLRRQAVLEQFLGTNGQRIPYIISIAGSVAVGKSTTARVLQA<br>LLSRWPEHRRVELITTDGFLHPNQVLKERGLMKKKGFPESYDMHRLMKFVKDL<br>KSGVPNVTAPVYSHLIYDVIPDGDKTVVQPDILILEGLNVLQSGMDYPHDPHHV<br>FVSDFVDFSIYVDAPEDLLQTWYINRFLKFREGAFTDPDSYFHGYAKLTKEEAIK<br>TAMTIWKEMNHLNLKQNILPTRERASLILTKSANHIVEEVRLRK |
| 13 | Pantothenate Kinase (PanK) = Variant of Pantothenate Kinase from *E. coli*<br>MHHHHHHGGMSIKEQTLMTPYLQLDRNQWAALRDSNPMTLSEDEIARLKGIN<br>EDLSLEEVAEVYLPLSRLLNFYISSNLRRQAVLEQFLGTNGQRIPYIISIAGSVAV<br>GKSTTARVLQALLSRWPEHRRVEHITTDGFLHPNQVLKERGLMGKKGFPESYD<br>MHRLMKFVKDLKSGVPNVTAPVYSHLIYDVIPDGDKTVVQPDILILEGLNVLQS<br>GMDYPHDPHHVFVSDFVDFSIYVDAPEDLLQTWYINRFLKFREGAFTDPDSYFH<br>GYAKLTKEEAIKTAMTIWKEMNHLNLKQNILPTRERASLILTKSANHIVEEVRL<br>RK |
| 14 | Deoxyribose-phosphate Aldolase (DERA) = Variant of Deoxyribose-phosphate Aldolase (DERA) from *Shewanella halifaxensis*<br>MHHHHHHCDLKKAAQRAISLMDLTTLNDDDTDQKVIELCHKAKTPAGDTAAI<br>VIYPRFIPIARKTLNEIGGLDIKIVTVTNFPHGNDDIAIAVLETRAAVAYGADEVD<br>VVFPYRALMEGNETVGFELVKACKEACGEDTILKVIIESGVLKDPALIRKASEISI<br>DAGADFIKTSTGKVAVNATLEAAEHMTVISEKNPKVGFKPAGGIKDAAAAAEF<br>LGVAARLLGDDWATPATFRFGATDLLTNLLHTLELADAPQGAQGY |
| 15 | Purine Nucleoside Phosphorylase (PNP) = Variant of Purine Nucleoside Phosphorylase from *E. coli*<br>MATPHINAEMGDFADVVLMPGDPLRAKYIAETFLEDAREVNNVRGMLGFTGT<br>YKGRKISVMGHGMGIPSCSIYTKELITDFGVKKIIRVGSCGAVLPHVKLRDVVIG<br>MGACTDSKVNRIRFKDHDFAAIADFDMVRNAVDAAKALGIDARVGNLFSADL<br>FYSPDGEMFDVMEKYGILGVEMEAAGIYGVAAEFGAKALTICTVSDHIRTHEQ<br>TTAAERQTTFNDMIKIALESVLLGDKE |
| 16 | Galactose Oxidase (GOase) = Variant of Galactose Oxidase from *Fusarium graminearum* (formerly known as *Dactyhum dendroides*)<br>MASAPIGVAIPRNNWAVTCDSAQSGNECNKAIDGNKDTFWHTQYGVNGDPKP<br>PHTITIDMKTVQNVNGLSVLPRQDGNQNGWIGRHEVYLSSDGVNWGSPVASGS<br>WFADSTTKYSNFETRPARYVRLVAITEANGQPWTSIAEINVFQASSYTAPQPGL<br>GRWGPTIDLPIVPSAAAIEPTSGRVLMWSSYRQDAFEPSPGGITLTSSWDPSTGIV<br>SDRTSTVTGHDMFCPGISMDGNGQIVVSGGNDAKKTSLYDSSSDSWIPGPDMQ<br>VARGYNSSATMSDGRVFTIGGSYSGGQVEKNGEVYSPSSKTWTSLPNAKVNPM<br>LTADKQGLYRSDNHAWLFGWKKGSVFQAGPSTAMNWYYTSGSGDVKSAGKR<br>QSDRGVAPDAMCGNAVMYDAVKGKILTFGGSPDYQDSDATTNAHIITLGEPGT<br>SPNTVFASNGLLFARTFHTSVVLPDGSVFITGGQQRGVPLEDSTPVFTPEIYVPEQ<br>DTFYKQNPNSIVRAYHSISLLLPDGRVFNGGGGLCGDCETNHFDAQIFTPNYLY |

TABLE 3-continued

| SEQ ID NO: | ENZYME AND AMINO ACID SEQUENCE |
|---|---|
| | DSNGNLATRPKITRTSTQSVVVGGWITIWTDMSISAASLIRYGTATHTVNTDQR<br>RIGLTLTNNGGNSYSFQVPSDSGVALPGYWMLFVMNSAGVPSVASTINVTQGQ<br>TGHHHHHH |
| 17 | Galactose Oxidase (GOase) = Variant of Galactose Oxidase from *Fusarium graminearum* (formerly known as *Dactylium dendroides*)<br>MASAPIGVAIPRNNWAVTCDSAQSGNECIKAIDGNKDTFWHTQYGVNGDPKPP<br>HTITIDMKTVQNVNGLSVLPRQDGNQNGWIGRHEVYLSSDGVNWGSPVASGS<br>WFADSTTKYSNFETRPARYVRLVAITEANGQPWTSIAEINVFQASSYTAPQPGL<br>GRWGPTIDLPIVPSAAAIEPTSGRVLMWSSYRQDAFEDSPGGITLTSSWDPSTGI<br>VSDRTSTVTGHDMFCPGISMDGNGQIVVSGGNDAKKTSLYDSSSDSWIPGPDM<br>QVARGYNSSATMSDGRVFTIGGSYSGGQVEKNGEVYSPSSKTWTSLPNAKVNP<br>MLTADKQGLYRSDNHAWLFGWKKGSVFQAGPSTAMNWYYTSGSGDVKSAG<br>KRQSDRGVAPDAMCGNAVMYDAVKGKILTFGGSPDYQDSDATTNAHIITLGEP<br>GTSPNTVFASNGLLFARTFHTSVVLPDGSVFITGGQQRGVPLEDSTPVFTPEIYVP<br>EQDTFYKQNPNSIVRAYHSISLLLPDGRVFNGGGGLCGDCETNHFDAQIFTPNY<br>LYDSNGNLATRPKITRTSTQSVVVGGWITIWTDMSISAASLIRYGTATHTVNTD<br>QRRIGLTLTNNGGNSYSFQVPSDSGVALPGYWMLFVMNSAGVPSVASTINVTQ<br>GQTGHHHHHH |
| 18 | Galactose Oxidase (GOase) = Variant of Galactose Oxidase from *Fusarium graminearum* (formerly known as *Dactylium dendroides*)<br>MASAPIGVAIPRNNWAVTCDSAQSGNECIKAIDGNKDTFWHTQYGVNGDPKPP<br>HTITIDMKTVQNVNGLSVLPRQDGNQNGWIGRHEVYLSSDGVNWGSPVASGS<br>WFADSTTKYSNFETRPARYVRLVAITEANGQPWTSIAEINVFQASSYTAPQPGL<br>GRWGPTIDLPIVPSAAAIEPTSGRVLMWSSYRQDAFEDSPGGITLTSSWDPSTGI<br>VSDRTSTVTGHDMFCPGISMDGNGQIVVSGGNDAKKTSLYDSSSDSWIPGPDM<br>QVARGYNSSATMSDGRVFTIGGSYSGGQVEKNGEVYSPSSKTWTSLPNAKVNP<br>MLTADKRGLYRSDNHAWLFGWKKGSVFQAGPSTAMNWYYTSGSGDVKSAG<br>KRQSDRGVAPDAMCGNAVMYDAVKGKILTFGGSPDYQDSDATTNAHIITLGEP<br>GTSPNTVFASNGLLFARTFHTSVVLPDGSVFITGGQQRGVPLEDSTPVFTPEIYVP<br>EQDTFYKQNPNSIVRAYHSISLLLPDGRVFNGGGGLCGDCETNHFDAQIFTPNY<br>LYDSNGNLATRPKITRTSTQSVVVGGWITIWTDMSISAASLIRYGTATHTVNTD<br>QRRIGLTLTNNGGNSYSFQVPSDSGVALPGYWMLFVMNSAGVPSVASTINVTQ<br>GQTGHHHHHH |
| 19 | Galactose Oxidase (GOase) = Variant of Galactose Oxidase from *Fusarium graminearum* (formerly known as *Dactylium dendroides*)<br>MASAPIGVAIPRNNWAVTCDSAQSGNECIKAIDGNKDTFWHTQYGVNGDPKPP<br>HTITIDMKTVQNVNGLSVLPRQDGNQNGWIGRHEVYLSSDGVNWGSPVASGS<br>WFADSTTKYSNFETRPARYVRLVAITEANGQPWTSIAEINVFQASSYTAPQPGL<br>GRWGPTIDLPIVPSAAAIEPTSGRVLMWSSYRQDAFRDSPGGITLTSSWDPSTGI<br>VSDRTSTVTGHDMFCPGISMDGNGQIVVSGGNDAKKTSLYDSSSDSWIPGPDM<br>QVARGYNSSATMSDGRVFTIGGSYSGGQVEKNGEVYSPSSKTWTSLPNAKVNP<br>MLTADKQGLYRSDNHAWLFGWKKGSVFQAGPSTAMNWYYTSGSGDVKSAG<br>KRQSDRGVAPDAMCGNAVMYDAVKGKILTFGGSPDYQDSDATTNAHIITLGEP<br>GTSPNTVFASNGLLFARTFHTSVVLPDGSVFITGGQQRGVPLEDSTPVFTPEIYVP<br>EQDTFYKQNPNSIVRAYHSISLLLPDGRVFNGGGGLCGDCETNHFDAQIFTPNY<br>LYDSNGNLATRPKITRTSTQSVVVGGWITIWTDMSISAASLIRYGTATHTVNTD<br>QRRIGLTLTNNGGNSYSFQVPSDSGVALPGYWMLFVMNSAGVPSVASTINVTQ<br>GQTGHHHHHH |
| 20 | Pantothenate Kinase (PanK) = Variant of Pantothenate Kinase from *E. coli*<br>MHHHHHHGGSGSIKEQTLMTPYLQLDRNQWAALRDSNPMTLSEDEIARLKGIN<br>EDLSLEEVAEVYLPLSRLLNFYISSNLRRQAQLEQFLGTNGQRIPYIISIAGSVAV<br>GKSTFARVLQALLSRWPEHRRVEHITTDGFLHPNQVLKERGLMGKKGFPESYD<br>MHRLMKFVKDLKSGVPNVTAPVYSHLIYDVIPDGDKTVVQPDILILEGLNVLQS<br>GMDYPHDPHHVFVSDFVDFSIYVDAPEDLLQTWYINRFLKFREGAFTDPDSYFH<br>GYAKLTKEEAIKTAMTIWKEMNHVNLKQNILPTRERASLILTKSANHIVEEVRL<br>RK |
| 21 | Acetate Kinase (AcK) = Variant of Acetate Kinase from *Thermotoga maritima*<br>MGSHHHHHHGSRVLNINSGSSSIKYQLIEMEGEKVLCKGIAERIGIEGSRLVHRV<br>GDEKHVIERELPDHEEALKLILNTLVDEKLGVIKDLKEIDAVGHRVVHGGERFK<br>ESVLVDEEVLKAIEEVSPLAPLHNPANLMGIKAAMKLLPGVPNVQVFDTAFHQ<br>TIPQKAYLYAIPYEYYEKYKIRRYGFHGISHRYVSKRAAEILGKKLEELKIITCHI<br>GNGASVAAVKYGKCVDTSMGFTPLEGLVMGTRSGDLDPAIPFFIMEKEGISPQE<br>MYDILNKKSGVYGLSKGFSSDMRDNLEAALKGDEWCKLVLEIYDYRIAKYIGA<br>YAAAMNGVDAIVFTAGVGENSPITREDVCKYLEFLGVKLDKQKNEETIRGKEGI<br>ISTPDSRVKVLVVPTNEELMIARDTKEIVEKIGR |

Horseradish Peroxidase: wild type peroxidase from horseradish Type I, commercially available from SIGMA (P8125), isolated from horseradish roots (*Amoracia rusticana*).

Catalase: (1) wild type Catalase from bovine liver, commercially available from SIGMA (C1345); or (2) CAT-101, Biocatalytics; or (3) from *Corynebacterium glutamicum* (Roche, #11650645103).

Additional embodiments of this invention include, but are not limited to, the use of the following enzymes in the synthetic process steps described herein for producing a 4'-ethynyl 2'-deoxy nucleoside or an analog thereof, for example, EFdA.

A. A purine nucleoside phosphorylase.
1A. An engineered purine nucleoside phosphorylase comprising a polypeptide sequence having at least 85%, 86%, 87%, 88%, 89%, 90%, 91%, 92%, 93%, 94%, 95%, 96%, 97%, 98%, 99% or more sequence identity to SEQ ID NO.: 9 or SEQ ID NO.: 15, or a functional fragment thereof, wherein the polypeptide sequence of said engineered purine nucleoside phosphorylase comprises at least one amino acid substitution or amino acid substitution set as compared to SEQ ID NO: 9 or SEQ ID NO.: 15.
2A. The engineered purine nucleoside phosphorylase of 1A, wherein said engineered purine nucleoside phosphorylase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 9 or SEQ ID NO.: 15.
3A. An engineered purine nucleoside phosphorylase which is comprised of the polypeptide sequence as set forth in SEQ ID NO: 9 or SEQ ID NO.: 15.
A4. The engineered purine nucleoside phosphorylase of any one of 1A to 3A, which comprises at least one improved property compared to wild-type *E. coli* purine nucleoside phosphorylase.
5A. The engineered purine nucleoside phosphorylase of 4A, wherein said improved property comprises improved activity on substrate compound 6.5 (in its ring form or as an open chain aldehyde or hydrate, or a salt of any of the foregoing) as compared to wild type *E. coli* purine nucleoside phosphorylase.
6A. The engineered purine nucleoside phosphorylase of 4A, wherein said improved property comprises improved production of EFdA (compound 7) as compared to wild type *E. coli* purine nucleoside phosphorylase.
7A. The engineered purine nucleoside phosphorylase of any of one of A1 to 6 A, wherein said engineered purine nucleoside phosphorylase is purified.
8A. The engineered purine nucleoside phosphorylase of any of one of 1A to 7A, wherein the at least one amino acid substitution (i.e., one or more amino acid substitution(s)) are conservative amino acid substitution(s).

B. A phosphopentomutase.
1B. An engineered phosphopentomutase comprising a polypeptide sequence having at least 85%, 86%, 87%, 88%, 89%, 90%, 91%, 92%, 93%, 94%, 95%, 96%, 97%, 98%, 99% or more sequence identity to SEQ ID NO.: 8, or a functional fragment thereof, wherein the polypeptide sequence of said engineered phosphopentomutase comprises at least one amino acid substitution or amino acid substitution set as compared to SEQ ID NO: 8.
2B. The engineered phosphopentomutase of 1B, wherein said engineered phosphopentomutase comprises a polypeptide sequence that is at least 85%, 86%, 87%, 88%, 89%, 90%, 91%, 92%, 93%, 94%, 95%, 96%, 97%, 98%, 99% or more identical to SEQ ID NO.: 8.
3B. An engineered phosphopentomutase which is comprised of the polypeptide sequence as set forth in SEQ ID NO.: 8.
4B. The engineered phosphopentomutase of any one of 1B to 3B, which comprises at least one improved property compared to wild-type *E. coli* phosphopentomutase.
5B. The engineered phosphopentomutase of 4B, wherein said improved property comprises improved activity on substrate compound 6 (in its ring form or as an open chain aldehyde or hydrate, or a salt of any of the foregoing) as compared to wild type *E. coli* phosphopentomutase.
6B. The engineered phosphopentomutase of 4B, wherein said improved property comprises improved production of compound 6.5 or compound 7 (EFdA) as compared to wild type *E. coli* phosphopentomutase.
7B. The engineered phosphopentomutase of any of one of 1B to 6B, wherein said engineered phosphopentomutase is purified.
8B. The engineered phosphopentomutase of any of one of 1B to 7B, wherein the at least one amino acid substitution (i.e., one or more amino acid substitution(s)) are conservative amino acid substitution(s).

C. A deoxyribose-phosphate aldolase.
1C. A deoxyribose-phosphate aldolase which is comprised of the wild type from *Shewanella halifaxensis* polypeptide sequence as set forth in SEQ ID NO.: 5.
2C. An engineered deoxyribose-phosphate aldolase which is comprised of the polypeptide sequence as set forth in SEQ ID NO.: 6 or SEQ ID NO.: 14.
3C. An engineered deoxyribose-phosphate aldolase, wherein said engineered deoxyribose-phosphate aldolase comprises a polypeptide sequence that is at least 85%, 86%, 87%, 88%, 89%, 90%, 91%, 92%, 93%, 94%, 95%, 96%, 97%, 98%, 99% or more identical to SEQ ID NO.: 5, SEQ ID NO.: 6 or SEQ ID NO.: 14.
4C. An engineered deoxyribose-phosphate aldolase comprising a polypeptide sequence having at least 85%, 86%, 87%, 88%, 89%, 90%, 91%, 92%, 93%, 94%, 95%, 96%, 97%, 98%, 99% or more sequence identity to SEQ ID NO.: 5, SEQ ID NO.: 6 or SEQ ID NO.: 14, or a functional fragment thereof, wherein the polypeptide sequence of said engineered deoxyribose-phosphate aldolase comprises at least one amino acid substitution or amino acid substitution set as compared to SEQ ID NO.: 5, SEQ ID NO.: 6 or SEQ ID NO.: 14.
5C. The deoxyribose-phosphate aldolase of any one of 1C to 4C, which has activity on substrate compound 5 ((R)-2-ethynyl-glyceraldehyde 3-phosphate, the hydrate thereof, or a salt of either of the foregoing).
6C. The deoxyribose-phosphate aldolase of any one of 1C to 5C, which comprises the ability to produce compound 6 (4-ethynyl-D-2-deoxyribose 5-phosphate, or the open chain aldehyde or hydrate form thereof, or a salt of any of the foregoing) without need for protecting groups on substrate compound 5 ((R)-2-ethynyl-glyceraldehyde 3-phosphate, the hydrate thereof, or a salt of either of the foregoing) during the reaction.
7C. The engineered deoxyribose-phosphate aldolase of any one of 2C to 6C, wherein the deoxyribose-phosphate aldolase has an improved property which comprises improved production of compound 6 (4-ethynyl-D-2-deoxyribose 5-phosphate, or the open chain aldehyde or hydrate form thereof, or a salt of any of the foregoing) as compared to wild-type *Shewanella halifaxensis* deoxyribose-phosphate aldolase.
8C. The deoxyribose-phosphate aldolase of any one of 1C to 7C, wherein said deoxyribose-phosphate aldolase is purified.

9C. The engineered deoxyribose-phosphate aldolase of any one of 2C to 7C, wherein the at least one amino acid substitution (i.e., one or more amino acid substitution(s)) are conservative amino acid substitution(s).

D. A pantothenate kinase.

1D. An engineered pantothenate kinase comprising a polypeptide sequence having at least 85%, 86%, 87%, 88%, 89%, 90%, 91%, 92%, 93%, 94%, 95%, 96%, 97%, 98%, 99% or more sequence identity to SEQ ID NO: 2, SEQ ID NO.: 12, SEQ ID NO.: 13 or SEQ ID NO.: 20, or a functional fragment thereof, wherein the polypeptide sequence of said engineered pantothenate kinase comprises at least one amino acid substitution or amino acid substitution set as compared to SEQ ID NO: 2, SEQ ID NO.: 12, SEQ ID NO.: 13 or SEQ ID NO.: 20.

2D. The engineered pantothenate kinase of 1D, wherein said engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO.: 2, SEQ ID NO.: 12, SEQ ID NO.: 13 or SEQ ID NO.: 20.

3D. An engineered pantothenate kinase, which is comprised of the polypeptide sequence as set forth in SEQ ID NO.: 2, SEQ ID NO.: 12, SEQ ID NO.: 13 or SEQ ID NO.: 20.

4D. The engineered pantothenate kinase of any one of 1D to 3D, which comprises at least one improved property compared to wild-type E. coli pantothenate kinase.

5D. The engineered pantothenate kinase of 4D, wherein said improved property comprises improved activity on substrate compound 4 ((R)-2-ethynyl-glyceraldehyde or hydrate form thereof) as compared to wild-type E. coli pantothenate kinase.

6D. The engineered pantothenate kinase of 5D, wherein said improved property comprises improved production of compound 5 ((R)-2-ethynyl-glyceraldehyde 3-phosphate), as compared to wild-type pantothenate kinase.

7D. The engineered pantothenate kinase of 4D, wherein said improved property comprises improved activity on substrate compound 3 (2-ethynyl-propane-1,2,3-triol) as compared to wild-type E. coli pantothenate kinase.

8D. The engineered pantothenate kinase of 7D, wherein said improved property comprises improved production of compound 9 ((S)-2-ethynyl-propane-1,2,3-triol 1-phosphate), as compared to wild-type pantothenate kinase.

9D. The engineered pantothenate kinase of any one of 1D to 8D, wherein said pantothenate kinase is purified.

10D. The engineered pantothenate kinase of any one of 1D to 9D, wherein the at least one amino acid substitution (i.e., one or more amino acid substitution(s)) are conservative amino acid substitution(s).

E. A galactose oxidase.

1E. An engineered galactose oxidase comprising a polypeptide sequence having at least 85%, 86%, 87%, 88%, 89%, 90%, 91%, 92%, 93%, 94%, 95%, 96%, 97%, 98%, 99% or more sequence identity to SEQ ID NOs.: 1, 10, 11, 16, 17, 18 or 19, or a functional fragment thereof, wherein the polypeptide sequence of said engineered galactose oxidase comprises at least one amino acid substitution or amino acid substitution set as compared to SEQ ID NOs.: 1, 10, 11, 16, 17, 18 or 19.

2E. The engineered galactose oxidase of 1E, wherein said engineered galactose oxidase comprises a polypeptide sequence that is at least 85%, 86%, 87%, 88%, 89%, 90%, 91%, 92%, 93%, 94%, 95%, 96%, 97%, 98%, 99% or more identical to SEQ ID NOs.: 1, 10, 11, 16, 17, 18 or 19.

3E. An engineered galactose oxidase which is comprised of the polypeptide sequence as set forth in SEQ ID NOs.: 1, 10, 11, 16, 17, 18 or 19.

4E. The engineered galactose oxidase of any one of 1E to 3E, which comprises at least one improved property compared to wild-type F. graminearum galactose oxidase.

5E. The engineered galactose oxidase of 4E, wherein said improved property comprises improved activity on a substrate which is a primary alcohol as compared to wild type F. graminearum galactose oxidase.

6E. The engineered galactose oxidase of 4E, wherein said improved property comprises improved activity on substrate compound 3 (2-ethynyl-propane-1,2,3-triol) as compared to wild type F. graminearum galactose oxidase.

7E. The engineered galactose oxidase of 6E, wherein said improved property comprises improved production of compound 4 ((R)-2-ethynyl-glyceraldehyde or hydrate form thereof) as compared to wild type F. graminearum galactose oxidase.

8E. The engineered galactose oxidase of 4E, wherein said improved property comprises improved activity on substrate compound 9 ((S)-2-ethynyl-propane-1,2,3-triol 1-phosphate), as compared to wild type F. graminearum galactose oxidase.

9E. The engineered galactose oxidase of 8E, wherein said improved property comprises improved production of compound 5 ((R)-2-ethynyl-glyceraldehyde 3-phosphate or hydrate form thereof), as compared to wild type F. graminearum galactose oxidase.

10E. The engineered galactose oxidase of any of one of 1E to 9E, wherein said galactose oxidase is purified.

11E. The engineered galactose oxidase of any of one of 1E to 10E, wherein the at least one amino acid substitution (i.e., one or more amino acid substitution(s)) are conservative amino acid substitution(s).

F. An acetate kinase.

1F. An acetate kinase, which is comprised of the wild type from Thermotoga maritima polypeptide sequence as set forth in SEQ ID NO.: 3 or SEQ ID NO.: 21.

2F. An engineered acetate kinase, wherein said engineered acetate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO.: 3 or SEQ ID NO.: 21.

3F. An engineered acetate kinase comprising a polypeptide sequence having at least 85%, 86%, 87%, 88%, 89%, 90%, 91%, 92%, 93%, 94%, 95%, 96%, 97%, 98%, 99% or more sequence identity to SEQ ID NO.: 3 or SEQ ID NO.: 21, or a functional fragment thereof, wherein the polypeptide sequence of said engineered acetate kinase comprises at least one amino acid substitution or amino acid substitution set as compared to SEQ ID NO.: 3 or SEQ ID NO: 21.

4F. The acetate kinase of 2F or 3F, which comprises at least one improved property compared to wild-type T. maritima acetate kinase.

5F. The acetate kinase of 4F, wherein said improved property comprises improved activity for ATP-cofactor recycling in the phosphorylation reaction on substrate compound 4 ((R)-2-ethynyl-glyceraldehyde or hydrate form thereof) as compared to wild-type Thermotoga maritima acetate kinase.

6F. The acetate kinase of 5F, wherein said improved property comprises improved production of compound 5 ((R)-2-ethynyl-glyceraldehyde 3-phosphate or a hydrate form thereof or a salt of either of the foregoing) as compared to wild-type *Thermotoga maritima* acetate kinase.

7F. The acetate kinase of 4F, wherein said improved property comprises improved activity for ATP-cofactor recycling in the phosphorylation reaction on substrate compound 3 (2-ethynyl-propane-1,2,3-triol) as compared to wild-type *Thermotoga maritima* acetate kinase.

8F. The acetate kinase of 7F, wherein said improved property comprises improved production of compound 9 ((S)-2-ethynyl-propane-1,2,3-triol 1-phosphate or a salt of either of the foregoing) as compared to wild-type *Thermotoga maritima* acetate kinase.

9F. The acetate kinase of any of one of 1F to 8F, wherein said acetate kinase is purified.

10F. The engineered acetate kinase of any of one of 2F to 7F, wherein at least one amino acid substitution (i.e., one or more amino acid substitution(s)) are conservative amino acid substitution(s).

---

What is claimed is:

1. A method for synthesizing a 4'-ethynyl 2'-deoxy nucleoside or an analog thereof comprising combining compound 6.5:

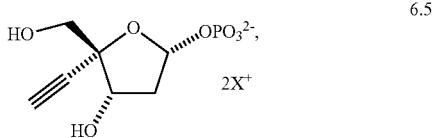

with purine nucleoside phosphorylase and a nucleobase or an analog thereof, in a buffered solution containing a manganese (II) salt,
and wherein 2X⁺ is (a) two protons, (b) one proton and one monovalent cation, (c) two monovalent cations wherein each cation is the same or different, or (d) one divalent cation.

2. The method of claim 1 wherein the 4'-ethynyl 2'-deoxy nucleoside is

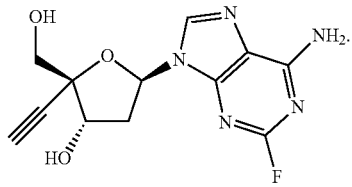 [SMILES: C#C[C@]1(CO)O[C@@H](n2cnc3c(N)nc(F)nc32)C[C@@H]1O]

3. The method of claim 2 further comprising isolating

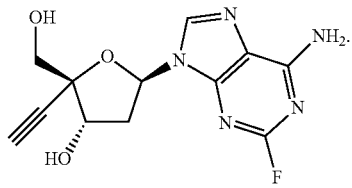 [SMILES: C#C[C@]1(CO)O[C@@H](n2cnc3c(N)nc(F)nc32)C[C@@H]1O]

4. The method of claim 1 for synthesizing a 4'-ethynyl 2'-deoxy nucleoside or an analog thereof further comprising combining compound 6

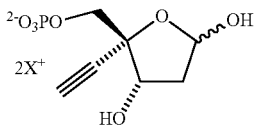

and phosphopentomutase with the purine nucleoside phosphorylase and the nucleobase or the analog thereof in the buffered solution containing a manganese (II) salt.

5. The method of claim 4 further comprising removing inorganic phosphate byproduct from the reaction mixture.

6. The method of claim 5 comprising removing inorganic phosphate byproduct from the reaction mixture by (a) adding sucrose phosphorylase and sucrose to the reaction mixture or (b) adding calcium, magnesium or manganese to the reaction mixture.

7. The method of claim 5 further comprising isolating the 4'-ethynyl 2'-deoxy nucleoside or the analog thereof.

8. The method of claim 5 wherein the 4'-ethynyl 2'-deoxy nucleoside is

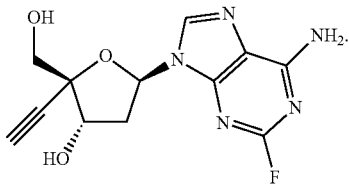 [SMILES: C#C[C@]1(CO)O[C@@H](n2cnc3c(N)nc(F)nc32)C[C@@H]1O]

9. The method of claim 8 further comprising isolating

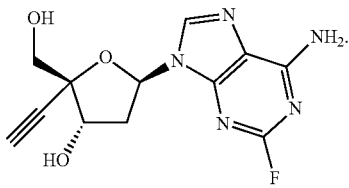 [SMILES: C#C[C@]1(CO)O[C@@H](n2cnc3c(N)nc(F)nc32)C[C@@H]1O]

10. The method of claim 4 further comprising the step of synthesizing compound 6, wherein the synthesis comprises combining compound 5

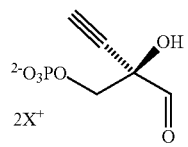

with acetaldehyde and deoxyribose-phosphate aldolase in an aqueous solution to produce compound 6;
wherein 2X⁺ is (a) two protons, (b) one proton and one monovalent cation, (c) two monovalent cations wherein each cation is the same or different, or (d) one divalent cation.

11. The method of claim 10 wherein the synthesis of compound 6 is performed in a sealed vessel.

12. The method of claim 10 further comprising the step of synthesizing compound 5, wherein the synthesis comprises (i) combining compound 4

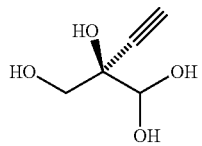
4 with pantothenate kinase in a buffered solution,
in the presence of a bi-valent metal salt,
with ATP as a phosphate source wherein the ATP is regenerated in situ, or
(ii) combining compound 9

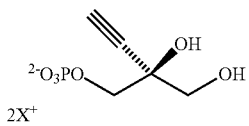
9 with galactose oxidase in a buffered solution,
in the presence of oxygen, catalase and either a peroxidase or a chemical oxidant,
wherein $2X^+$ is (a) two protons, (b) one proton and one monovalent cation, (c) two monovalent cations wherein each said cation is the same or different, or (d) one divalent cation.

13. The method of claim 12 wherein the ATP is regenerated in situ employing (a) acetyl phosphate and acetate kinase, or (b) pyruvate oxidase, catalase and acetate kinase in the presence of pyruvate, phosphate and oxygen or (c) a combination thereof.

14. The method of claim 13 wherein (a) the pantothenate kinase is immobilized or (b) the pantothenate kinase and the acetate kinase are immobilized.

15. The method of claim 12 further comprising the step of synthesizing compound 4, wherein the synthesis comprises combining compound 3

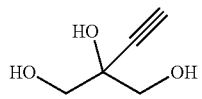
3 with (a) galactose oxidase, copper, catalase and (b) peroxidase or an oxidant;
in the presence of oxygen, in a buffered solution to produce compound 4.

16. The method of claim 15 wherein the galactose oxidase is immobilized.

17. The method of claim 12 further comprising the step of synthesizing compound 9

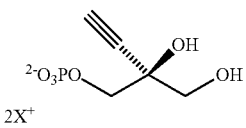
9 comprising combining compound 3

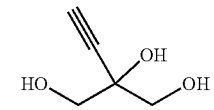
3 with pantothenate kinase in a buffered solution,
in the presence of a bi-valent metal salt,
with ATP as a phosphate source wherein the ATP is regenerated in situ,
to produce compound 9,
wherein $2X^+$ is (a) two protons, (b) one proton and one monovalent cation, (c) two monovalent cations wherein each said cation is the same or different, or (d) one divalent cation.

18. The method of claim 10 wherein the deoxyribose-phosphate aldolase comprises a polypeptide sequence having at least 85% sequence identity to SEQ ID NO: 6 or SEQ ID NO: 14.

19. The method of claim 4 wherein the phosphopentomutase comprises a polypeptide sequence having at least 85% sequence identity to SEQ ID NO: 8.

20. The method of claim 1 wherein the nucleobase is 2-fluoroadenine.

21. A method for synthesizing a 4'-ethynyl 2'-deoxy nucleoside or an analog thereof comprising combining compound 5

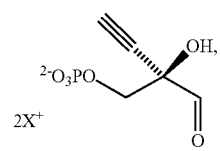
5 acetaldehyde and a nucleobase or an analog thereof,
with deoxyribose-phosphate aldolase, phosphopentomutase and purine nucleoside phosphorylase,
in a buffered solution containing a manganese (II) salt,
wherein $2X^+$ is (a) two protons, (b) one proton and one monovalent cation, (c) two monovalent cations wherein each cation is the same or different, or (d) one divalent cation.

22. The method of claim 21 further comprising removing inorganic phosphate byproduct from the reaction mixture.

23. The method of claim 22 comprising removing inorganic phosphate byproduct from the reaction mixture by (a) adding sucrose phosphorylase and sucrose to the reaction mixture or (b) adding calcium, magnesium, or manganese to the reaction mixture.

24. The method of claim 22 further comprising isolating the 4'-ethynyl 2'-deoxy nucleoside or analog thereof.

25. The method of claim 22 wherein the 4'-ethynyl 2'-deoxy nucleoside is
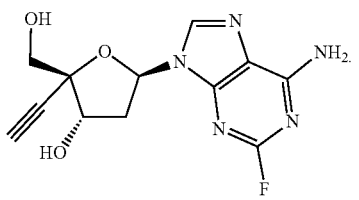 [SMILES: C#C[C@]1(CO)O[C@@H](n2cnc3c(N)nc(F)nc32)C[C@@H]1O]
26. The method of claim 25 further comprising isolating
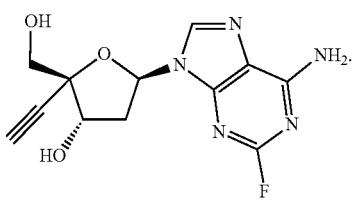 [SMILES: C#C[C@]1(CO)O[C@@H](n2cnc3c(N)nc(F)nc32)C[C@@H]1O]
27. The method of claim 21 wherein the nucleobase is 2-fluoroadenine.
* * * * *

UNITED STATES PATENT AND TRADEMARK OFFICE
CERTIFICATE OF CORRECTION

| | |
|---|---|
| PATENT NO. | : 12,037,623 B2 |
| APPLICATION NO. | : 17/257792 |
| DATED | : July 16, 2024 |
| INVENTOR(S) | : Mark A. Huffman et al. |

It is certified that error appears in the above-identified patent and that said Letters Patent is hereby corrected as shown below:

On the Title Page

Please delete the following:
"(71) Applicant: Merck Sharp & Dohme Corp."
And replace with:
--(71) Applicant: Merck Sharp & Dohme LLC--

Signed and Sealed this
Seventeenth Day of September, 2024

Katherine Kelly Vidal
*Director of the United States Patent and Trademark Office*